(12) United States Patent
Campadelli et al.

(10) Patent No.: US 11,007,236 B2
(45) Date of Patent: May 18, 2021

(54) HERPESVIRUS WITH MODIFIED GLYCOPROTEIN B

(71) Applicant: ALMA MATER STUDIORUM UNIVERSITA DI BOLOGNA, Bologna (IT)

(72) Inventors: Maria Gabriella Campadelli, Bologna (IT); Biljana Petrovic, Bologna (IT)

(73) Assignee: ALMA MATER STUDIORUM UNIVERSITA DI BOLOGNA, Bologna (IT)

( * ) Notice: Subject to any disclaimer, the term of this patent is extended or adjusted under 35 U.S.C. 154(b) by 4 days.

(21) Appl. No.: 16/307,683

(22) PCT Filed: Jun. 8, 2017

(86) PCT No.: PCT/EP2017/063944
§ 371 (c)(1),
(2) Date: Dec. 6, 2018

(87) PCT Pub. No.: WO2017/211941
PCT Pub. Date: Dec. 14, 2017

(65) Prior Publication Data
US 2019/0336551 A1 Nov. 7, 2019

(30) Foreign Application Priority Data

Jun. 9, 2016 (EP) .................................. 16173830

(51) Int. Cl.
| | |
|---|---|
| *A61K 35/763* | (2015.01) |
| *C07K 14/035* | (2006.01) |
| *C07K 14/47* | (2006.01) |
| *C12N 5/10* | (2006.01) |
| *C12N 7/00* | (2006.01) |
| *C12N 15/62* | (2006.01) |
| *C12N 15/86* | (2006.01) |

(52) U.S. Cl.
CPC .......... *A61K 35/763* (2013.01); *C07K 14/035* (2013.01); *C07K 14/473* (2013.01); *C12N 5/10* (2013.01); *C12N 7/00* (2013.01); *C12N 15/62* (2013.01); *C12N 15/86* (2013.01); *C07K 2319/74* (2013.01); *C12N 2710/16622* (2013.01); *C12N 2710/16632* (2013.01)

(58) Field of Classification Search
None
See application file for complete search history.

(56) References Cited

FOREIGN PATENT DOCUMENTS

| WO | 2003068809 A2 | 8/2003 |
|---|---|---|
| WO | 2004/033639 | 4/2004 |
| WO | 2007/024668 | 3/2007 |
| WO | 2007027774 A1 | 3/2007 |
| WO | 2008/103762 | 8/2008 |
| WO | 2009/013448 | 1/2009 |
| WO | 2009144755 A1 | 12/2009 |
| WO | 2011130749 A2 | 10/2011 |
| WO | 2015/066042 | 5/2015 |
| WO | 2016/128497 | 8/2016 |

OTHER PUBLICATIONS

Gallagher, J. et al., "Functional Fluorescent Protein Insertions in Herpes Simplex Virus gB Report on gB Conformation before and after Execution of Membrane Fusion," PLOS Pathogens, vol. 10, No. 9, Sep. 18, 2014, p. 1004373, 16 pages.
Gatta, V. et al., "The Engineering of a Novel Ligand in gH Confers to HSV an Expanded Tropism Independent of gD Activation by Its Receptors," PLOS Pathogens, vol. 11, No. 5, May 21, 2015, p. e1004907 (18 pages).
Leoni, V. et al., "A Strategy for Culivation of Retargeted Oncolytic Herpes Simplex Viruses in Non-cancer Cells," Journal of Virology, vol. 91, No. 10, Mar. 1, 2017, pp. e00067-e00017 (13 pages).
Petrovic, B. et al., "Insertion of a ligand to HER2 in gB retargets HSV tropism and obviates the need for activation of the other entry glycoproteins," PLOS Pathogens, vol. 13, No. 4, Apr. 19, 2017, p. e1006352 (25 pages).
Potel, C. et al., "Incorporation of green fluorescent protein into the essential envelope glycoprotein B of herpes simplex virus type 1," Journal of Virological Methods, vol. 105, No. 1, Aug. 1, 2002, pp. 13-21.
International Search Report and Written Opinion for corresponding PCT Patent Application PCT/EP2017/063944, dated Oct. 10, 2017 (16 pages).
Arii J. et al., "Non-Muscle Myosin IIA is a Functional Entry Receptor for Herpes Simplex Virus-1", Nature, 2010, 467, 859-862.
Arndt K. and Fin G.R., "GCN4 Protein, a Positive Transcription Factor in Yeast, Binds General Control Promoters at All 5' TGACTC 3' Sequences", PNAS 1986, 83, 8516-8520.
Avitabile E. et al.,"Complexes Bewteen Herpes Simplex Virus Glycoproteins gD, gB, and gH Detected in Cells by Complementation of Split Enhanced Green Fluorecent Protein", Journal of Virology, 2007, 81, 11532-11537.

(Continued)

*Primary Examiner* — Stacy B Chen
(74) *Attorney, Agent, or Firm* — Greenberg Traurig, LLP; Melissa Hunter-Ensor; Jana E. Harris

(57) ABSTRACT

The present invention is directed to a recombinant herpesvirus comprising a heterologous polypeptide ligand capable of binding to a target molecule and fused to or inserted into glycoprotein B at specific sites. The herpesvirus may comprise more than one ligand, and the additional ligand(s) may be comprised by a modified glycoprotein D and/or modified glycoprotein H. This allows the herpesvirus to target a cell for therapeutic purposes, and a cell for virus production. The present invention further comprises a pharmaceutical composition comprising the herpesvirus, the herpesvirus for use in the treatment of a tumor, infection, degenerative disorder or senescence-associated disease, a nucleic acid and a vector coding for the gB, a polypeptide comprising the gB, and a cell comprising the herpesvirus, nucleic acid, vector or polypeptide. Moreover, a method for infecting a cell with the herpesvirus or for producing the herpesvirus is disclosed.

Figure 1:
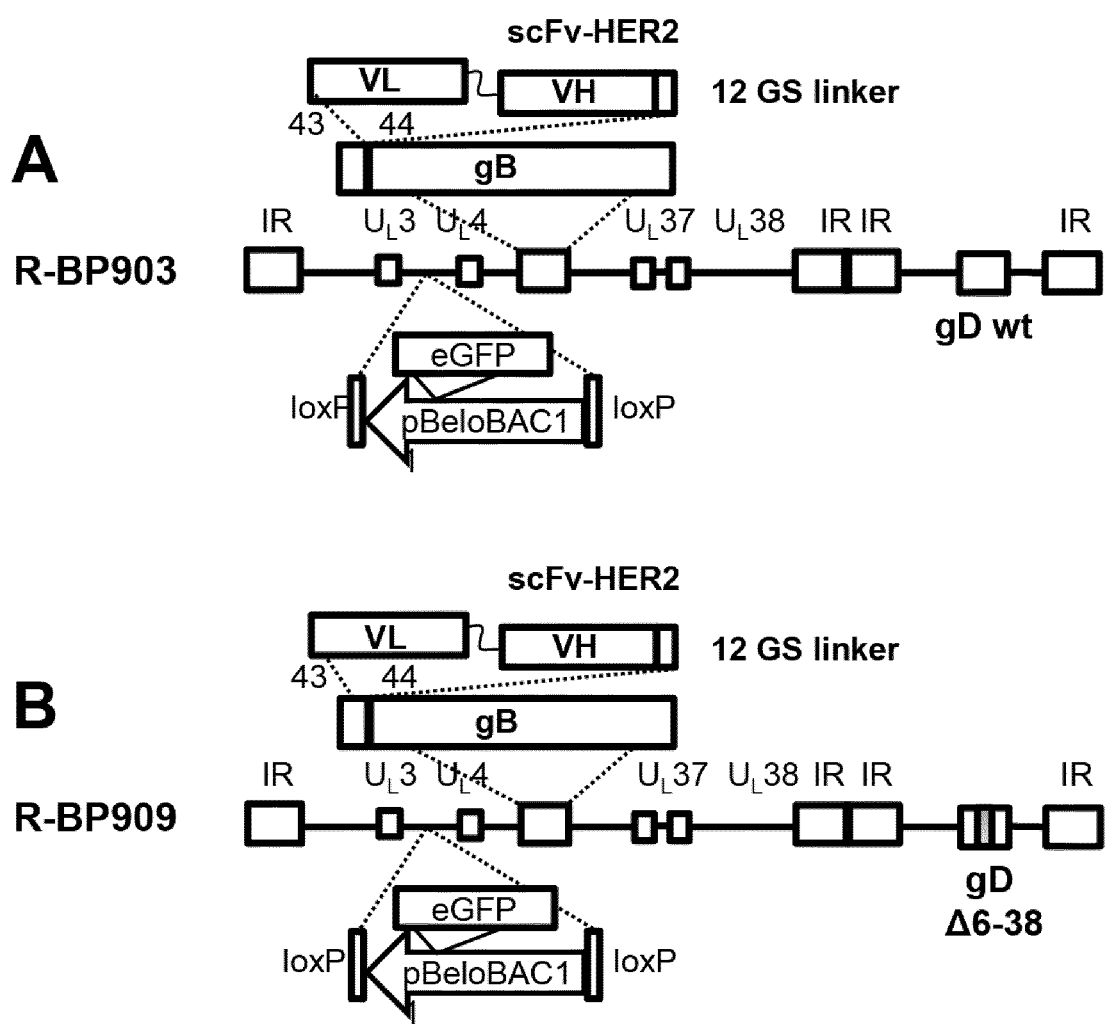

20 Claims, 20 Drawing Sheets
Specification includes a Sequence Listing.

(56) References Cited

OTHER PUBLICATIONS

Backovic M. et al., "Structure of a Trimeric Variant of the Epstein-Barr Virus Glycoprotein B", PNAS, 2009, 106, 2880-2885.
Backovic M. et al., "Structure of a Core Fragment of Glycoprotein H from Pseudorabies Virus in Complex with Antibody", PNAS, 2010, 107, 22635-22640.
Bender F.C. et al., "Antigenic and Mutational Analyses of Herpes Simplex Virus Glycoprotein B Reveal Four Functional Regions", J Virol., 2007, 81, 3827-3841.
Burke H.G. and Heldwein E.E., "Crystal Structure of the Human Cytomegalovirus Glycoprotein B", PLOS Pathogens, 2015, 11, e1005227.
Burleson, F.G. et al., Virology: A Laboratory Manual, 1992, ISBN-13: 978-0121447304.
Cairns T.M. et al., "Structure-Function Analysis of Herpes Simplex Virus Type 1 gD and gH-gL: Clues from gDgH Chimeras", Journal of Virology, 2003, 77, 6731-6742.
Castoldi R. et al., "Molecular Characterization of Novel Trispecific ErbB-cMet-IGFIR Antibodies and Their Antigen-Binding Properties", Protein Eng Des Sel, 2012, 25, 551-559.
Castoldi R. et al., "A Novel Bispecific EGFR/Met Antiboy Blocks Tumor-Promoting Phenotypic Effects Induced by Resistance to EGFR Inhibition and has Potent Antitumor Activity", Oncogene, 2013, 32, 5593-5601.
Chowdary T.K. et al., "Crystal Structure of the Conserved Herpesvirus Fusion Regulator Complex gH-gL", Nat Struct Mol Biol, 2010, 17, 882-888.
Di Giovine P. et al., "Structure of Herpes Simplex Virus Glycoprotein D Bound to the Human Receptor Nectin-1", PLoS Pathogens 2011, 7,e1002277.
Douglas J.T. et al., "A System for the Propagation of Adenoviral Vectors with Genetically Modified Receptor Specificities", Nat Biotechnol, 1999, 17, 470-475.
Gatta V. et al., Abstract # P-28, 9th International Conference on Oncolytic Virus Therapeutics, Boston 2015.
Heldwein E.E. et al., "Crystal Structure of Glycoprotein B from herpes Simplex Virus 1", Science, 2006, 313, 217-220.
Hope I.A and Struhl K., "GCN4, a Eukaryotic Transciptional Activator Protein, Binds as a Dimer to Target DNA", EMBO J, 1987, 6, 2781-2784.
Josan J.S. et al., "Cell-Specific Targeting by Heterobivalent Ligands", Bioconjug Chem, 2011, 22, 1270-1278.
Kamiyama H. et al., "Herpes Siplex Virus 1 Recombinant Virions Exhibiting the Amino Terminal Fragment of Urokinase-Type Plasminogen Activator can Enter Cells via the Cognate Receptor", Gene Therapy, 2006, 13, 621-629.
Karlin S. and Altschul S.F., "Methods for Assessing the Statistical Significance of Molecular Sequence Features by Using General Scoring Schemes", PNAS, 1990, 87, 2264-2268.
Karlin S. and Altschul S.F., "Applications and Statistics for Multiple High-Scoring Segments in Molecular Sequences", PNAS, 1993, 90, 5873-5877.
Li W. et al., "Identification of Functional Domains in Herpes Simplex Virus 2 Glycoprotein B", J Virol, 2006, 80, 3792-3800.
Lin E. & Spear P.G., "Random Linker-Insertion Mutagenesis to Identify Functional Domains of Herpes Simplex Virus Type 1 Glycoprotein B", PNAS, 2007, 104, 13140-13145.
Liu B.L. et al., "ICP34.5 Deleted Herpes Simplex Virus with Enhanced Oncolytic, Immune Stimulating, and Anti-Tumour Properties", Gene Ther., 2003, 10, 292-303.
Lorentzen E.U. et al., "Replication-Competent Herpes Simplex Virus Type 1 Mutant Expressing an Autofluorescent Glycoprotein H Fusion Protein", Intervirology, 2001, 44, 232-242.
Matsuura H. et al., "Crystal Structure of the Epstein-Barr Virus (EBV) Glycoprotein H/Glycoprotein L (gH/gL) Complex", PNAS, 2010, 107, 22641-22646.
Menotti L. et al., "Construction of a Fully Retargeted Herpes Simplex Virus 1 Recombinant Capable of Entering Cells Solely via Human Epidermal Growth Factor Receptor2", J Virol., 2008, 82, 10153-10161.
Menotti L. et al., "Inhibition of Human Tumor Growth in Mice by an Oncolytic Herpes Simplex Virus Designed to Target Solely HER-2-Positive Cells", PNAS, 2009, 106, 9039-9044.
Morgan A.A. and Rubenstein E., "Proline: The Distribution, Frequency, Positioning, and Common Functional Roles of Proline and Polyproline Sequences in the Human Proteome", PLoS One, 2013, 8, e53785.
Nakamura T. et al., "Rescue and Propagation of Fully Retargeted Oncolytic Measles Viruses", Nat Biotechnol, 2005, 23, 209-214.
Needleman S.B. and Wunsch C. D., "A General Method Applicable to the Search for Similarities in the Amino Acid Sequence of Two Proteins", J Mol Biol, 1970, 48, 443-453.
Pearson W.R. and Lipman D. J., "Improved Tools for Biological Sequence Comparison", PNAS, 1988, 85, 2444-2448.
Peterson R.B. and Goyal S.M., "Propagation and Quantitation of Animal Herpesviruses in Eight Cell Culture Systems", Comp Immunol Microbiol Infect Dis. 1988, 11, 93-98.
Sandri-Goldin R.M., Alpha Herpesviruses: Molecular and Cellular Biology, Caister Academic Press, 2006.
Satoh T. et al., "PILRa is a Herpes Simplex Virus-1 Entry Co-Receptor that Associates with Glycoprotein B", Cell, 2008, 132, 935-944.
Shallal H.M. et al., "Heterobivalent Agents Targeting PSMA and Integrin-$\alpha_v\beta e$", Bioconjug Chem, 2014, 25, 393-405.
Shibata T. et al., "Development of an Oncolytic HSV Vector Fully Retargeted Specifically to Cellular EpCAM for Virus Entry and Cell-to-Cell Spread", Gene Therapy, 2016, 23, 479-488.
Smith T.F. and Waterman M.S., "Comparison of Biosequences", Add APL Math, 1981, 2, 482-489.
Suenaga T. et al., "Myelin-Associated Glycoprotein Mediates Membrane Fusion and Entry of Neurotropic Herpesviruses", PNAS 2010, 107, 866-871.
Uchida H. et al., "Effective Treatment of an Orthotopic Xenograft Model of Human Glioblastoma Using an EGFR-Retargeted Oncolytic Herpes Simplex Virus", Mol Ther, 2013, 21, 561-569.
Xu L. et al., "Heterobivalent Ligands Target Cell-Surface Receptor Combinations in Vivo", PNAS, 2012, 109, 21295-21300.
Zahnd C. et al., "Directed In Vitro Evolution and Crystallographic Analysis of a Peptide-Binding Single Chain Antibody Fragment (scFv) with Low Picomolar Affinity", J Biol Chem, 2004, 279, 18870-18877.
Zhou, G. et al., "Glycoprotein D or J Delivered in trans Blocks Apoptosis in SK-N-SH Cells Induced by a Herpes Simplex Virus 1 Mutant Lacking Intact Genes Expressing Both Glycoproteins", J Virol, 2000, 74, 11782-11791.
Zhou G. and Roizman B., "Characterization of a Recombinant Herpes Simplex Virus 1 Designed to Enter Cells via the IL13R$\alpha$2 Receptor of Malignant Glioma Cells", J Virol, 2005, 79, 5272-5277.

Fig. 1 (contd.)
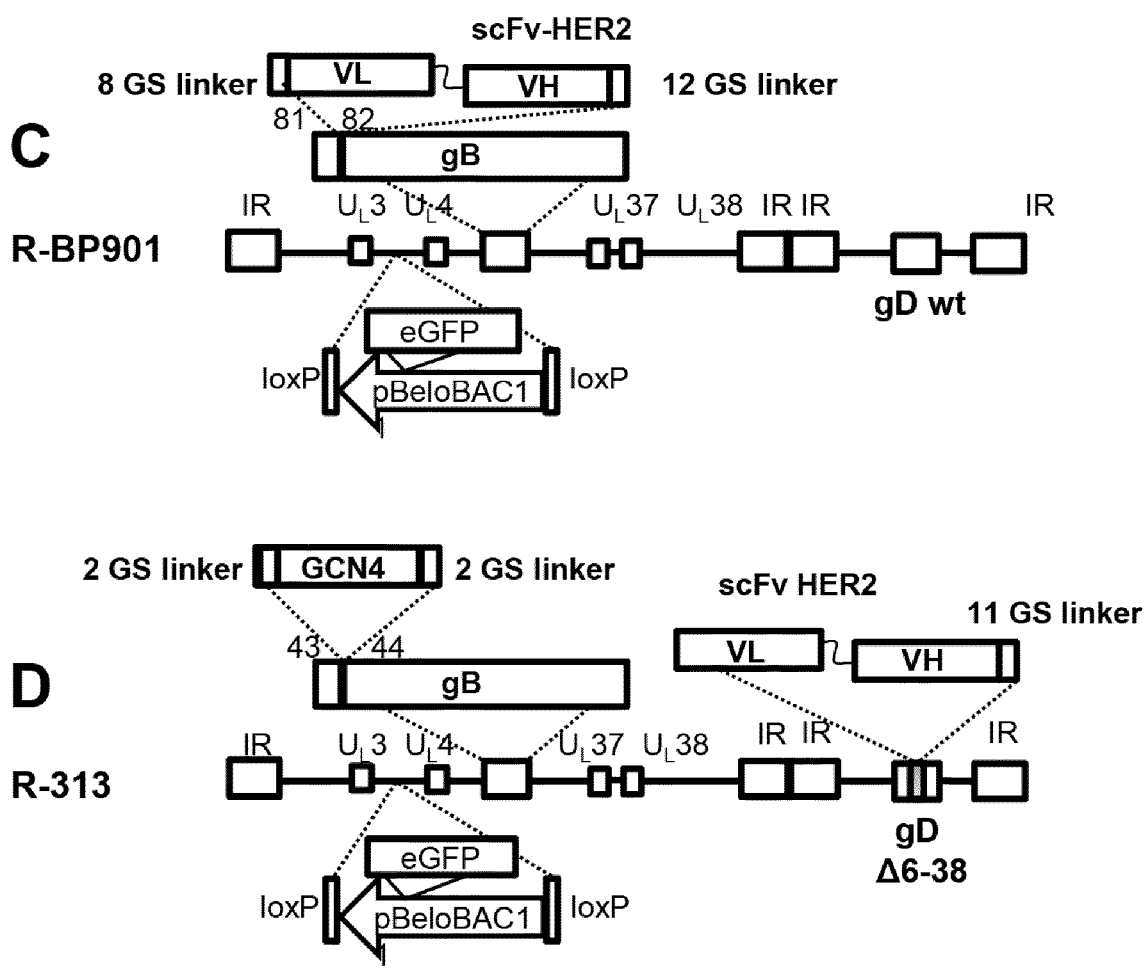

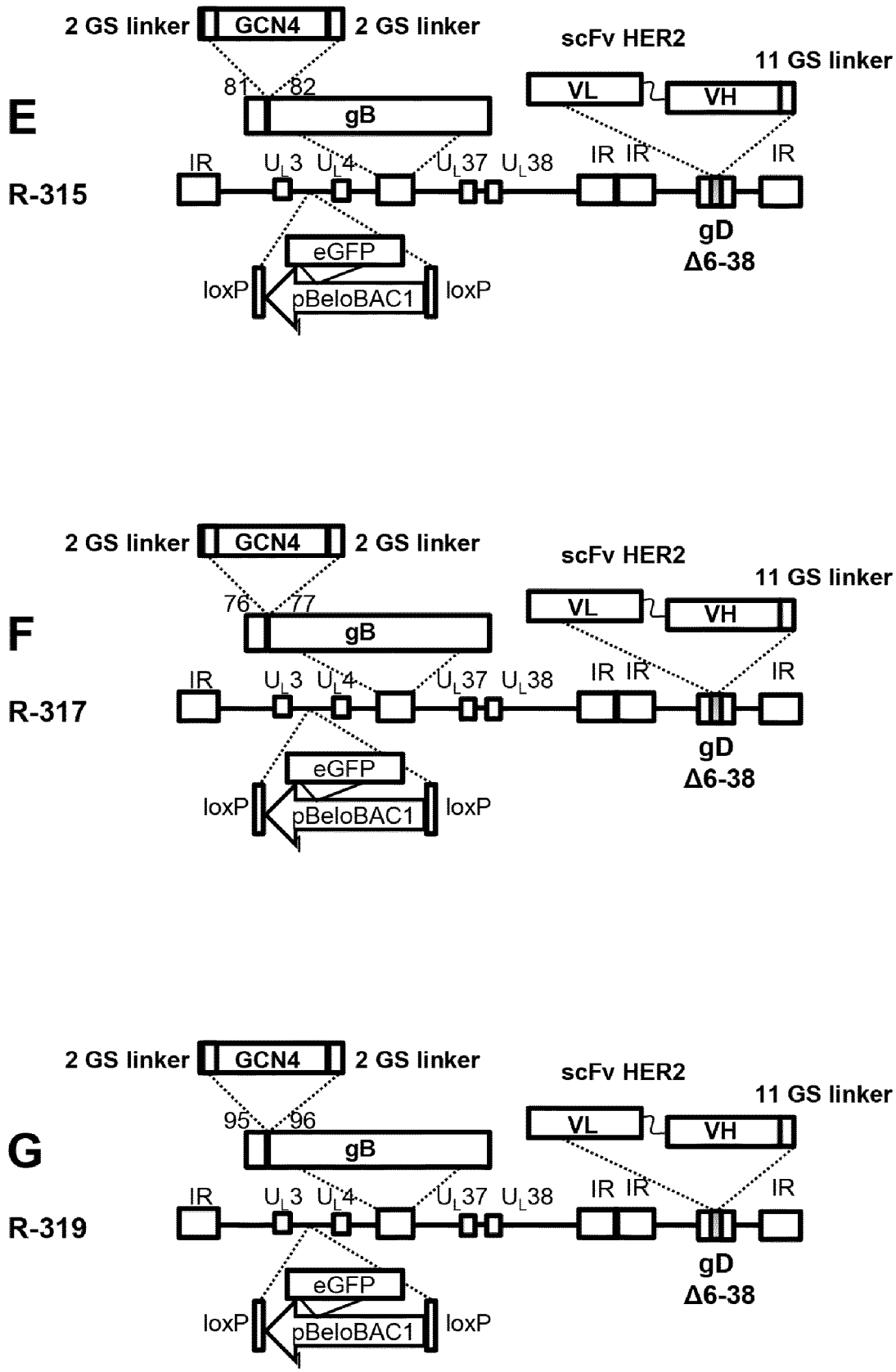
Fig. 1 (contd.)

Fig. 2

Figure 8:
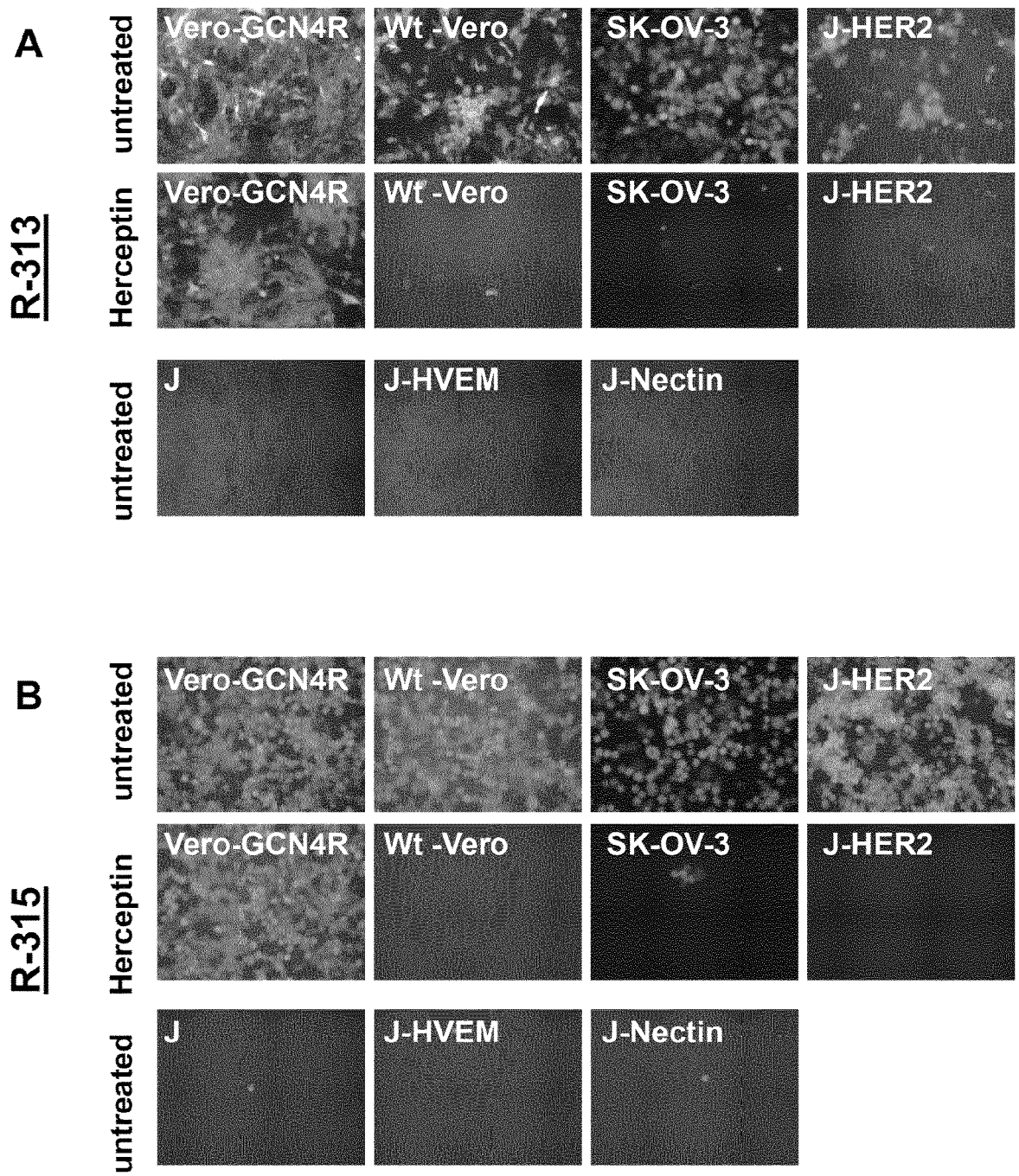

Fig. 8 (contd.)
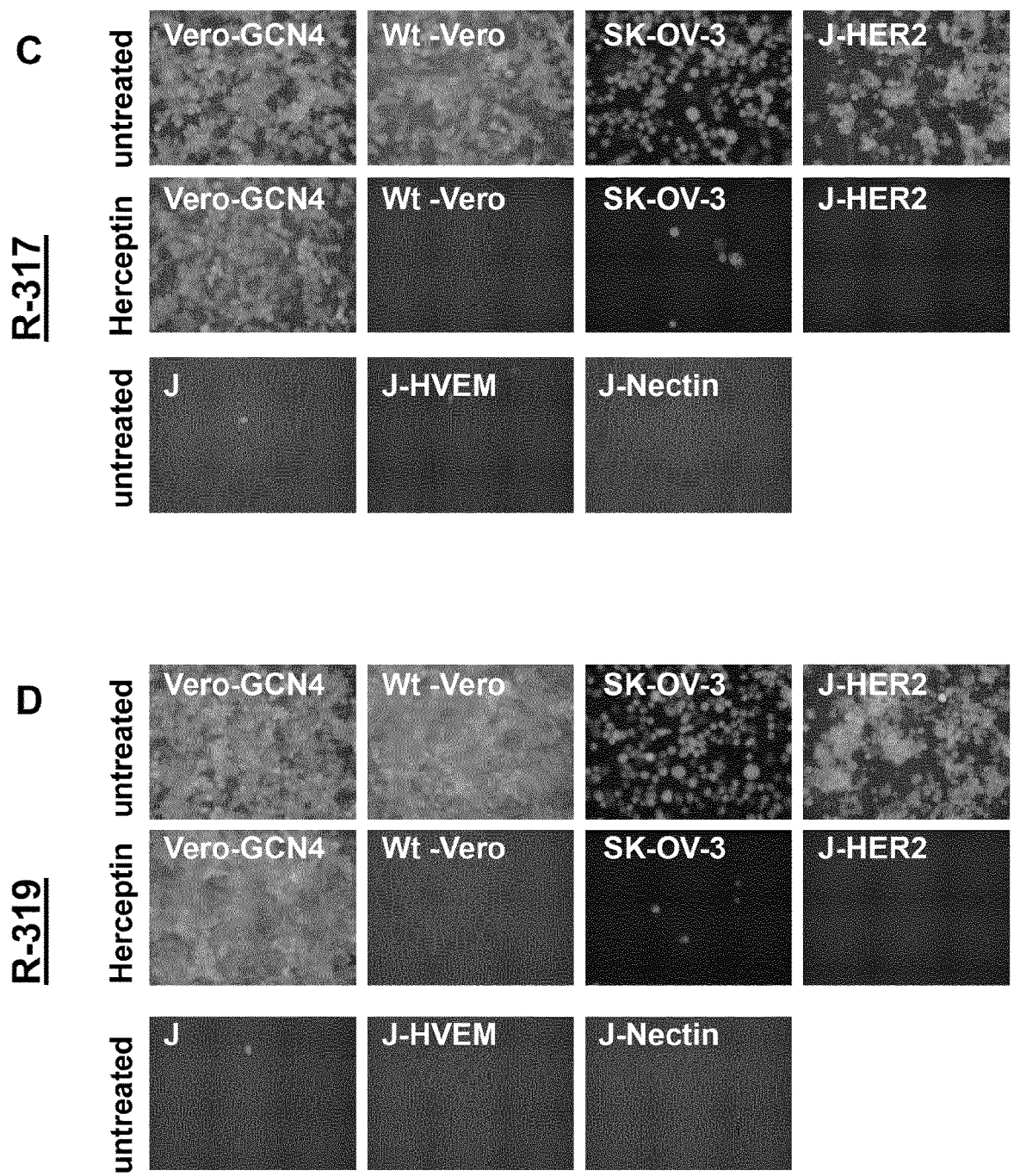

Figure 11:
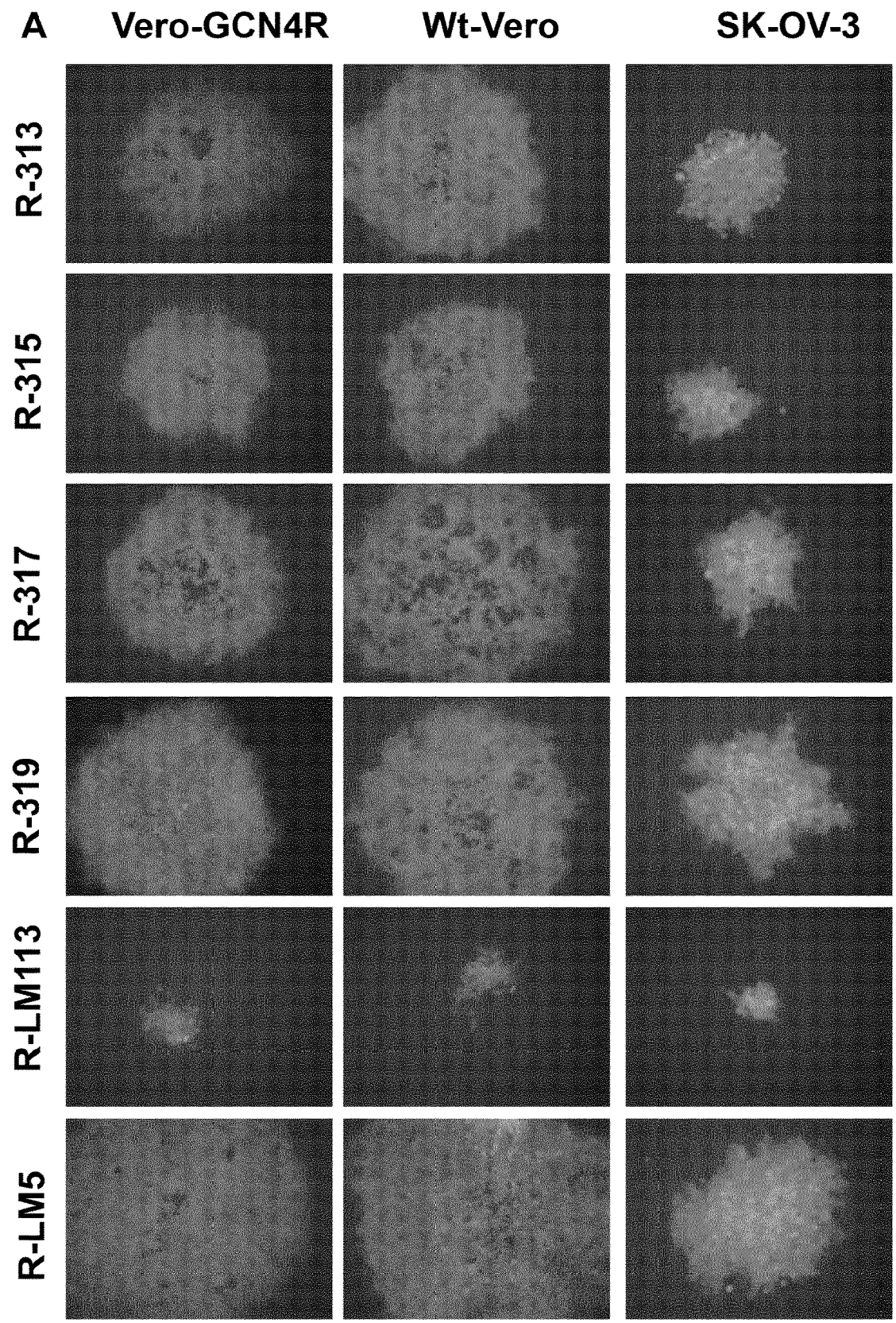

Fig. 11 (contd.)
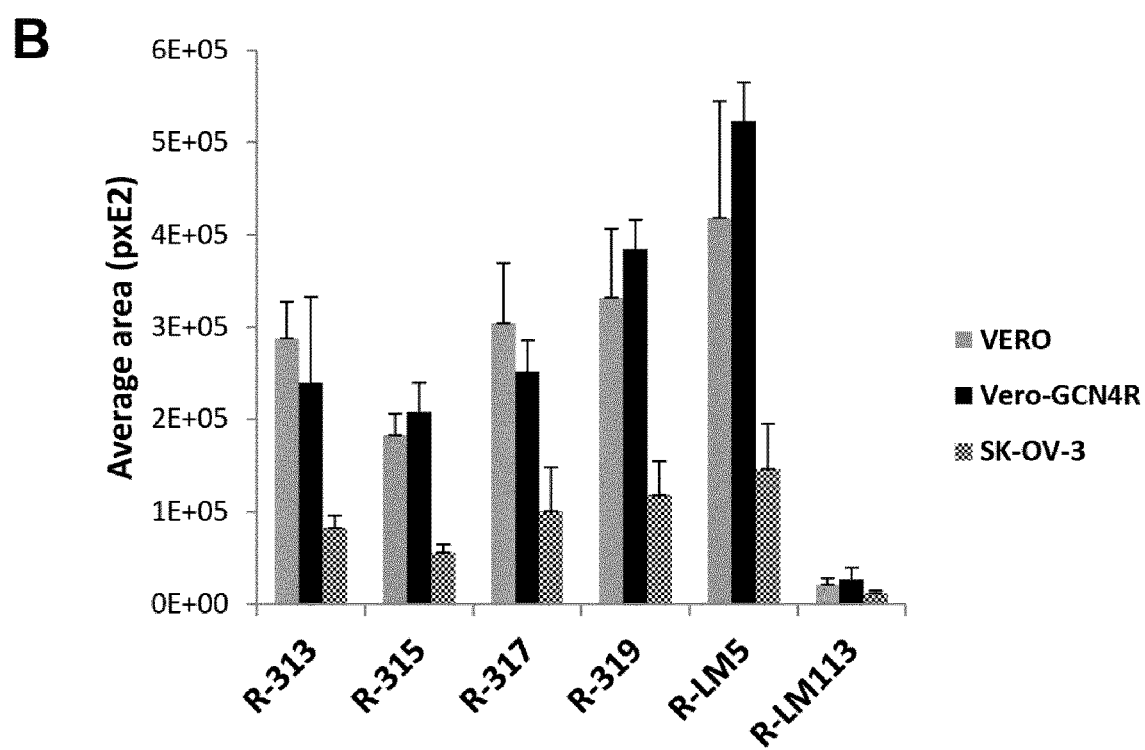

HERPESVIRUS WITH MODIFIED GLYCOPROTEIN B

CROSS-REFERENCE TO RELATED APPLICATIONS

This application is the U.S. national phase application, pursuant to 35 U.S.C. § 371, of PCT International Application Ser. No.: PCT/EP2017/063944, filed Jun. 8, 2017, designating the United States and published in English, which claims the benefit of and priority to European Patent Application No. 16173830.7, filed Jun. 9, 2016, which is incorporated herein by reference in its entirety.

SEQUENCE LISTING

The instant application contains a Sequence Listing which has been submitted electronically in ASCII format and is hereby incorporated by reference in its entirety. Said ASCII copy, created on Jul. 11, 2019, is named 182946_010300_SL.txt and is 116,487 bytes in size.

BACKGROUND OF THE INVENTION

The work leading to this invention has received funding from the European Research Council under the European Union's Seventh Framework Program (FP7/2007-2013)/ERC grant agreement n° 340060.

Despite a steady development in healthcare, the burden of diseases and pathologies that cannot be treated or cannot be sufficiently treated, remains elevated. Eminent among these are numerous forms of tumors, in particular metastatic forms of tumors that are treated with chemo-radio-therapy or biological medicaments, or combinations thereof, however, with limited success.

An alternative approach of tumor treatment is oncolytic virotherapy, whereby a replication competent virus infects the tumor cells, spreads from cell to cell of the tumor and destroys them.

Oncolytic virotherapy can be combined with immunotherapy of cancers. Thus the patient may be administered both oncolytic virus and the immunotherapeutic agents, or, the oncolytic virus has been engineered to express a cytokine, chemokine, or molecules such as immune checkpoint regulators, that boost the immune response of the host to the tumor. Immune checkpoint regulators include antibodies or single chain antibodies to CTLA4, PD1, PDL1, LAG3, KIR, NKG2A, TIM3, TIGIT, CD96, BTLA. They can be administered singly or in combination. Included in this category of recombinant oncolytic viruses capable to elicit an immune response to the tumor is T-VEC, renamed Talimogene laherparepvec (commercial name Imlygic), an HSV that encodes GM-CSF, approved by FDA for the treatment of metastatic melanoma Herpes simplex virus (HSV) is a pathogen virus for humans. In culture, it infects a large number of mammalian cells. It is an enveloped virus which enters the cell by membrane fusion, either at the plasma membrane or through endocytosis, depending on the target cell type. Entry of HSV into a target cell is a multistep process, requiring complex interactions and conformational changes of viral glycoproteins gD, gH/gL, gC and gB. These glycoproteins constitute the virus envelope which is the most external structure of the HSV particle and consists of a membrane. For cell entry, gC and gB mediate the first attachment of the HSV particle to cell surface heparan sulphate. Thereafter, gD binds to at least two alternative cellular receptors, being Nectin-1 and HVEM or HVEA, causing conformational changes in gD that initiates a cascade of events leading to virion-cell membrane fusion. Thereby, the intermediate protein gH/gL (a heterodimer) is activated which triggers gB to catalyze membrane fusion. Thereby, gB is membrane bound and functions as a viral fusogen.

Oncolytic HSVs (o-HSV) have been used in recent years as oncolytic agents. As wild-type HSV viruses are highly virulent, there is a requirement that the o-HSVs are attenuated. T-VEC/Imlygic and the viruses that have reached clinical trials carry deletion of one or more HSV genes, including the gamma $\gamma_1 34.5$ gene, which encodes the ICP34.5 protein whose role is to preclude the shut off of protein synthesis in infected cells, and the UL39 gene, which encodes the large subunit of ribonucleotide reductase. In addition to some disadvantages which are shown by these viruses, such as the failure to produce high yield of progeny viruses, they furthermore have the preserved ability to bind to any cell bearing their natural receptors. Thus, the therapeutic effect of tumor cell killing is diminished and the viruses may have limitations in medical use.

One approach to overcome these limits has been genetic engineering of o-HSVs which exhibit a highly specific tropism for the tumor cells, and are otherwise not attenuated. This approach has been defined as retargeting of HSV tropism to tumor-specific receptors.

The retargeting of HSV to cancer-specific receptors entails the genetic modifications of gD, such that it harbors heterologous sequences which encode a specific ligand. Upon infection with the recombinant virus, progeny viruses are formed which carry in their envelope the chimeric gD-ligand glycoprotein, in place of wildtype gD. The ligand interacts with a molecule specifically expressed on the selected cell and enables entry of the recombinant o-HSV into the selected cell. Examples of ligands that have been successfully used for retargeting of HSV are IL13a, uPaR, a single chain antibody to HER2 and a single chain antibody to EGFR.

The retargeting through modification of glycoproteins has also been attempted with gC. The inserted ligands were EPO and IL13. The virus carrying the gC-EPO polypeptide attached to cells expressing the EPO receptor. However, this attachment did not lead to infectious entry. In addition, the gC-IL13 polypeptide was present in a virus that carried a second copy of IL13 in the gD gene. Therefore, it cannot be inferred from those studies whether the gC-IL13 contributed or not to the retargeting to the IL13 alpha2 receptor.

The retargeting through genetic modification of gH has also been achieved. The inserted ligand was a single-chain antibody (scFv) directed to HER2, without or with deletions within the gH gene. The virus was successfully retargeted to a cell carrying the HER2 receptor (Gatta et al., 2015). In addition, a recombinant virus was constructed which contained the scFv directed to HER2 in gH and an scFv directed to EGFR in the mature gD protein. This resulted in double retargeting to the cell carrying the receptors. Further, a recombinant virus was constructed which contained the scFv directed to HER2 in gH and the scFv directed to HER2 in the mature gD protein. This resulted in double retargeting to the HER2 receptors (PCT application (Abstract #P-28, 9$^{th}$ International conference on Oncolytic virus Therapeutics, Boston 2015).

The retargeting of viruses via gB has never been reported. While insertion sites within gB gene were identified which resulted in viable viral mutants with preserved membrane fusion activity (Gallagher et al., 2014; Lin and Spear, 2007; Potel et al., 2002), the assays used for analyzing the polypeptide-gB fusions did not predict whether—in the case that the inserted polypeptide is a heterologous peptide capable to bind a target receptor—the ensuing recombinant would contribute to the fusion activity of gB and exhibit a tropism re-addressed (retargeted) to the receptor targeted by the ligand. Foremost, the experience in the art predicts that any effort of retargeting the tropism of a virus, including HSV, is only successful if the glycoprotein chosen for modifications, e.g. for insertion of a heterologous ligand, is a determinant of the virus tropism. Receptors have been claimed for HSV gB; they are heparan sulfate proteoglycans to which gB and gC bind, Myelin-associated glycoprotein MAG, paired immunoglobulin-like type 2 receptor alpha (PILRalpha), DC-SIGN and non-muscle myosin heavy chain 9 MYH9/NMHC-IIA. In no case, the interaction of gB with these molecules was shown to determine HSV tropism. Thus, PILRalpha participates in entry of HSV into monocytic cells, a cell type not usually targeted by HSV, a virus which infects preferentially epidermal and neuronal cells. For the other receptors the role they play in HSV infection was not investigated. Hence, an expert in the art can not predict that suitable modifications to gB can result in retargeted tropism to the target receptor of choice.

There is a need in the art to provide several alternative retargeting strategies. This need stems from the heterogeneity of cancer cells in a same tumor, whereby cells express different receptors, the need to eliminate cancer stem cells, which may express a repertoire of receptors different from those of the cancer cells, or the insurgence of cells resistant to targeted therapy.

The present invention describes a recombinant HSV with a modified gB protein which retargets the virus to receptors of cells which need to be eliminated.

The present inventors have shown that it is possible to construct a recombinant HSV which comprises a polypeptide ligand directed to a specific cellular receptor as a fusion protein with gB, whereby due to the presence of the ligand, the HSV is retargeted to cells carrying the receptor. Furthermore, the HSV has been shown to maintain infectivity, resulting in the entry into the cells carrying the receptor and killing of the infected cells.

DETAILED DESCRIPTION OF THE INVENTION

In the following, the present invention is described in detail. The features of the present invention are described in individual paragraphs. This, however, does not mean that a feature described in a paragraph stands isolated from a feature or features described in other paragraphs. Rather, a feature described in a paragraph can be combined with a feature or features described in other paragraphs.

The term "comprise/es/ing", as used herein, is meant to "include or encompass" the disclosed features and further features which are not specifically mentioned. The term "comprise/es/ing" is also meant in the sense of "consist/s/ing of" the indicated features, thus not including further features except the indicated features. Thus, the product of the present invention may be characterized by additional features in addition to the features as indicated.

In a first aspect, the present invention provides a recombinant herpesvirus comprising a heterologous polypeptide ligand capable of binding to a target molecule and fused to or inserted into glycoprotein B (gB) present in the envelope of the herpesvirus, wherein the ligand is fused to gB, or wherein the ligand is inserted at any amino acid within a disordered region of gB, but is not inserted at any amino acid within the region spanning from amino acids 77 to 88 of gB according to SEQ ID NO: 1 or within a corresponding region of a homologous gB, or wherein the ligand is inserted at any amino acid within a region spanning from amino acids 31 to 77 or 88 to 184, preferably amino acids 31 to 77 or 88 to 136 or more preferably 31 to 77 or 88 to 108, and/or within a region spanning from amino acids 409 to 545, preferably amino acids 459 to 545 or more preferably amino acids 459 to 497, or still more preferably amino acids 460 to 491, of gB according to SEQ ID NO: 1 or within a corresponding region of a homologous gB.

Furthermore, the present invention provides a recombinant herpesvirus comprising a heterologous polypeptide ligand capable of binding to a target molecule and inserted into glycoprotein B (gB) present in the envelope of the herpesvirus, wherein the ligand has a length of 5 to 120 amino acids and is inserted at any amino acid within a region spanning from amino acids 77 to 88 of gB according to SEQ ID NO: 1 or within a corresponding region of a homologous gB.

In an embodiment thereof, the herpesvirus has the capability of binding to a cell expressing or binding the target molecule, preferably of fusing with the cell, more preferably of entering the cell, most preferably of killing the cell.

In an embodiment thereof, the target molecule is present on a diseased cell, preferably the diseased cell is a tumor cell, an infected cell, a degenerative disorder-associated cell or a senescent cell, or the target molecule is present on a cell present in cell culture, preferably the cell is a cultured cell suitable for growth of the herpesvirus, more preferably a cell line approved for herpesvirus growth, even more preferably a Vero, 293, 293T, HEp-2, HeLa, BHK, or RS cell, most preferably a Vero cell.

In an embodiment thereof, the target molecule present on a diseased cell is a tumor-associated receptor, preferably a member of the EGF receptor family, including HER2, EGFR, EGFRIII, or EGFR3 (ERBB3), EGFRvIII, or MET, FAP, PSMA, CXCR4, CEA, CADC, Mucins, Folate-binding protein, GD2, VEGF receptors 1 and 2, CD20, CD30, CD33, CD52, CD55, the integrin family, IGF1R, the Ephrin receptor family, the protein-tyrosine kinase (TK) family, RANKL, TRAILR1, TRAILR2, IL13Ralpha, UPAR, Tenascin, a member of the immune checkpoint family regulators, including PD-1, PD-L1, CTL-A4, TIM-3, LAG3, or IDO, tumor-associated glycoprotein 72, ganglioside GM2, A33, Lewis Y antigen, or MUC1, most preferably HER2, or the target molecule present on a cell present in cell culture is an artificial molecule, preferably an antibody, an antibody derivative or an antibody mimetic, more preferably a single-chain antibody (scFv), still more preferably an scFv capable of binding to a part of the GCN4 yeast transcription factor, still more preferably an scFv capable of binding to the part of the GCN4 yeast transcription factor as comprised by SEQ ID NO: 37, still more preferably the scFv as comprised by SEQ ID NO: 39, most preferably the molecule identified by the sequence of SEQ ID NO: 41.

In an embodiment thereof, the ligand is a natural polypeptide or an artificial polypeptide, preferably the ligand is capable of binding to a target molecule present on a cell present in cell culture or to a target molecule present on a diseased cell, more preferably the ligand is a natural ligand of a target molecule which is accessible on a cell, a part of the natural ligand capable of binding to the target molecule, a part of a natural polypeptide, an antibody, an antibody derivative, an antibody mimetic, still more preferably the ligand is a part of the natural polypeptide capable of binding to a target molecule present on a cell present in cell culture or an scFv, still more preferably the ligand is a part of the GCN4 yeast transcription factor such as the part of the GCN4 yeast transcription factor as comprised by SEQ ID NO: 37 or an scFv capable of binding to a target molecule present on a tumor cell, preferably HER2, most preferably the ligand is the molecule identified by the sequence of SEQ ID NO: 37 or the scFv identified by SEQ ID NO: 32.

In an embodiment thereof, the target molecule is HER2, the ligand is an scFv as identified by SEQ ID NO: 32 and the diseased cell is a tumor cell expressing HER2, preferably a breast cancer cell, ovary cancer cell, stomach cancer cell, lung cancer cell, head and neck cancer cell, osteosarcoma cell, glioblastoma multiforme cell, or salivary gland tumor cell, and/or the target molecule is the molecule identified by the sequence of SEQ ID NO: 41, the ligand is the molecule identified by the sequence of SEQ ID NO: 37, and the cell is present in cell culture and expresses the molecule identified by the sequence of SEQ ID NO: 41.

In an embodiment thereof, one or more ligands are fused to or inserted into gB, preferably the gB comprises a ligand capable of binding to a target molecule present on a cell present in cell culture and a ligand capable of binding to a target molecule present on a diseased cell.

In an embodiment thereof, the herpesvirus comprises a modified gD and/or a modified gH, preferably wherein the gB comprises a ligand capable of binding to a target molecule present on a cell present in cell culture and the modified gD and/or the modified gH comprise(s) a ligand capable of binding to a target molecule present on a diseased cell, most preferably the gB comprises the sequence identified by SEQ ID NO: 37, the target molecule is the molecule with the sequence identified by SEQ ID NO: 41, and the cell is present in cell culture and expresses the molecule identified by the sequence of SEQ ID NO: 41, and the modified gD and/or the modified gH comprise(s) an scFv identified by SEQ ID NO: 32, the target molecule is HER2, and the cell is a tumor cell expressing HER2, preferably a breast cancer cell, ovary cancer cell, stomach cancer cell, lung cancer cell, head and neck cancer cell, osteosarcoma cell, glioblastoma multiforme cell, or salivary gland tumor cell.

In an embodiment thereof, the gD is modified to have a deletion of amino acids 30 to 38 of gD or a subset thereof, preferably the gD is modified to have a deletion of amino acid 30 and/or amino acid 38, more preferably the gD is modified to have a deletion of amino acid 30 and amino acid 38, with regard to mature gD according to SEQ ID NO: 62 or a corresponding region of a homologous gD.

In an embodiment thereof, a heterologous polypeptide ligand is inserted into gD instead of amino acids 30 to 38 or a subset thereof, preferably the heterologous polypeptide ligand is inserted instead of amino acid 30 or amino acid 38, more preferably the heterologous polypeptide ligand is inserted instead of amino acid 38 and amino acid 30 is deleted, with regard to mature gD according to SEQ ID NO: 62 or a corresponding region of a homologous gD.

In an embodiment thereof, the herpesvirus encodes one or more molecule(s) that stimulate(s) the host immune response against a cell, preferably a diseased cell.

Glycoprotein B (gB) is an envelope protein which is present on the outer surface of herpesviridae and is involved in the binding of the virus to a cell and invasion into the cell. Among the glycoproteins which are involved in cell entry, gB is the fusogen that undergoes fusion-promoting conformational rearrangement upon stimulation via gD and gH/gL. gB is composed of 904 amino acids including 30 amino acids signal peptide, 696 amino acids ectodomain, 69 amino acids transmembrane domain, and 109 amino acids C-tail. gB belongs to the most highly conserved glycoproteins across the Herpesviridae family. The crystal structure of herpes simplex virus (HSV) type 1 gB was solved in its post-fusion conformation; it is a trimer, with five structural domains (I-V). Domain I extends from amino acids 154 to 363, domain II extends from amino acids 142 to 153 and 364 to 459, followed by the disordered region of amino acids 460 to 491, domain III extends from amino acids 117 to 133, 500 to 572, and 661 to 669, domain IV extends from amino acids 111 to 116 and 573 to 660, and domain V extends from amino acids 670 to 725 (Heldwein et al., 2006). The N-terminal region with its disordered structure extends from amino acids 31 to 108. The crystal structures of EBV and HCMV were also solved, and are essentially similar to that of HSV type 1 (Backovic et al., 2009; Burke and Heldwein, 2015). Due to its unique structure, herpesvirus gBs belong to a new class of viral membrane fusion glycoproteins, class III. The nuciceotide and amino acid sequences of a variety of gBs of different herpesviruses are known in the art. For illustrative purposes only, without being limited thereto, reference is made to the amino acid sequence of gB of human herpesvirus 1 disclosed herein as SEQ ID NO: 1. The corresponding nucleotide sequence and the amino acid sequence are available from the NCBI (National Centre for Biotechnology Information; National Library of Medicine, Bethesda, Md. 20894, USA; www.ncbi.nlm.nih.gov) under the accession number "Genome", GU734771.1, coordinates from 52996 to 55710.

```
                                                                  SEQ ID NO: 1
  1    MRQGAPARGC  RWFVVWALLG  LTLGVLVASA  APSSPGTPGV  AAATQAANGG  PATPAPPAPG

61    PAPTGDTKPK  KNKKPKNPPP  PRPAGDNATV  AAGHATLREH  LRDIKAENTD  ANFYVCPPPT

121    GATVVQFEQP  RRCPTRPEGQ  NYTEGIAVVF  KENIAPYKFK  ATMYYKDVTV  SQVWFGHRYS

181    QFMGIFEDRA  PVPFEEVIDK  INAKGVCRST  AKYVRNNLET  TAFHRDDHET  DMELKPANAA

241    TRTSRGWHTT  DLKYNPSRVE  AFHRYGTTVN  CIVEEVDARS  VYPYDEFVLA  TGDFVYMSPF

301    YGYREGSHTE  HTSYAADRFK  QVDGFYARDL  TTKARATAPT  TRNLLTTPKF  TVAWDWVPKR

361    PSVCTMTKWQ  EVDEMLRSEY  GGSFRFSSDA  ISTTFTTNLT  EYPLSRVDLG  DCIGKDARDA

421    MDRIFARRYN  ATHIKVGQPQ  YYLANGGFLI  AYQPLLSNTL  AELYVREHLR  EQSRKPPNPT

481    PPPPGASANA  SVERIKTTSS  IEFARLQFTY  NHIQRHVNDM  LGRVAIAWCE  LQNHELTLWN

541    EARKLNPNAI  ASATVGRRVS  ARMLGDVMAV  STCVPVAADN  VIVQNSMRIS  SRPGACYSRP
```

```
-continued
601    LVSFRYEDQG PLVEGQLGEN NELRLTRDAI EPCTVGHRRY FTFGGGYVYF EEYAYSHQLS

661    RADITTVSTF IDLNITMLED HEFVPLEVYT RHEIKDSGLL DYTEVQRRNQ LHDLRFADID

721    TVIHADANAA MFAGLGAFFE GMGDLGRAVG KVVMGIVGGV VSAVSGVSSF MSNPFGALAV

781    GLLVLAGLAA AFFAFRYVMR LQSNPMKALY PLTTKELKNP TNPDASGEGE EGGDFDEAKL

841    AEAREMIRYM ALVSAMERTE HKAKKKGTSA LLSAKVTDMV MRKRRNTNYT QVPNKDGDAD

901    EDDL
``` gB homologs are found in all members of the Herpesviridae. Therefore, the term "glycoprotein B", as referred to herein, refers to any gB homolog found in Herpesviridae. Alternatively, gB, as referred to herein, refers to any gB which has an amino acid identity to the sequence of SEQ ID NO: 1 of at least 70%, 80%, 85%, 90%, 95%, 96%, 97%, 98%, 99% or 100%. Alternatively, the gB, as referred to herein, refers to any gB which has an amino acid homology to SEQ ID NO: 1 of at least 50%, 60%, 70%, 80%, 85%, 90%, 95%, or 100%. The gB, as referred to herein, also includes a fragment of gB. Preferably, gB, as referred to herein, including any gB found in Herpesviridae, any gB having an amino acid identity to the sequence of SEQ ID NO: 1, as defined above, and any fragment of a gB, has the same activity of the gB according to SEQ ID NO: 1. More preferably, during the entry process of the virus into a cell, gB undergoes a conformational change promoting fusion of the virus with the membrane of the cell, and still more preferably, it acts as a fusogen mediating the fusion of the virus with the cell membrane.

The percentage of "sequence identity," as used herein, refers to the percentage of amino acid residues which are identical in corresponding positions in two optimally aligned sequences. It is determined by comparing two optimally aligned sequences over a comparison window, where the fragment of the amino acid sequence in the comparison window may comprise additions or deletions (e.g., gaps or overhangs) as compared to the reference sequence, SEQ ID NO: 1 (which does not comprise additions or deletions) for optimal alignment of the two sequences. The percentage is calculated by determining the number of positions at which the identical amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman, 1981, by the homology alignment algorithm of Needleman and Wunsch, 1970, by the search for similarity method of Pearson and Lipman, 1988, by the algorithm of Karlin and Altschul, 1990, modified by Karlin and Altschul, 1993, or by computerized implementations of these algorithms (GAP, BESTFIT, BLAST, PASTA, and TFASTA in the Wisconsin Genetics Software Package, Genetics Computer Group (GCG), 575 Science Dr., Madison, Wis.), or by inspection. GAP and BESTFIT are preferably employed to determine the optimal alignment. Typically, the default values of 5.00 for gap weight and 0.30 for gap weight length are used.

The "percentage of homology", as used herein, refers to the percentage of amino acid residues which are homologous in corresponding positions in two optimally aligned sequences. The "percentage of homology" between two sequences is established in a manner substantially identical to what has been described above with reference to the determination of the "percentage of identity" except for the fact that in the calculation also homologous positions and not only identical positions are considered. Two homologous amino acids have two identical or homologous amino acids. Homologous amino acid residues have similar chemical-physical properties, for example, amino acids belonging to a same group: aromatic (Phe, Trp, Tyr), acid (Glu, Asp), polar (Gln, Asn), basic (Lys, Arg, His), aliphatic (Ala, Leu, Ile, Val), with a hydroxyl group (Ser, Thr), or with a short lateral chain (Gly, Ala, Ser, Thr, Met). It is expected that substitutions between such homologous amino acids do not change a protein phenotype (conservative substitutions).

A gB is "homologous" or a "homolog" if it has an identity to SEQ ID NO: 1 of at least 70%, 80%, 85%, 90%, 95%, 96%, 97%, 98%, 99%, or 100%, if it has an amino acid homology to SEQ ID NO: 1 of at least 50%, 60%, 70%, 80%, 85%, 90%, 95%, or 100%, or if it has the same activity as the gB according to SEQ ID NO: 1. Preferably, "same activity" may be understood in the sense that gB binds to a cellular receptor, and more preferably, during the entry process of the virus into a cell, gB undergoes a conformational change promoting fusion of the virus with the membrane of the cell, and still more preferably, it acts as a fusogen. A homolog may also be a fragment of a full length gB having the activity as indicated above.

The chimeric gB of the present invention (as exemplified by SEQ ID NO: 2) carries a heterologous polypeptide ligand and thereby confers a new activity on the virus, in addition to the activity that the gB portion carries out for the wildtype (wt) virus. The chimeric gB, once it is part of the envelope of the recombinant virus, enables the binding of the recombinant virus to the target molecule, and retargets the tropism of recombinant virus to a cell carrying the target molecule of the ligand.

Preferably, the chimeric gB undergoes a conformational change promoting fusion of the virus with the membrane of the cell, and still more preferably, the chimeric gB acts as a fusogen. After fusion with a cell carrying the target molecule of the ligand, the recombinant herpesvirus enters the cell, and the cell infected by the recombinant herpesvirus produces proteins encoded by the viral genome, including the chimeric gB harboring the heterologous polypeptide ligand. The infected cell produces progeny virus which lyses the cell, thereby killing it.

The term "retargeting", as used herein, means that the recombinant herpesvirus of the present invention is targeted to the target molecule of the ligand. However, the recombinant herpesvirus is still capable of being targeted to the natural receptor of the unmodified herpesvirus. Retargeting is different from "detargeting", which means that the recombinant herpesvirus is no longer capable of being targeted to the natural receptor of the unmodified herpesvirus. "Detargeting" means that the recombinant virus is only targeted to the target molecule of the ligand.

The indication of a specific amino acid number or region of gB, as used herein, refers to the "precursor" form of gB, as exemplified in SEQ ID NO: 1 that includes the N-terminal signal sequence comprising the first 30 amino acids. The "mature" form of gB starts with amino acid 31 of SEQ ID NO: 1 and extends until amino acid 904. As gB glycoproteins with amino acid sequences different from SEQ ID NO: 1 are also comprised by the present invention, the indication of a specific amino acid number or of a specific amino acid region which relates to SEQ ID NO: 1 means also the amino acid number or region of a homologous gB, which corresponds to the respective amino acid number or region of SEQ ID NO: 1.

The term "recombinant" herpesvirus, as referred to herein, refers to a herpesvirus that has been genetically engineered by genetic recombination to include additional nucleic acid sequences which encode the heterologous polypeptide. Methods of producing recombinant herpesviruses are well known in the art (see for example Sandri-Goldin et al., 2006). However, the present invention is not limited to genetic engineering methods. Also other methods may be used for producing an herpesvirus having fused or inserted a heterologous polypeptide ligand to or into gB, respectively.

The term "chimeric glycoprotein B" or "chimeric gB", or "chimeric gB", as used herein, means a gB having fused to or inserted into the gB a heterologous polypeptide ligand. The chimeric gB is encoded by the recombinant virus, is synthesized with the cell that produces the recombinant virus, and becomes incorporated in the envelope of the virion. Methods to produce the recombinant viruses by genetic engineering are known in the art. Methods for producing chimeric glycoprotein B are known in the art.

The term "herpesvirus", as referred to herein, refers to a member of the Herpesviridae family of double-stranded DNA viruses, which cause latent or lytic infections. Herpesviruses all share a common structure in that their genomes consist of relatively large (about from 100.000 to 200.000 base pairs), double-stranded, linear DNA encoding 80 to 200 genes, encased within an icosahedral protein cage called the capsid which is itself wrapped by a protein layer called the tegument containing both viral proteins and viral mRNAs and a lipid bilayer membrane called the envelope. This whole particle is also known as a virion. The term "herpesvirus" also refers to members of the Herpesviridae family which are mutated comprising one or more mutated genes, such as, e.g., herpesviruses which were modified in a laboratory.

In a preferred embodiment, the herpesvirus is selected from the group consisting of Herpes Simplex Virus 1 (HSV-1), Herpes Simplex Virus 2 (HSV-2), Varicella Zoster Virus (human herpesvirus 3 (HHV-3)), swine alphaherpesvirus Pseudorabiesvirus (PRV), Chimpanzee alpha1 herpesvirus (ChHV), Papiine herpesvirus 2 (HVP2), Cercopithecine herpesvirus 2 (CeHV2), Macacine herpesvirus 1 (MHV1), Saimiriine herpesvirus 1 (HVS1), Callitrichine herpesvirus 3 (CalHV3), Saimiriine herpesvirus 2 (HVS2), Bovine herpesvirus 1 (BoHV-1), Bovine Herpesvirus 5 (BoHV-5), Equine herpesvirus 1 (EHV-1), Equine herpesvirus 2 (EHV-2), Equine herpesvirus 5 (EHV-5), Canine herpesvirus 1 (CHV), Feline herpesvirus 1 (FHV-1), Duck enteritis virus (DEV), Fruit bat alphaherpesvirus 1 (FBAHV1), Bovine herpesvirus 2 (BoHV-2), Leporid herpesvirus 4 (LHV-4), Equine herpesvirus 3 (EHV-3), Equine herpesvirus 4 (EHV-4), Equine herpesvirus 8 (EHV-8), Equid herpesvirus 9 (EHV-9), Cercopithecine herpesvirus 9 (CeHV-9), Suid herpesvirus 1 (SuHV-1), Marek's disease virus (MDV), Marek's disease virus serotype 2 (MDV2), Falconid herpesvirus type 1 (FaHV-1), Gallid herpesvirus 3 (GaHV-3), Gallid herpesvirus 2 (GaHV-2), Lung-eye-trachea disease-associated herpesvirus (LETV), Gallid herpesvirus 1 (GaHV-1), Psittacid herpesvirus 1 (PsHV-1), Human herpesvirus 8 (HHV-8), Human herpesvirus 4 (HHV-4), Chelonid herpesvirus 5 (ChHV5), Ateline herpesvirus 3 (AtHV3) or Meleagrid herpesvirus 1 (MeHV-1). In a more preferred embodiment, the herpesvirus is HSV-1 or HSV-2, most preferably HSV-1.

The term "heterologous", as used herein, refers to a polypeptide that is not encoded by the herpesvirus genome, or that of any other herpesvirus. Preferably, the term "heterologous" refers to a polypeptide which binds to a cell which carries a target molecule of the ligand and is to be infected by the recombinant herpesvirus of the present invention. The heterologous polypeptide may be a natural polypeptide, or part thereof, or an artificial polypeptide, not found in nature.

The term "polypeptide", as used herein, is a continuous and unbranched peptide chain consisting of amino acids connected by peptide bonds. The length of the polypeptide chain is unlimited and may range from some amino acids such as 5 amino acids to some hundreds or thousands amino acids. In the present invention, a polypeptide may be used as a ligand or as a target molecule. The length of the chain depends on the molecule which is the starting molecule for the ligand or target molecule. More than one polypeptide chains may assemble to a complex such as an antibody. The term "polypeptide", as used herein, also comprises an assembly of polypeptide chains. The term "peptide", as used herein, is a short polypeptide chain, usually consisting of less than about 50 amino acid residues, preferably less than about 40 amino acids residues, or more preferably of between about 10 and about 30 amino acids. The minimum length is 5 amino acid residues.

The term "corresponding region of a homologous gB" refers to a region of a gB which aligns with a given region of the gB according to SEQ ID NO: 1 when using the Smith-Waterman algorithm and the following alignment parameters: MATRIX: BLOSUM62, GAP OPEN: 10, GAP EXTEND: 0.5. This algorithm is generally known and used in the art if performing pairwise sequence comparisons and the skilled person knows how to apply it. In case only a part or parts of the given region of SEQ ID NO: 1 aligns with the sequence of a homologous gB using above algorithm and parameters, the term "corresponding region" refers to the region which aligns with the part(s) of the given region of SEQ ID NO: 1. In this case, the region in the homologous gB, in which the ligand is inserted, comprises only the amino acids which align with the part(s) of the given region of SEQ ID NO: 1. The term "corresponding region" may also refer to a region which is flanked by corresponding flanking sequences, wherein the flanking sequences align, using above algorithm and parameters, with sequences flanking the region of SEQ ID NO: 1. These flanking sequences are at least 5, 6, 7, 8, 9, 10, 15, 20, 30, 40 or 50 amino acids long. Other algorithms which may be used are the algorithms of Needleman and Wunsch, 1970, the similarity method of Pearson and Lipman, 1988, or the algorithm of Karlin and Altschul, 1990, modified by Karlin and Altschul, 1993, or computerized implementations of these algorithms.

The term "corresponding amino acid" refers to an amino acid which is present within a corresponding region and which is the counterpart of a given amino acid of SEQ ID NO: 1 in the alignment. A corresponding amino acid must not be identical to its counterpart in SEQ ID NO: 1 in the alignment, as far as it is present within a corresponding region.

A ligand, as referred to herein, binds or is capable of binding to a target molecule accessible on the surface of a cell. Preferably, it specifically binds or is capable of specifically binding to a target molecule accessible on the surface of a cell, whereby the term "specifically binds" refers to a binding reaction wherein the ligand binds to a particular target molecule of interest, whereas it does not bind in a substantial amount (less than 10%) to other molecules present on cells or to other molecules to which the ligand may come in contact in an organism. Generally, a ligand that "specifically binds" a target molecule has an equilibrium affinity constant greater than about $10^5$ (e.g., $10^6$, $10^7$, $10^8$, $10^9$, $10^{10}$, $10^{11}$, $10^{12}$ or more) mole/liter for that target molecule. Preferably, the ligand mediates the capability that the virus fuses with the cell, so that more preferably the virus then enters the cell, and still more preferably kills the cell. It is understood that the ligand is not harmful to humans. Moreover, the ligand is not a herpesvirus protein or is not derived by modification from a herpesvirus protein.

The ligand may be a natural or artificial polypeptide ligand which is capable of specifically binding to a target molecule which is accessible on a cell, preferably wherein the heterologous polypeptide ligand is capable of binding to a target molecule present on a cell present in cell culture or to a target molecule present on a diseased cell. Natural polypeptide ligands are natural polypeptides that are capable of binding to a target molecule. Thus, the ligand may be the natural ligand of a natural target molecule such as a receptor molecule, which is accessible on a cell. Examples of such a ligand may be a cytokine, a chemokine, an immune checkpoint blocker, or a growth factor. Known examples are EGF and IL13. Alternatively, the ligand is an antibody that binds to a target molecule. Still alternatively, the ligand is a natural polypeptide which has been selected to bind to an artificial target molecule, whereby the target molecule is designed to be capable of binding to the ligand. The natural polypeptide may be derived from any organism, preferably from an organism which is not harmful to human. For example, the natural polypeptide is a fungal or bacterial polypeptide, such as a polypeptide from the genus *Saccharomyces* such as *Saccharomyces cerevisiae*. An example of a natural polypeptide is the GCN4 yeast transcription factor. Artificial polypeptide ligands have non-naturally occurring amino acid sequences that function to bind a particular target molecule. The sequence of the artificial polypeptide ligand may be derived from a natural polypeptide which is modified, including insertion, deletion, replacement and/or addition of amino acids, whereby the binding capability of the corresponding natural polypeptide is retained. For example, the ligand may be a part of a natural polypeptide, as referred to above, as far as said part is capable of binding to the target molecule to which the corresponding full-length polypeptide binds. Alternatively, the natural polypeptide has been modified to comprise an amino acid identity to the corresponding natural polypeptide of at least 70%, 80%, 85%, 90%, 95%, 96%, 97%, 98% or 99%, whereby the modified polypeptide retains the activity of the corresponding natural polypeptide, such as binding to the target molecule. Still alternatively, the artificial polypeptide ligand may have 274 amino acid residues or less, preferably less than 200 amino acid residues, more preferably less than 50 amino acid residues, still more preferably less than 40 amino acids residues, or still more preferably between 10 and 30 amino acids, most preferably 20 amino acids, such as a part of a natural polypeptide or a peptide from a (random) peptide library. Still alternatively, the polypeptide is an antibody derivative or an antibody mimetic that binds to the target molecule. The antibody, antibody derivative or antibody mimetic may be mono-specific (i.e. specific to one target molecule accessible on the surface of a cell) or multi-specific (i.e. specific to more than one target molecule accessible on the surface of the same or a different cell), for example bi-specific or tri-specific (e.g., Castoldi et al., 2013, Castoldi et al., 2012). Specificity of the virus is increased by simultaneously targeting more than one target molecule on the same cell. If more than one target molecule present on different cells are targeted, tumor heterogeneity can be addressed.

The term "antibody derivative", as referred to herein, refers to a molecule comprising at least one antibody variable domain, but not comprising the overall structure of an antibody. The antibody derivative is still capable of binding a target molecule. Preferably, the antibody derivative mediates the capability that the virus fuses with the cell, so that more preferably the virus then enters the cell, and still more preferably kills the cell. Said derivatives may be antibody fragments such as Fab, Fab2, scFv, Fv, or parts thereof, or other derivatives or combinations of immunoglobulins such as nanobodies, diabodies, minibodies, camelid single domain antibodies, single domains or Fab fragments, domains of the heavy and light chains of the variable region (such as Fd, VL, including Vlambda and Vkappa, VH, VHH) as well as mini-domains consisting of two beta-strands of an immunoglobulin domain connected by at least two structural loops. Preferably, the antibody derivative is a single chain antibody, more preferably scFv which is a fusion protein of the variable regions of the heavy ($V_H$) and light chains ($V_L$) of immunoglobulins, connected with a short linker peptide. The N-terminus of $V_H$ is either connected with the C-terminus of $V_L$ or the N-terminus of $V_L$ is connected with the C-terminus of $V_H$.

The term "antibody mimetic", as referred to herein, refers to organic compounds that, like antibodies, can specifically bind antigens, but that are not structurally related to antibodies. They are usually artificial peptides or proteins with a molar mass of about 3 to 20 kDa. They may have therapeutic or diagnostic effects. Non-limiting examples of antibody mimetics are affibodies, affilins, affimers, affitins, anticalins, avimers, DARPins, fynomers, Kunitz domain peptides, monobodies, Z domain of Protein A, Gamma B crystalline, ubiquitin, cystatin, Sac7D from *Sulfolobus acidocaldarius*, lipocalin, A domain of a membrane receptor, ankyrin repeat motive, SH3 domain of Fyn, Kunits domain of protease inhibitors, the $10^{th}$ type III domain of fibronectin, synthetic heterobivalent or heteromultivalent ligands (Josan et al., 2011, Xu et al., 2012, Shallal et al., 2014).

The term "a heterologous polypeptide ligand" or "a ligand", as referred to herein, includes one or more than one ligand(s) such as 2, 3, or 4 ligands. This means that the recombinant herpesvirus may comprise one ligand or may comprise more than one ligand. The presence of one ligand allows the targeting of one target cell type. If more than one ligand is present, the ligands may be fused to or inserted into one gB being located in the gB molecule on different sites or on the same site, i.e. successively, or the ligands may be fused to or inserted into different gBs. Alternatively, if more than one ligand are present, the second or further ligand(s) may be comprised by a glycoprotein of the herpesvirus other than gB, such as gD and/or gH. The different ligands may target different target molecules present on the same target cell or on different target cells, preferably on different target cells. In analogy to the above, the term "a target molecule", as referred to herein, includes one or more than one target molecule(s) such as 2, 3, or 4 target molecules. Consequently, the recombinant herpesvirus may bind to one target cell or may bind to more than one target cells such as 2, 3, or 4 different cells.

In a preferred embodiment of the present invention, the heterologous polypeptide ligand is an artificial polypeptide, preferably an scFv, which is capable of binding to a natural receptor on a diseased cell, preferably a tumor cell, more preferably a tumor cell expressing HER2, such as a breast cancer cell, ovary cancer cell, stomach cancer cell, lung cancer cell, head and neck cancer cell, osteosarcoma cell, glioblastoma multiforme cell, or salivary gland tumor cell. In a more preferred embodiment, the heterologous polypeptide ligand is scFv capable of binding to HER2. In the most preferred embodiment, the heterologous polypeptide ligand is scFv as identified by SEQ ID NO: 32.

In an additionally or alternatively preferred embodiment of the present invention, the heterologous polypeptide ligand is an artificial polypeptide, preferably a part of a natural polypeptide, which is capable of binding to an artificial target molecule present on a cell present in cell culture. The length of the ligand is more preferably less than about 50 amino acid residues, still more preferably less than about 40 amino acids residues, still more preferably of between about 10 and about 30 amino acids, or most preferably 20 amino acids. The ligand and target molecules are specifically constructed to bind to each other. More preferred, the heterologous polypeptide ligand is a part of the GCN4 yeast transcription factor. Still more preferred, the heterologous polypeptide ligand is the part of the GCN4 yeast transcription factor as comprised by SEQ ID NO: 37, most preferably, the ligand is the molecule identified by the sequence of SEQ ID NO: 37. In an alternative embodiment, the ligand may be the molecule identified by the sequence of SEQ ID NO: 38.

In a more preferred embodiment of the present invention, the preferred and alternatively preferred embodiment, as mentioned above, are combined. Namely, the recombinant herpesvirus of the present invention simultaneously comprises two heterologous polypeptide ligands, one being capable of binding to a diseased cell and one being capable of binding to a cell present in cell culture.

The GCN4 yeast transcription factor used as a polypeptide ligand fused to or inserted into gB is state of the art (see e.g. Arndt and Fin, 1986; Hope and Struhl, 1987). An exemplary GCN4 yeast transcription factor is one identified by SEQ ID NO: 43 (UniProtKB—P03069 (GCN_YEAST), as encoded by AJ585687.1 (SEQ ID NO: 42). The term "GCN4 yeast transcription factor", as referred to herein, refers to any GCN4 yeast transcription factor present in nature. Alternatively, GCN4 yeast transcription factor, as referred to herein, refers to any GCN4 yeast transcription factor which has an amino acid identity to the sequence of SEQ ID NO: 43 of at least 70%, 80%, 85%, 90%, 95%, 96%, 97%, 98%, 99% or 100%. Alternatively, the GCN4 yeast transcription factor, as referred to herein, refers to any GCN4 yeast transcription factor which has an amino acid homology to SEQ ID NO: 43 of at least 50%, 60%, 70%, 80%, 85%, 90%, 95%, or 100%. A GCN4 yeast transcription factor is "homologous" or a "homolog" if it has an identity to SEQ ID NO: 43 of at least 70%, 80%, 85%, 90%, 95%, 96%, 97%, 98%, 99%, or 100%, if it has an amino acid homology to SEQ ID NO: 43 of at least 50%, 60%, 70%, 80%, 85%, 90%, 95%, or 100%, or if it has the same activity as the GCN4 yeast transcription factor according to SEQ ID NO: 43. Preferably, "same activity" may be understood in the sense that GCN4 yeast transcription factor works as a transcription factor in the same way as the GCN4 yeast transcription factor according to SEQ ID NO: 43. The term "part thereof" comprises any part of the GCN4 yeast transcription factor against which a target molecule can be generated to which the "part thereof" is capable of binding. Preferably, the length of "the part thereof" is thus that a ligand length of 274 amino acids or less, preferably less than 200 amino acid residues, more preferably less than 50 amino acids residues, still more preferably less than 40 amino acids residues, still more preferably between 10 and 30 amino acids, or still more preferably 20 amino acids results, whereby the ligand may include additional sequences such as linker sequences.

The most preferred "part thereof" is the sequence YHLENEVARLKK (SEQ ID NO: 38) of GCN4 yeast transcription factor to which two flanking wt (wildtype) GCN4 residues may be added on each side. For fusion to or insertion into gB, a GS linker may be additionally present on each side of the peptide. This construct is herein named GCN4 peptide (SEQ ID NO: 37). This 20 amino acid peptide confers to the herpesvirus the ability to infect and replicate in a cell line bearing a target molecule to which the "part thereof" binds.

In the recombinant herpesvirus of the present invention, the ligand may be fused to or inserted into gB, between amino acids 43 and 44 of gB, corresponding to amino acids 13 and 14 of mature gB (SEQ ID NO: 2). In this context, the term "fused" or "fusion", as referred to herein, refers to the addition of the polypeptide ligand to the N-terminal amino acid of gB by peptide bonds, either directly or indirectly via a peptide linker. "Fused" or "fusion" to the N-terminal region is different from "insertion" insofar as "fused" or "fusion" means addition to the terminus of gB, whereas "insertion" means incorporation into the gB.

A peptide linker, as referred to herein, serves to connect, within a polypeptide, polypeptide sequences derived from different sources. Such a linker serves to connect and to enable proper folding of the heterologous polypeptide ligand with glycoprotein B sequences or to connect ligand portions within the heterologous polypeptide ligand. It may also serve to connect ligand sequences with glycoprotein sequences other than gB. A linker has typically a length between 1 and 30 amino acids, preferably 5 to 25 amino acids, more preferably 8 to 20 amino acids, such as 8, 12 or 20 amino acids and may comprise any amino acids. Preferably, it comprises the amino acid(s) Gly and/or Ser and/or Thr, more preferably it comprises at least 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 amino acids selected from the group consisting of Gly, Ser and/or Thr. Most preferably, it consists of the amino acids Gly and/or Ser. Linkers based on Gly and/or Ser provide flexibility, good solubility and resistance to proteolysis. Alternatively, the linker may not predominantly comprise glycine, serine and/or threonine, but glycine, serine and/or threonine may not be present or only to a minor extent.

In the recombinant herpesvirus of the present invention, the ligand may be alternatively inserted at any amino acid within a disordered region of gB, whereby the ligand is not inserted at any amino acid within the region spanning from amino acids 77 to 88 of gB according to SEQ ID NO: 1 or a corresponding region of a homologous gB. However, a ligand of short length not exceeding 120 amino acids may be inserted within the region spanning from amino acids 77 to 88 of gB according to SEQ ID NO: 1 or a corresponding region of a homologous gB. As referred to herein, disordered region is meant to comprise a region which lacks a fixed tertiary structure, is unstructured, and consequently not amenable to being resolved in a crystal structure. Often, disordered regions are extended, i.e. random coil like, or collapsed, i.e. molten globule like. Disordered structures in gB are referred to in Gallagher et al., 2014, Heldwein et al., 2006, and Lin et al., 2007 and may be present in the N-terminal region (extending from amino acids 31 to 108), in a central region (extending from amino acids 460 to 491) and the C-terminal region (extending from amino acids 796 to 904) (Heldwein et al., 2006) of HSV gB. Positions which are mentioned as being disordered are amino acids 31 to 108 (N-terminal region) (Lin et al., 2007), amino acids 460 to 491 (central region) (Heldwein et al., 2006) and amino acids 796 to 904 (C-terminal region) (Heldwein et al., 2006, Lin et al. 2007) of HSV-1 gB. Preferably, the ligand is inserted at any amino acids within a region spanning from amino acids 31 to 108 or 460 to 491 of gB according to SEQ ID NO: 1 or a corresponding region of a homologous gB. The ligand is not inserted within the region spanning from amino acids 77 to 88 of gB according to SEQ ID NO: 1 or a corresponding region of a homologous gB. However, a ligand of short length not exceeding 120 amino acids may be inserted within the region spanning from amino acids 77 to 88 of gB according to SEQ ID NO: 1 or a corresponding region of a homologous gB.

The ligand may be alternatively inserted at any amino acid within a region spanning from amino acids 31 to 77 or 88 to 184, preferably amino acids 31 to 77 or 88 to 136 or more preferably 31 to 77 or 88 to 108, or into a region spanning from amino acids 409 to 545, preferably amino acids 459 to 545, more preferably amino acids 459 to 497, or still more preferably amino acid 460 to 491, of gB according to SEQ ID NO: 1 or within a corresponding region of a homologous gB. Moreover, a ligand of short length not exceeding 120 amino acids may be inserted within the region spanning from amino acids 77 to 88 of gB according to SEQ ID NO: 1 or a corresponding region of a homologous gB. These regions include amino acids which are located within disordered regions of gB, however, also include amino acids which are located in the neighborhood of disordered regions. The regions, as indicated above, have been found to accept polypeptide insertions, thereby maintaining the capability of gB to function as a fusogen mediating membrane fusions of cells carrying gB and the receptor (Gallagher et al., 2014; Lin and Spear, 2007; Potel et al., 2002).

The term "inserted" or "insertion", as referred to herein in the sense that a ligand is inserted into gB, refers to the incorporation of the polypeptide ligand into the gB, wherein the incorporated polypeptide is introduced between two amino acids of the gB by peptide bonds, either directly or indirectly via one or more peptide linkers, more specifically via an upstream and/or downstream located peptide linker with respect to the insert. The linker is directly connected to the polypeptide ligand. The fusion of a polypeptide ligand to gB can also be seen as an insertion of the polypeptide ligand sequence into the gB precursor, exemplified by SEQ ID NO: 1 or a homologous gB, directly before amino acid 1 of the gB; such an insertion is herein termed as fusion. The gB carrying the fused, or inserted polypeptide is herein referred to as chimeric gB. The chimeric gB is part of the virion envelope. The definition of "linker" is, as described above.

The insertion and fusion are preferably carried out by genetic engineering of the gB gene, in the genome of HSV. The genetic engineering of HSV genomes is known in the art, exemplified by, but not limited to, BAC technologies The present inventors have found that insertion of a heterologous polypeptide ligand at an amino acid within the region of amino acids 77 to 88 of the gB, as exemplified by SEQ ID NO: 3, in which the scFv to HER2 is inserted between amino acids 81 to 82, does not result in the retargeting of the recombinant herpesvirus to cells carrying the receptor of the ligand. The present inventors believe that the reason for this lack of retargeting is the presence of a proline-rich region (PPPPXP) and a predicted N-glycosylation site (NAT) within this region. As proline disrupts protein secondary structure and/or imposes its own kind of secondary structure with a confined phi angle that overrides other forms of secondary structure (Morgan and Rubistein, 2013)), and as polyproline helices can induce sharp turns in the local geometry, the polyproline stretch in this region may have constrained the conformation adopted by the ligand. In addition, the N-glycosylation site in this region may have shielded the ligand. Consequently, the ligand may not be sufficiently available for interaction with its receptor on a cell surface. Moreover, the present inventors have also found that insertion of a heterologous polypeptide ligand at any amino acid within the region spanning from amino acids 77 to 88 of the gB results in the retargeting of the recombinant herpesvirus to cells carrying the receptor of the ligand, if the heterologous polypeptide ligand is of short length. Thus, the present invention provides a recombinant herpesvirus comprising a heterologous polypeptide ligand capable of binding to a target molecule and inserted into glycoprotein B (gB) present in the envelope of the herpesvirus, wherein the ligand is of short length and is inserted at any amino acid within a region spanning from amino acids 77 to 88 of gB according to SEQ ID NO: 1 or within a corresponding region of a homologous gB. "Short length" means a length which does not exceed 120 amino acids, such as 5 to 120 amino acids, 5 to 110, 5 to 100, 5 to 90, 5 to 80, 5 to 70, 5 to 60, 5 to 50, 5 to 40, 5 to 30, 5 to 25, 10 to 30, 10 to 20, 20 or 12 amino acids. Preferably, the ligand has a length of 10 to 30 amino acids, more preferably the ligand has a length of 12 to 20 amino acids, still more preferably the ligand is 12 or 20 amino acids. Insertion may be at any amino acid between amino acids 77 to 88, such as behind amino acid 77, 78, 79, 80, 81, 82, 83, 84, 85, 86, or 87. Preferably, the ligand is inserted between amino acids 81 and 82. Any of a combination of a ligand of a length as indicated above inserted behind any of the amino acids mentioned above results in the retargeting of the herpesvirus to the target molecule of the ligand. Preferably, the heterologous polypeptide ligand may be a part of a natural polypeptide capable of binding to a target molecule present on a cell present in cell culture, such as a part of the GCN4 yeast transcription factor, such as the part of the GCN4 yeast transcription factor as comprised by SEQ ID NO: 37. Most preferably, the ligand is the molecule identified by the sequence of SEQ ID NO: 37. Such a ligand may be inserted at any amino acid within the region spanning from amino acids 77 to 88, preferably between amino acids 81 to 82. Most preferably, the ligand is the molecule identified by the sequence of SEQ ID NO: 37 inserted between amino acids 81 and 82 of gB. The amino acid numbers refer to SEQ ID NO: 1 or corresponding amino acids of a homologus gB.

As used herein, the target molecule may be any molecule which is accessible on the surface of a cell and which can be bound by the heterologous polypeptide ligand. The target molecule may be a natural molecule such as a polypeptide or protein, a glycolipid or a glycoside. For example, the target molecule may be a receptor, such as a protein receptor. A receptor is a molecule embedded in a membrane of a cell that receives chemical signals from the outside via binding of a ligand, causing some form of a cellular response. Alternatively, the target molecule may be a molecule that is a drug target, such as enzymes, transporters or ion-channels, present on the surface of a cell. Preferably, the target molecule is present on a diseased cell or on a cell present in cell culture. Preferred target molecules are those which are naturally present on diseased cells of an organism, such as mentioned below, in a specific or abnormal manner. "Specific manner" may be understood in the sense that the target molecule is overexpressed on the diseased cell, whereas it is not or only to a minor extent, i.e. to an extent to which it is usually present on a respective normal cell, expressed on the normal cell. "Abnormal manner" may be understood in the sense that the target molecule is present on a diseased cell in a mutated form, as compared to the respective molecule of the respective non-diseased cell. Therefore, retargeting a herpesvirus to a target molecule, such as a specifically expressed or mutated target molecule, results in a higher infection and eradication rate of a cell carrying the target molecule as compared to a cell that does not carry the target molecule or carries the target molecule at a lower level or carries the wildtype (non-mutated) target molecule.

Alternatively, the target molecule may be an artificial molecule. The term "artificial target molecule", as referred to herein, is a molecule that does not naturally occur, i. e. that has a non-natural amino acid sequence. Such artificial molecule may be constructed to be expressed by a cell on its surface, as e.g. described in Douglas et al., 1999; and Nakamura et al., 2005 or it may be bound by a cell surface. Artificial target molecules have non-naturally occurring amino acid sequences that function to bind a particular ligand. Examples of artificial target molecules are antibody derivatives, or antibody mimetics. Artificial target molecules are preferably present on the surface of a cell present in cell culture which may be used for producing the recombinant herpesvirus. Preferred artificial target molecules present on a cell present in cell culture are scFvs. In the context of artificial target molecule, antibodies are comprised by the term "artificial target molecule" which may be present on a cell present in cell culture by which they are not naturally produced.

In a preferred embodiment, the target molecule is a tumor-associated receptor, preferably a member of the EGF receptor family, including HER2, EGFR, EGFRIII or EGFR3 (ERBB3), EGFRvIII, MET, FAP, PSMA, CXCR4, CEA, CADC, Mucins, Folate-binding protein, GD2, VEGF receptors 1 and 2, CD20, CD30, CD33, CD52, CD55, the integrin family, IGF1R, the Ephrin receptor family, the protein-tyrosine kinase (TK) family, RANKL, TRAILR1, TRAILR2, IL13Ralpha, UPAR, Tenascin, PD-1, PD-L1, CTL-A4, and additional members of the immune checkpoint family regulators, tumor-associated glycoprotein 72, ganglioside GM2, A33, Lewis Y antigen, or MUC1, most preferably HER2. Preferably, the target molecule is HER2 which is overexpressed by some tumor cells such as breast cancer cells, ovary cancer cells, stomach cancer cells, lung cancer cells, head and neck cancer cells, osteosarcoma cells, glioblastoma multiforme cells, or salivary gland tumor cells, but is expressed at very low levels in non-malignant tissues. A tumor-associated receptor is a receptor which is expressed by a tumor cell in a specific or abnormal manner. Alternatively, the target molecule is a molecule derived from an infectious agent such as a pathogen (e.g. a virus, bacterium or parasite) that has infected a cell. The target molecule is expressed on the surface of the infected cell (such as HBsAg from HBV, gpI20 from HIV, E1 or E2 from HCV, LMP1 or LMP2 from EBV). The pathogen may result in an infectious disease, such as a chronic infectious disease. Still alternatively, the target molecule is expressed by a degenerative disorder-associated cell or by a senescent cell such as CXCR2 or the IL-1 receptor. In another preferred embodiment, the target molecule is an antibody derivative, more preferably an scFv, still more preferably an scFv capable of binding to a part of the GCN4 yeast transcription factor, still more preferably an scFv capable of binding to the part of the GCN4 yeast transcription factor as comprised by SEQ ID NO: 37, still more preferably the scFv as comprised by SEQ ID NO: 39, most preferably the molecule identified by the sequence of SEQ ID NO: 41.

The term "cell", as referred to herein, is any cell which carries a target molecule and which can be infected by the recombinant herpesvirus of the present invention. The cell may be a naturally occurring cell which is unwanted and shall be eliminated, such as a diseased cell. Examples of diseased cells are given below. Preferred diseased cells are those comprising HER2. Alternatively, the cell may be a cell which serves to produce the recombinant herpesvirus. Such cell may be any cell which can be infected by the recombinant herpesvirus of the present invention and which can produce the herpesvirus. Moreover, propagation of the herpesvirus shall be avoided in diseased cells, so as to avoid the introduction of material such as DNA, RNA and/or protein of diseased cells such as tumor cells in humans, Therefore, the cell for producing the herpesvirus is a cell which is not harmful if present in humans, e.g. a non-diseased cell. The cell may be present as a cell line. For producing the recombinant herpesvirus, the cell is present in cell culture. Therefore, a cell which serves to produce the recombinant herpesvirus is termed herein "cell present in cell culture". Thus, the cell may be a cultured cell suitable for growth of herpesvirus, preferably the cell is a cell line approved for herpesvirus growth. Examples of such cells are Vero, 293, 293T, HEp-2, HeLa, BHK, or RS cells, preferably Vero cells. Preferably, the cell present in cell culture has been modified to express a target molecule which is not naturally expressed by the corresponding parent cell or the cell present in cell culture has been modified and binds the target molecule on its surface. More preferably, the cell comprises as the target molecule an antibody derivative, still more preferably an scFv, still more preferably an scFv capable of binding to a part of the GCN4 yeast transcription factor, still more preferably an scFv capable of binding to the part of the GCN4 yeast transcription factor as comprised by SEQ ID NO: 37, still more preferably the scFv as comprised by SEQ ID NO: 39, most preferably the molecule identified by the sequence of SEQ ID NO: 41.

A "cultured" cell is a cell which is present in an in vitro cell culture which is maintained and propagated, as known in the art. Cultured cells are grown under controlled conditions, generally outside of their natural environment. Usually, cultured cells are derived from multicellular eukaryotes, especially animal cells. "A cell line approved for growth of herpesvirus" is meant to include any cell line which has been already shown that it can be infected by a herpesvirus, i. e. the virus enters the cell and is able to propagate and produce the virus. A cell line is a population of cells descended from a single cell and containing the same genetic composition. Preferred cells for propagation and production of the recombinant herpesvirus are Vero, 293, 293T, HEp-2, HeLa, BHK, or RS cells.

The term "diseased cell", as used herein, refers to a cell which negatively influences an organism and is, therefore, not wanted. The eradication of such a cell is desired, as its killing may be live-saving or enhances the health of an organism. In a preferred embodiment, the diseased cell is characterized by an abnormal growth, more preferably the cell is a tumor cell. In an alternative preferred embodiment, the cell is an infected cell such as a chronically infected cell, a degenerative disorder-associated cell or a senescent cell.

In case of a tumor cell, the underlying disease is a tumor, preferably selected from the group consisting of adrenal cancer, anal cancer, bile duct cancer, bladder cancer, bone cancer, brain/CNS tumors, breast cancer, cancer of unknown primary treatment, Castleman disease, cervical cancer, colon/rectum cancer, endometrial cancer, esophagus cancer, Ewing family of tumors, eye cancer, gallbladder cancer, gastrointestinal carcinoid tumors, gastrointestinal stromal tumor (gist), gestational trophoblastic disease, Hodgkin disease, Kaposi sarcoma, kidney cancer, laryngeal and hypopharyngeal cancer, leukemia, liver cancer, lung cancer, lymphoma, lymphoma of the skin, malignant mesothelioma, multiple myeloma, myelodysplastic syndrome, nasal cavity and paranasal sinus cancer, nasopharyngeal cancer, neuroblastoma, non-Hodgkin lymphoma, oral cavity and oropharyngeal cancer, osteosarcoma, ovarian cancer, pancreatic cancer, penile cancer, pituitary tumors, prostate cancer, retinoblastoma, rhabdomyosarcoma, salivary gland cancer, sarcoma—adult soft tissue cancer, skin cancer, small intestine cancer, stomach cancer, testicular cancer, thymus cancer, thyroid cancer, uterine sarcoma, vaginal cancer, vulvar cancer, Waldnstrom macroglobulinemia, and Wilms tumor. Preferred tumor diseases are HER2-positive cancers (like breast cancer, ovary cancer, stomach cancer, lung cancer, head and neck cancer, osteosarcoma and glioblastoma multiforme), EGFR-positive cancers (like head and neck cancer, glioblastoma multiforme, non-small cell lung cancer, breast cancer, colorectal and pancreatic cancer), EGFR-vIII-positive cancers (like glioblastoma multiforme), PSMA-positive cancers (like prostate cancer), CD20+ positive lymphoma, and EBV related tumors such as B-cell lymphoproliferative disorders such as Burkitt's lymphoma, classic Hodgkin's lymphoma, and lymphomas arising in immunocompromised individuals (post-transplant and HIV-associated lymphoproliferative disorders), T-cell lymphoproliferative disorders, angioimmunoblastic T-cell lymphoma, extranodal nasal type natural killer/T-cell lymphoma.

In case of an infected cell, the underlying disease is an infectious disease, such as a chronic infectious disease, wherein the infectious agent may be a virus, a bacterium or a parasite. Examples are tuberculosis, malaria, chronic viral hepatitis (HBV, Hepatitis D virus and HCV), acquired immune deficiency syndrome (AIDS, caused by HIV, human immunodeficiency virus), EBV related disorders, or HCMV related disorders.

In case of a degenerative disorder-associated cell, the underlying disease may be Alzheimer's disease, amyotrophic lateral sclerosis (ALS), Lou Gehrig's Disease, osteoarthritis, atherosclerosis, Charcot Marie Tooth disease (CMT), chronic obstructive pulmonary disease (COPD), chronic traumatic encephalopathy, diabetes, ehlers-danlos syndrome, essential tremor, Friedreich's ataxia, huntington's disease, inflammatory bowel disease (IBD), keratoconus, keratoglobus, macular degeneration, marfan's syndrome, multiple sclerosis, multiple system atrophy, muscular dystrophy, Niemann Pick disease, osteoporosis, Parkinson's Disease, progressive supranuclear palsy, prostatitis, retinitis pigmentosa, rheumatoid arthritis, or Tay-Sachs disease. The term "degenerative disorder-associated cell" refers to a cell which is in relationship with the disorder, meaning that an alteration of the cell contributes to the development of the disease or the cell is altered as a consequence of the disease. Destroying the cell results in the treatment of the disease.

In case of a senescent cell, the underlying disease is a senescence-associated disease, such as (i) rare genetic diseases called progeroid syndromes, characterized by premature aging: Werner syndrome (WS), Bloom syndrome (BS), Rothmund-Thomson syndrome (RTS), Cockayne syndrome (CS), xeroderma pigmentosum (XP), trichothiodystrophy or Hutchinson-Gilford Progeria syndrome (HGPS) or (ii) common age related disorders, such as obesity, type 2 diabetes, sarcopenia, osteoarthritis, idiopathic pulmonary fibrosis, chronic obstructive pulmonary disease, cataracts, neurodegenerative diseases, systemic autoimmune diseases (systemic lupus erythematosus, rheumatoid arthritis, or Sjögren syndrome), or multiple sclerosis.

The recombinant herpesvirus of the present invention may, in addition to the chimeric gB, comprise a modified gD glycoprotein, as disclosed in WO 2009/144755, but not limited to those types of modifications. A modified gD may carry a deletion of the amino acid portion 6 to 38 of mature gD (as exemplified by SEQ ID NO: 5; an exemplary gD wildtype precursor sequence is indicated in SEQ ID NO: 4). Alternatively, a modified gD may carry other modifications that detarget herpesvirus tropism from the natural receptors Nectin-1 and HVEM. gD may, alternatively or in addition to the modifications that detarget herpesvirus tropism, encode additional sequences that readdress the tropism of the herpesvirus to selected receptors of choice, which are receptors on diseased cells such as the HER2 receptor, as described in recombinant R-LM113 (SEQ ID NO: 6). Modification of gD occurs by fusing to or inserting into gD the heterologous polypeptide ligands, as defined herein. The recombinant herpesvirus of the present invention may, in addition to the chimeric gB, comprise a modified gH glycoprotein, capable to retarget gH to a target receptor molecule, comprising the heterologous polypeptide ligands, as defined herein. The recombinant herpesvirus of the present invention may, in addition to the chimeric gB, comprise a modified gD and a modified gH glycoprotein, as disclosed in Gatta et al., 2015, but not limited to those descriptions. Both documents are herein incorporated by reference. The modification(s) of gD and/or gH serve(s) for readdressing the tropism of the herpesvirus to diseased cells, as defined herein.

Thus, in an embodiment of the present invention, the recombinant herpesvirus of the present invention comprises a chimeric gB comprising a ligand which binds to a target molecule accessible on a cell such as a diseased cell, e.g. a cell expressing HER2, or a cell present in cell culture, and a modified gD, whereby the modification may be a deletion of amino acids 6 to 38. The gD may alternatively or in addition be modified by the insertion of a heterologous polypeptide ligand, as defined herein, capable of retargeting the herpesvirus to a diseased cell. Additionally or alternatively, the recombinant herpesvirus may comprise a modified gH which comprises a heterologous polypeptide ligand, as defined herein, capable of retargeting the herpesvirus to a diseased cell.

Moreover, the present inventors have found that deletion of amino acids 30 to 38 or a subset thereof from gD with regard to mature gD according to SEQ ID NO: 62 or a corresponding region of a homologous gD results in a recombinant herpesvirus that is detargeted from the natural receptor of unmodified gD. Thus, in an embodiment of the present invention, the recombinant herpesvirus comprises a heterologous polypeptide ligand as defined herein fused to or inserted into gB as defined herein and retargeted to the target molecule of the ligand and a gD, wherefrom amino acids 30 to 38 or a subset thereof of a gD with regard to mature gD according to SEQ ID NO: 62 or a corresponding region of a homologous gD, preferably amino acids 30 and/or 38, more preferably amino acids 30 and 38 are deleted, with regard to mature gD according to SEQ ID NO: 62 or a corresponding region of a homologous gD.

Instead of deleted amino acids 30 to 38 or a subset thereof a heterologous polypeptide ligand, as defined herein, may be inserted, resulting in the detargeting of the recombinant herpesvirus from the natural receptor of unmodified gD and retargeting to the target molecule of the ligand. In addition to the replacement of a subset by a heterologous polypeptide ligand, an additional amino acid or range of amino acids within amino acids 30 to 38 may be deleted. Thus, in a preferred embodiment amino acids 30 and 38 are deleted and a heterologous polypeptide ligand is inserted instead of amino acid 30 or 38. More preferably, amino acids 30 and 38 are deleted and a heterologous polypeptide ligand is inserted instead of amino acid 38.

The term "subset thereof" means one amino acid or at least 2, such as 2, 3, 4, 5, 6, 7, or 8 adjacent amino acids out of the region consisting of amino acids 30 to 38. Thus, "subset thereof" may mean amino acids 30, 31, 32, 33, 34, 35, 36, 37, or 38, 30 to 31, 30 to 32, 30 to 33, 30 to 34, 30 to 35, 30 to 36, 30 to 37, 30 to 38, 31 to 32, 31 to 33, 31 to 34, 31 to 35, 31 to 36, 31 to 37, 31 to 38, 32 to 33, 32 to 34, 32 to 35, 32 to 36, 32 to 37, 32 to 38, 33 to 34, 33 to 35, 33 to 36, 33 to 37, 33 to 38, 34 to 35, 34 to 36, 34 to 37, 34 to 38, 35 to 36, 35 to 37, 35 to 38, 36 to 37, 36 to 38, 37 to 38. The term "subset" may comprise one or more subsets, such as 2, 3, 4, or 5 subsets. For example, "subset" may comprise amino acid 30 and amino acid 38, the deletion thereof resulting in a gD that does not comprise amino acids 30 and 38. Deletion of a subset, or the whole of amino acids 30 to 38, results in the inactivation of the nectin-1 binding site of gD reducing the binding capability of gD to nectin-1 and/or in the inactivation of the HVEM binding site of gD reducing the binding capability of gD to HVEM. For example, if amino acid 30 is deleted, the HVEM binding site of gD is inactivated, while the deletion of amino acid 38 results in the inactivation of the nectin-1 binding site. Deletion of both amino acids 30 and 38 results in the inactivation of the HVEM binding site and the nectin-1 binding site.

The heterologous polypeptide ligand, inserted instead of amino acids 30 to 38 or a subset thereof, may be a ligand capable of binding to a target molecule present on a diseased cell, preferably an scFv capable of binding to a target molecule present on a cancer cell, such as a breast cancer cell, ovary cancer cell, stomach cancer cell, lung cancer cell, head and neck cancer cell, osteosarcoma cell, glioblastoma multiforme cell, or salivary gland tumor cell, such as HER2, more preferably an scFv identified by SEQ ID NO: 32, whereby the target molecule is HER2 present on a tumor cell expressing the HER2.

In a particularly preferred embodiment of the present invention, a heterologous polypeptide ligand capable of binding to a target molecule present on a cell present in cell culture is inserted into gB between amino acids 43 to 44 and a heterologous polypeptide ligand capable of binding to a target molecule present on a diseased cell is inserted instead of amino acid 38 of gD from which furthermore amino acid 30 is deleted. Most preferably, the heterologous polypeptide ligand capable of binding to a target molecule present on a cell present in cell culture comprises the sequence identified by SEQ ID NO: 37, the target molecule is the molecule with the sequence identified by SEQ ID NO: 41, and the cell present in cell culture expresses the molecule identified by the sequence of SEQ ID NO: 41, and the heterologous polypeptide ligand capable of binding to a target molecule present on a diseased cell comprises an scFv identified by SEQ ID NO: 32, the target molecule is HER2, and the cell is a tumor cell expressing HER2, preferably a breast cancer cell, ovary cancer cell, stomach cancer cell, lung cancer cell, head and neck cancer cell, osteosarcoma cell, glioblastoma multiforme cell, or salivary gland tumor cell.

Moreover, disclosed is a recombinant herpesvirus comprising a gD, wherefrom amino acids 30 to 38 or a subset thereof with regard to mature gD according to SEQ ID NO: 62 or a corresponding region or corresponding amino acids of a homologous gD, preferably amino acids 30 and/or 38, more preferably amino acids 30 and 38 are deleted. Instead of deleted amino acids 30 to 38 or a subset thereof a heterologous polypeptide ligand, as defined herein, may be inserted, resulting in the detargeting of the recombinant herpesvirus from the natural receptor of unmodified gD and retargeting to the target molecule of the ligand. In addition to the replacement of a deleted amino acid or range of deleted amino acids by a heterologous polypeptide ligand, an additional amino acid or range of amino acids within amino acids 30 to 38 may be deleted. Thus, for example amino acids 30 and 38 are deleted and a heterologous polypeptide ligand is inserted instead of amino acid 30 or 38. For example, amino acids 30 and 38 are deleted and a heterologous polypeptide ligand is inserted instead of amino acid 38.

The amino acid numbers with respect to gD refer to mature gD according to SEQ ID NO: 62 or corresponding amino acids of a homologous gD. Thus, amino acid 30 with regard to mature gD according to SEQ ID NO: 62 corresponds to amino acid 55 and amino acid 38 with regard to mature gD according to SEQ ID NO: 62 corresponds to amino acid 63 according to SEQ ID NO: 4 (precursor form). The amino acid numbers with respect to gB refer to gB according to SEQ ID NO: 1 (precursor form) or corresponding amino acids of a homologous gB.

gD homologs are found in some members of the alpha subfamily of Herpesviridae. Therefore, the term "homologous gD", as referred to herein, refers to any gD homolog found in the gD-encoding members of Herpesviridae. Alternatively, homologous gD, as referred to herein, refers to any gD, precursor or mature, which has an amino acid identity to the sequence of SEQ ID NO: 4 or 62, respectively, of at least 70%, 80%, 85%, 90%, 95%, 96%, 97%, 98%, 99% or 100%. Alternatively, homologous gD, as referred to herein, refers to any gD, precursor or mature, which has an amino acid homology to SEQ ID NO: 4 or 62, respectively, of at least 50%, 60%, 70%, 80%, 85%, 90%, 95%, or 100%. The homologous gD, as referred to herein, also includes a fragment of gD. Preferably, homologous gD, as referred to herein, including any gD found in Herpesviridae, any gD, precursor or mature, having an amino acid identity or homology, as defined above, to the sequence of SEQ ID NO: 4 or 62, respectively, and any fragment of a gD, has the same activity of the gD according to SEQ ID NO: 4 or 62. More preferably, during the entry process of the virus into a cell, gD binds to one of its receptors, thereby still more preferably interacting with the gH/gL heterodimer, which still more preferably results in dislodging the profusion domain of gD.

The recombinant herpesvirus of the present invention may, furthermore, encode one or more molecule(s) that stimulate(s) the host immune response against a cell, preferably a diseased cell, as defined above. A molecule that stimulates the host immune response is also termed "immunotherapy molecule". Thus, the recombinant herpesvirus of the present invention may be a combined oncolytic and immunotherapeutic virus. An immunotherapeutic virus is a virus that encodes molecules that boost the host immune response to a cell, i.e. that stimulate the host immune response so as to be directed against a cell. An example of such a virus is T-VEC (Liu et al., 2003).

Immunotherapy molecules, in addition to the chimeric gB, enable the recombinant virus, besides the specific targeting and killing of a cell via the heterologous polypeptide ligand, to stimulate a subject's immune system in a specific or unspecific manner. Expression of immunotherapy molecules by the recombinant virus in a subject can induce an immune response which finally results in the killing of diseased cells. Immunotherapy may act specifically wherein the immunotherapy molecules stimulate the subject's immune system against one or some specific antigen(s) present on (a) cell(s). For example, an immunotherapy molecule may be an antibody which is directed against a specific cell surface receptor, e.g.

CD20, CD274, and CD279. Once bound to an antigen, antibodies can induce antibody-dependent cell-mediated cytotoxicity, activate the complement system, or prevent a receptor from interacting with its ligand. All that can lead to cell death. Preferred cells are tumor cells. This technique is known and approved in the art. There are multiple antibodies which are approved to treat cancer, including Alemtuzumab, Ipilimumab, Nivolumab, Ofatumumab, and Rituximab. Alternatively, the immunotherapy molecule can act non-specifically by stimulating the subject's immune system. Examples of immunotherapy molecules are inter alias cytokines, chemokines or immune checkpoint regulators. For example, some cytokines have the ability to enhance anti-tumor activity and can be used as passive cancer treatments. The use of cytokines as immunotherapy molecules is known in the art. Examples of cytokines are GM-CSF, interleukin-2, interleukin-12, or interferon-$\alpha$. GM-CSF is used, for example in the treatment of hormone-refractory prostate cancer or leukemia. Interleukin-2 is used, for example, in the treatment of malignant melanoma and renal cell carcinoma. IL-12 is used in the experimental treatment of glioblastoma. Interferon-$\alpha$ is, for example, used in the treatment of hairy-cell leukemia, AIDS-related Kaposi's sarcoma, follicular lymphoma, chronic myeloid leukemia and malignant melanoma.

The recombinant herpesvirus of the present invention may be attenuated, for example by deletions in or alterations of genes known to attenuate virus virulence, such as the viral genes $\gamma_1 34.5$, UL39, and/or ICP47. The term "attenuated" refers to a weakened or less virulent herpesvirus. Preferred is a conditional attenuation, wherein the attenuation affects only non-diseased cells. More preferred, only the diseased cells such as tumor cells are affected by the full virulence of the herpesvirus. A conditional attenuation can be achieved, for example, by the substitution of the promoter region of the $\gamma_1 34.5$, UL39 and/or ICP47 gene with a promoter of a human gene that is exclusively expressed in diseased cells (e.g. the survivin promoter in tumor cells). Further modifications for a conditional attenuation may include the substitution of regulatory regions responsible for the transcription of IE genes (immediate early genes) like the ICP-4 promoter region with promoter regions of genes exclusively expressed in diseased cells (e.g. the survivin promoter). This change will result in a replication conditional HSV, which is able to replicate in diseased cells but not in normal cells. Additional modification of the virus may include the insertion of sequence elements responsive to microRNAs (miRs), which are abundant in normal but not tumor cells, into the 3' untranslated region of essential HSV genes like ICP4. The result will be again a virus that is replication incompetent only in normal cells.

In a second aspect, the present invention provides a pharmaceutical composition comprising the recombinant herpesvirus of the present invention and a pharmaceutically acceptable carrier, optionally additionally comprising one or more molecule(s) that stimulate(s) the host immune response against a cell, preferably a diseased cell, as defined above. The recombinant herpesvirus of the present invention can be used as a medicament. For the production of the medicament the herpesvirus has to be in a pharmaceutical dosage form comprising the recombinant herpesvirus of the present invention and a mixture of ingredients such as pharmaceutically acceptable carriers which provide desirable characteristics. The pharmaceutical composition comprises one or more suitable pharmaceutically acceptable carrier which is/are known to those skilled in the art.

The pharmaceutical composition may additionally comprise one or more molecule(s) that stimulate(s) the host immune response against a cell. The definition of the one or more molecule(s) that stimulate(s) the host immune response against a cell is referred to above under the first aspect of the present invention.

The pharmaceutical composition can be manufactured for systemic, nasal, parenteral, vaginal, topic, vaginal, intratumoral administration. Parental administration includes subcutaneous, intracutaneous, intramuscular, intravenous or intraperitoneal administration.

The pharmaceutical composition can be formulated as various dosage forms including solid dosage forms for oral administration such as capsules, tablets, pills, powders and granules, liquid dosage forms for oral administration such as pharmaceutically acceptable emulsions, microemulsions, solutions, suspensions, syrups and elixirs, injectable preparations, for example, sterile injectable aqueous or oleaginous suspensions, compositions for rectal or vaginal administration, preferably suppositories, and dosage forms for topical or transdermal administration such as ointments, pastes, creams, lotions, gels, powders, solutions, sprays, inhalants or patches.

The specific therapeutically effective dose level for any particular subject will depend upon a variety of factors including the activity of the recombinant herpesvirus of the present invention, the dosage form, the age, body weight and sex of the subject, the duration of the treatment and like factors well known in the medical arts.

The total dose of the compounds of this invention administered to a subject in single or in multiple doses may be in amounts, for example, from $10^3$ to $10^{10}$.

Single dose compositions may contain such amounts or submultiples thereof to make up the daily dose. The dosages of the recombinant herpesvirus may be defined as the number of plaque forming unit (pfu). Examples of dosages include $10^3$, $10^4$, $10^5$, $10^6$, $10^7$, $10^8$, $10^9$, or $10^{10}$.

The recombinant herpesvirus of the present invention serves to treat diseases in which diseased cells express specific target molecules on their surface, so that they are accessible from the outside of the cell, which target molecules are not produced by a normal cell or are produced by the normal cell to a lower degree. The normal cell may be the respective normal cell. "Respective" means that the diseased and normal cells are of the same origin, however, cells develop into diseased cells due to disease-generating influences, whereas other cells of same origin remain healthy.

In a third aspect, the present invention provides the recombinant herpesvirus of the present invention, optionally in combination with one or more molecule(s) that stimulate (s) the host immune response against a cell, preferably a diseased cell, as defined above, for use in the treatment of a tumor, infection, degenerative disorder or senescence-associated disease. The recombinant herpesvirus of the present invention and the molecule that stimulates the host immune response against a cell can be present within the same pharmaceutical composition or within different pharmaceutical compositions. If they are present in different pharmaceutical compositions, they may be administered simultaneously, or subsequently, either the herpesvirus before the molecule or the molecule before the herpesvirus. The herpesvirus or the molecule may be administered at different frequencies and/or time points. However, a combined treatment comprises that the herpesvirus and the molecule are administered at time intervals and/or time points that allow the simultaneous treatment of the disease.

The present invention also discloses a method of treating a subject having a tumor, infection, degenerative disorder or senescence-associated disorder by administering a pharmaceutically effective amount of the recombinant herpesvirus of the present invention.

The recombinant herpesvirus of the present invention may be administered to a subject in combination with further treatments which stimulate the host immune response against a cell, preferably a diseased cell, and/or serve to treat the specific disease of the subject. Such further treatments may include other drugs, chemotherapy, radiotherapy, immunotherapy, combined virotherapy, etc.

The present invention also discloses the use of the herpesvirus of the present invention, optionally in combination with one or more molecule(s) that stimulate(s) the host immune response against a cell, preferably a diseased cell, as defined above, for the preparation of a pharmaceutical composition for the treatment of a tumor, infection, degenerative disorder or senescence-associated disease.

The subjects which are treated by the recombinant herpesvirus of the present invention are preferably humans.

In a fourth aspect, the present invention provides a nucleic acid molecule comprising a nucleic acid coding for the chimeric gB of the present invention having fused or inserted the ligand. The nucleic acid molecule may be the genome of the recombinant herpesvirus of the present invention or a part thereof. Preferably, the nucleic acid molecule encodes the precursor form of the chimeric gB including the signal sequence of the gB glycoprotein. If the chimeric gB was engineered to harbor the ligand to its N-terminal amino acid, the corresponding nucleic acid has the nucleic acid sequence of the ligand inserted between the last amino acid of the signal sequence and the first amino acid of the mature protein.

In a fifth aspect, the present invention provides a vector comprising the nucleic acid molecule. Suitable vectors are known in the art and include plasmids, cosmids, artificial chromosomes (e.g. bacterial, yeast or human), bacteriophages, viral vectors (retroviruses, lentiviruses, adenoviruses, adeno-associated viruses), in particular baculovirus vector, or nano-engineered substances (e.g. ormosils). In one embodiment, the vector is modified, in particular by a deletion, insertion and/or mutation of one or more nucleic acid bases, such that its virulence is attenuated, preferably in case of a viral vector, or that it replicates conditionally in diseased cells but not in non-diseased cells. For example, deletion of one or both copies of the $\gamma_1 34.5$ gene, the UL39 gene, the ICP47 gene results in attenuation of the virus. Attenuation or attenuated refers to weakened or less virulent virus.

Moreover, the substitution of the promoter region of the $\gamma_1 34.5$ gene with a promoter of a human gene that is exclusively expressed in diseased cells, e.g. tumor cells (e.g. survivin promoter in tumor cells), which will result in an attenuated phenotype in non-diseased cells and non-attenuated phenotype in diseased cells, is included. Further modifications may include the substitution of regulatory regions responsible for the transcription of IE genes like the ICP-4 promoter region with promoters of genes exclusively expressed in diseased cells (e.g. survivin promoter). This change will produce a replication conditional herpesvirus, able to replicate in diseased cells but not in normal cells. Cell culture cells for propagation of the virus progeny will provide high levels of specific promoter activating proteins to allow for the production of high virus yields.

In a sixth aspect, the present invention provides a polypeptide comprising the chimeric gB having fused or inserted the ligand.

In a seventh aspect, the present invention provides a cell comprising the recombinant herpesvirus, the nucleic acid molecule comprising a nucleic acid coding for the chimeric gB of the present invention having fused or inserted the ligand, the vector comprising the nucleic acid molecule, or the polypeptide comprising the chimeric gB having fused or inserted the ligand. Preferably, the cell is a cell culture cell. Suitable cell cultures and culturing techniques are well known in the art (Peterson and Goyal, 1988).

In an eighth aspect, the present invention provides a method for infecting a cell using the recombinant herpesvirus of the present invention. The object of the present invention is the provision of a recombinant herpesvirus which infects a cell unwanted in a subject, propagates therein, lyses the cell and, thereby, kills the cell. The method for infecting also serves for growth of the recombinant herpesvirus in a cell present in cell culture. “Infecting” means that the virus enters the cell via fusion of the viral surface membrane with the cell membrane and viral components such as the viral genome are released into the cell. Methods of infecting a cell with a virus are known in the art, e.g. by incubating the virus with the cell to be infected (Florence et al., 1992; Peterson and Goyal, 1988). “Killing” means that the cell is totally eliminated due to the infection of the herpesvirus of the present invention, the production of viral particles within the cell and, finally, the release of the new viral particles by lysing the cell. Cells, for example in a cell culture, which carry the target molecule of the ligand on their surface can be used to test the lytic efficacy of the recombinant herpesvirus. For example, the cell may be a diseased cell obtained from a subject, for example a tumor cell. This cell is infected and thereby killed by the recombinant herpesvirus. The successful killing of the cell is indicative of the cell specificity of the recombinant herpesvirus, in order to evaluate the therapeutic success of eliminating cells such as tumor cells from the subject. In a further embodiment, also non-diseased cells may be obtained from the same subject or from a control subject not suffering from the disease, i.e. the cells do not carry the target molecule of the ligand on their surface or carry the target molecule to a lower extent. By this, it can be tested whether and/or to which extent the non-diseased cell is susceptible to infection by the recombinant herpesvirus. In another embodiment, diseased cells comprised in a population of cells (e.g. tissue such as blood) comprising non-diseased cells and diseased cells (for example tumor cells such as leukemia cells) are killed after isolation of the population of cells from a subject (e.g. leukapheresis). This serves to obtain a population of cells free of diseased cells, e.g. blood free of diseased cells such as leukemia cells, in particular for a later transplant of the population of cells into a subject, preferably into the same subject the population of cells was isolated from.

In case of blood and leukemia, for example, this method provides for re-infusion of blood free of tumor cells. The method for killing a cell using the recombinant herpesvirus of the present invention may be an in-vitro or in-vivo method.

In a ninth aspect, the present invention provides an in-vitro method for producing a recombinant herpesvirus in a cell present in cell culture using the herpesvirus according to any one of claims 1 to 9, preferably wherein the cell expresses or binds as a target molecule an artificial molecule, more preferably the target molecule comprises an antibody, an antibody derivative or an antibody mimetic, still more preferably an scFv, still more preferably an scFv capable of binding to a part of the GCN4 yeast transcription factor, still more preferably an scFv capable of binding to the part of the GCN4 yeast transcription factor as comprised by SEQ ID NO: 37, still more preferably the scFv as comprised by SEQ ID NO: 39, most preferably the molecule identified by the sequence of SEQ ID NO: 41.

The recombinant herpesvirus of the present invention serves the purpose of infecting and killing diseased cells in humans. This requires the provision of the herpesvirus and, therefore, its propagation and production. As propagation of the herpesvirus shall be avoided in diseased cells, so as to avoid the introduction of material such as DNA, RNA and/or protein of diseased cells such as tumor cells in humans, the recombinant herpesvirus has to be engineered to be capable of infecting also non-diseased cells. This requires the retargeting of the recombinant herpesvirus to diseased cells for killing and to non-diseased cells for propagation. Therefore, the ninth aspect of the present invention comprises the modification of the recombinant herpesvirus with more than one, such as 2, 3 or 4, preferably 2, heterologous polypeptide ligands. The ligands may be comprised by gB only, but may also be comprised by gB and gD and optionally by gH.

Consequently, in an embodiment of the ninth aspect, the recombinant herpesvirus comprises a heterologous polypeptide ligand, fused to or inserted into gB, capable of binding to a target molecule present on the cell present in cell culture and an additional heterologous polypeptide ligand fused to or inserted into gB, gD and/or gH, capable of binding to a target molecule present on a diseased cell. Preferably, the chimeric gB comprises a heterologous polypeptide ligand capable of binding to a target molecule present on the cell present in cell culture and a modified gD and/or gH comprise(s) a heterologous polypeptide ligand capable of binding to the target molecule present on a diseased cell.

Suitable techniques and conditions for growing herpesvirus in a cell are well known in the art (Florence et al., 1992; Peterson and Goyal, 1988) and include incubating the herpesvirus with the cell and recovering the herpesvirus from the medium of the infected cell culture. The cell by which the recombinant herpesvirus is produced carries a target molecule to which the recombinant herpesvirus binds via the heterologous polypeptide ligand. Preferably, the target molecule is an artificial target molecule. The artificial target molecule is specifically constructed to bind to the heterologous polypeptide ligand. Conversely, the ligand is specifically selected and constructed to bind to the artificial target molecule. Thus, the target molecule may be an antibody which is not naturally produced by the target cell, an antibody derivative or an antibody mimetic, preferably an scFv. The heterologous polypeptide ligand may be a natural polypeptide, preferably a fungal or bacterial polypeptide, such as a polypeptide from the genus *Saccharomyces* such as *Saccharomyces cerevisiae*, or an artificial polypeptide such as a part of the natural polypeptide capable of binding to the target molecule. The cell may be any cultured cell which is suitable for growth of herpesvirus. Preferably, the cell is a non-diseased cell. The cell may be present as a cell line or may be an isolated cell, preferably the cell is present as a cell line. The cell line may be approved for herpesvirus growth. Suitable cell lines are Vero, 293, 293T, HEp-2, HeLa, BHK, or RS cells, most preferably a Vero cell.

A "cultured" cell is a cell which is present in an in vitro cell culture which is maintained and propagated, as known in the art. Cultured cells are grown under controlled conditions, generally outside of their natural environment. Usually, cultured cells are derived from multicellular eukaryotes, especially animal cells. "A cell line approved for growth of herpesvirus" is meant to include any cell line which has been already shown that it can be infected by a herpesvirus, i. e. the virus enters the cell, and is able to propagate and produce the virus. A cell line is a population of cells descended from a single cell and containing the same genetic composition. Preferred cells for propagation and production of the recombinant herpesvirus are Vero, 293, 293T, HEp-2, HeLa, BHK, or RS cells.

In a preferred embodiment of the in-vitro method, the ligand is a part of a natural polypeptide and preferably has a length of 274 amino acid residues or less, preferably of less than 200 amino acid residues, more preferably of less than 50 amino acid residues, still more preferably less than 40 amino acids residues, and still more preferably of between t 10 and 30 amino acids such as 20 amino acids, whereby the part allows the construction of target molecules and the retargeting of the herpesvirus to a cell carrying the respective target molecule. The target molecule is an antibody derivative capable of binding to the part of the natural polypeptide. More preferably, the heterologous polypeptide ligand is a part of the GCN4 yeast transcription factor, the target molecule is an antibody derivative capable of binding to the ligand and the cell is a cell which has been modified to express the target molecule. Most preferably, the heterologous polypeptide ligand is the molecule identified by the sequence of SEQ ID NO: 37, the target molecule is the molecule identified by the sequence of SEQ ID NO: 41 and the cell is the Vero cell line which has been modified to express the molecule identified by the sequence of SEQ ID NO: 41, herein named Vero GCN4 cell line.

The Vero-GCN4 cell line expresses an artificial receptor being an scFv to the GCN4 peptide. The Vero-GCN4 cell line serves the purpose of enabling the cultivation of herpesvirus recombinants retargeted to HER2-positive cells, and detargeted from natural herpesvirus receptors. Because HER2 is an oncogene, and the HER2-positive cells are cancer cells, growth and production of oncolytic recombinant herpesvirus destined to human use in cancer cells should be avoided, in order to avoid the possible, accidental introduction of tumor-derived material (DNA, RNA, proteins) in humans. At the same time, the herpesvirus should be capable of infecting diseased cells. Therefore, the Vero-GCN4 cell line and an HER2-retargeted herpesvirus were constructed. The Vero-GCN4 cell line expresses an artificial receptor made of an scFv to the GCN4 peptide, fused to extracellular domains 2 and 3, transmembrane (TM) and C-tail of Nectin-1. The HER2 retargeted herpesvirus expresses the GCN4 peptide in gB. Consequently, the recombinant herpesvirus is simultaneously retargeted to HER2, in order to infect cancer cells, and to the GCN4 peptide, in order to infect the Vero-GCN4 cell line for virus growth and production.

In a particularly preferred embodiment of the ninth aspect, gB comprises a ligand capable of binding to a target molecule present on a cell present in cell culture, whereby the ligand may be an artificial polypeptide, more preferably a part of a natural polypeptide, and still more preferably a part of the GCN4 yeast transcription factor, and a modified gD and/or modified gH comprise(s) a ligand capable of binding to a target molecule present on a diseased cell, whereby the target molecule may be an antibody, an antibody derivative or an antibody mimetic, still more preferably an scFv, and still more preferably an scFv capable of binding to HER2. In the most preferred embodiment, the recombinant herpesvirus comprises a chimeric gB comprising the molecule identified by the sequence of SEQ ID NO: 37 and a modified gD and/or gH comprise(s) an scFv identified by SEQ ID NO: 32.

Such herpesvirus is capable of infecting the Vero-GCN4 cell line expressing the molecule identified by the sequence of SEQ ID NO: 41 for propagation and of infecting a tumor cell through HER2 present on the tumor cell for killing the tumor cell.

In another particularly preferred and most preferred embodiment, gB comprises a ligand capable of binding to a target molecule present on a diseased cell, and gD comprises a ligand capable of binding to a target molecule present on a cell present in cell culture. The definitions of ligand, target molecule and cell are as in the preceding chapter.

FIGURES

FIG. 1: Genome arrangements of recombinants R-BP901, R-BP903, R-BP909, R-313, R-315, R-317 and R-319. (A-G) The HSV-1 genome is represented as a line bracketed by internal repeats (IR). The Lox-P-bracketed BAC sequence and eGFP fluorescent marker are inserted in the intergenic region $U_L3$-$U_L4$. (A) R-BP903 carries the insertion of scFv-HER2, with a downstream 12 Ser-Gly linker, between AA 43-44 of gB. (B) R-BP909 is the same as R-BP903, but, in addition carries the deletion of AA 6-38 from mature gD for detargeting purpose. (C) R-BP901 carries the insertion of scFv-HER2, with a Ser-Gly linkers, between AA 81-82 of gB. (D) R-313 carries the insertion of GCN4 peptide, with one upstream and one downstream Ser-Gly linker, between AA 43-44 of immature gB and the scFv-HER2, with a downstream Ser-Gly, 11 amino acid long linker, in place of AA 6-38 of mature gD. E) R-315 carries the insertion of GCN4 peptide, with one upstream and one downstream Ser-Gly linker, between AA 81-82 of immature gB and the scFv-HER2, with a downstream Ser-Gly, 11 amino acid long linker, in place of AA 6-38 of mature gD. F) R-317 carries the insertion of GCN4 peptide, with one upstream and one downstream Ser-Gly linker, between AA 76-77 of immature gB and the scFv-HER2, with a downstream Ser-Gly, 11 amino acid long linker, in place of AA 6-38 of mature gD. G) R-319 carries the insertion of GCN4 peptide, with one upstream and one downstream Ser-Gly linker, between AA 95-96 of immature gB and the scFv-HER2, with a downstream Ser-Gly, 11 amino acid long linker, in place of AA 6-38 of mature gD.

Figure 2:
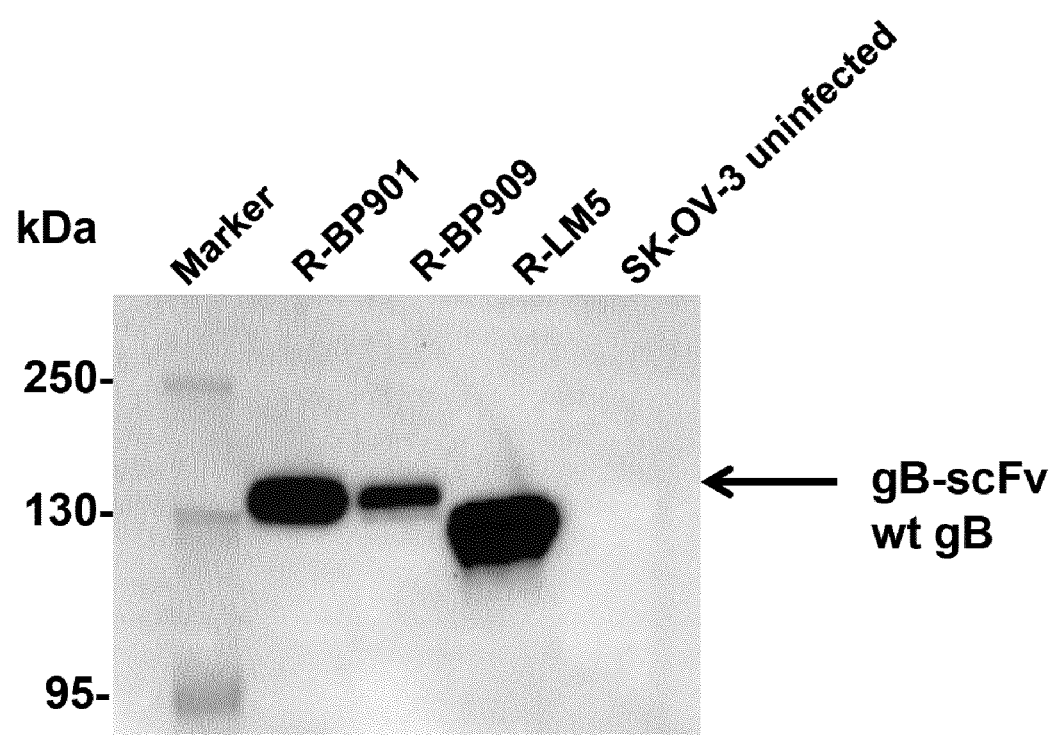

FIG. 2: R-BP901 and R-BP909 express the chimeric scFv-gB glycoprotein. Lysates of SK-OV-3 cells infected with R-BP901, R-BP909 or R-LM5, at an input multiplicity of infection of 3 PFU/cell were subjected to PAGE. gB was detected by immunoblot with MAb H1817. Numbers on the left represent the migration position of the 250 K, 130 K and 95 K MW markers.

Figure 3:
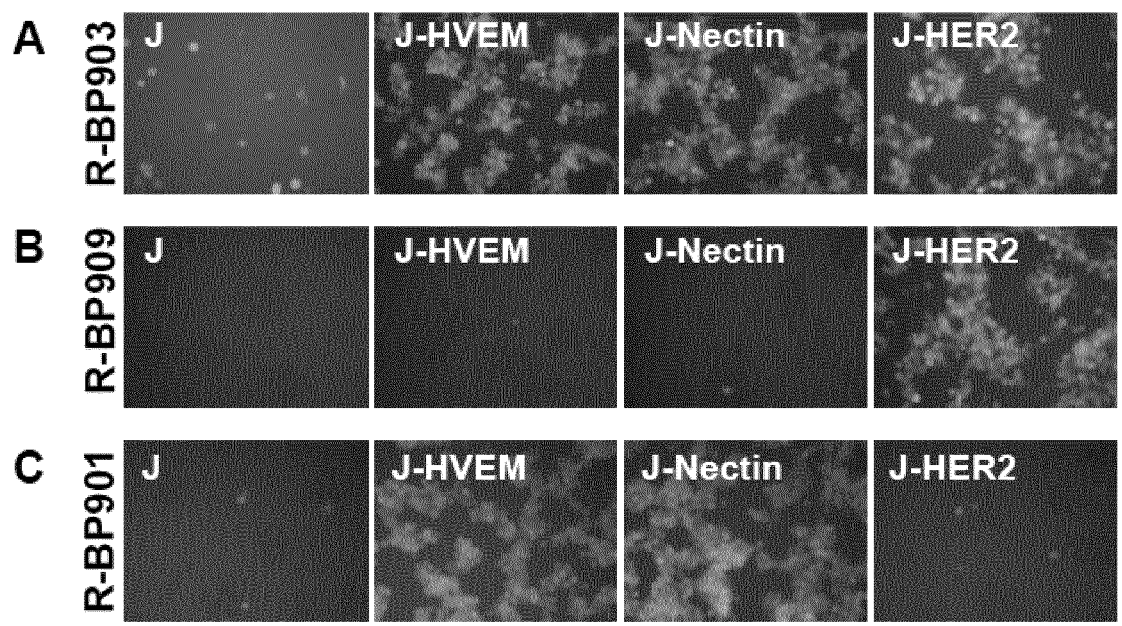

FIG. 3: Infection of J cells expressing single receptors with recombinants R-BP901, R-BP903 and R-BP909. J cells express no receptor for wt-HSV. J-HER2, J-Nectin1, J-HVEM only express the indicated receptor. The indicated cells were infected with R-BP903, R-BP909 and R-BP901 and monitored for green fluorescence microscopy 24 h post infection. (A) R-BP903 infected J-HER2 cells, as well as J-Nectin and J-HVEM, as expected given that this recombinant encodes a wt-gD. This virus is retargeted to HER2 and retains the natural tropism. (B) R-BP909 infects cells that express HER2 as the sole receptor (J-HER2) and fails to infect J-Nectin and J-HVEM, as a consequence of gD deletion of AA 6-38. R-BP909 is retargeted to HER2 and detargeted from HSV-1 gD natural receptors. (C) R-BP901 fails to infect J-HER2; this virus is not retargeted to HER2.

Figure 4:
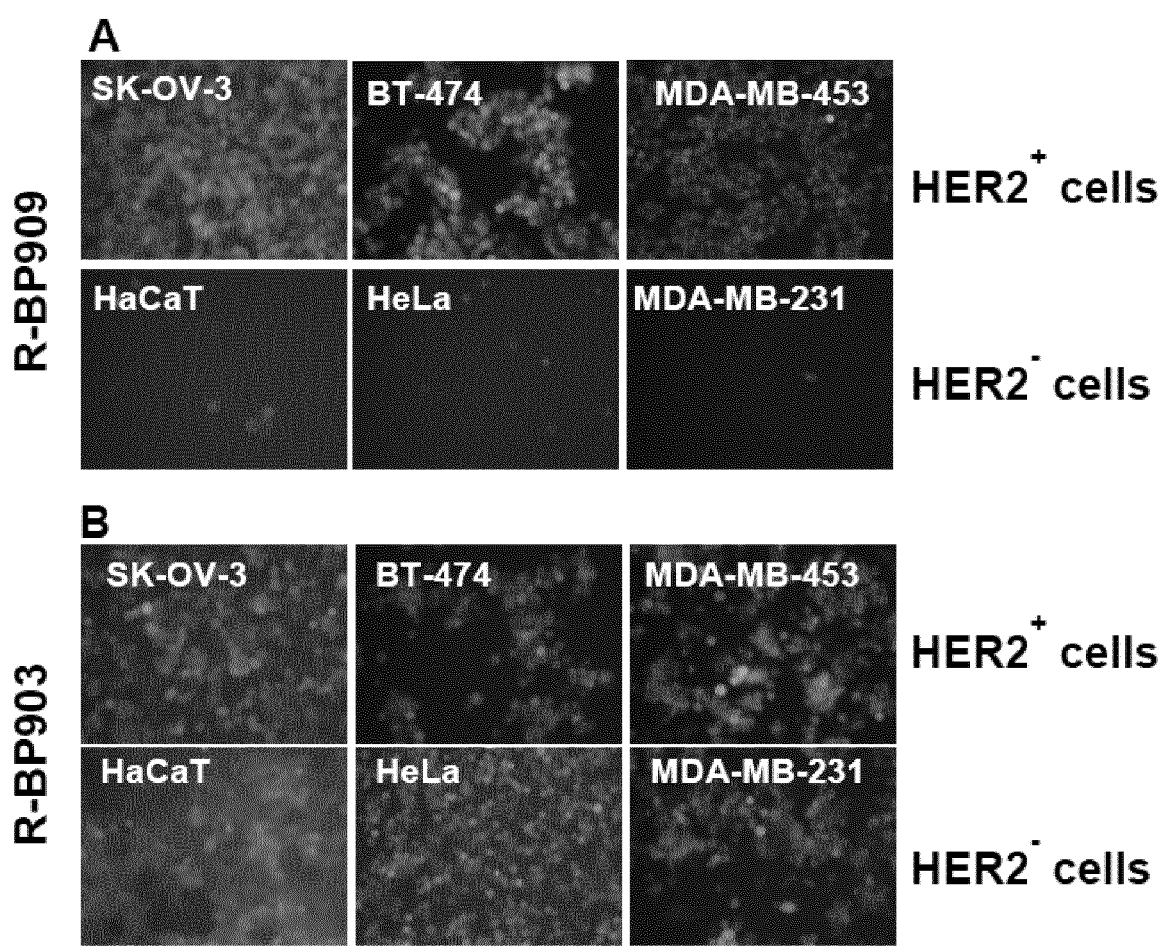

FIG. 4: R-BP909 specifically infects HER2$^+$ cancer cells. The indicated HER2$^-$ and HER2$^+$ cancer cell lines were infected with R-BP909 and R-BP903. Pictures were taken 24 h after infection at fluorescence microscope. R-BP909 infects the HER2-positive cancers cells and fails to infect the HER2-negative cancer cells. R-BP903 infects cells irrespective of the expression of HER2, in agreement with the lack of detargeting.

Figure 5:
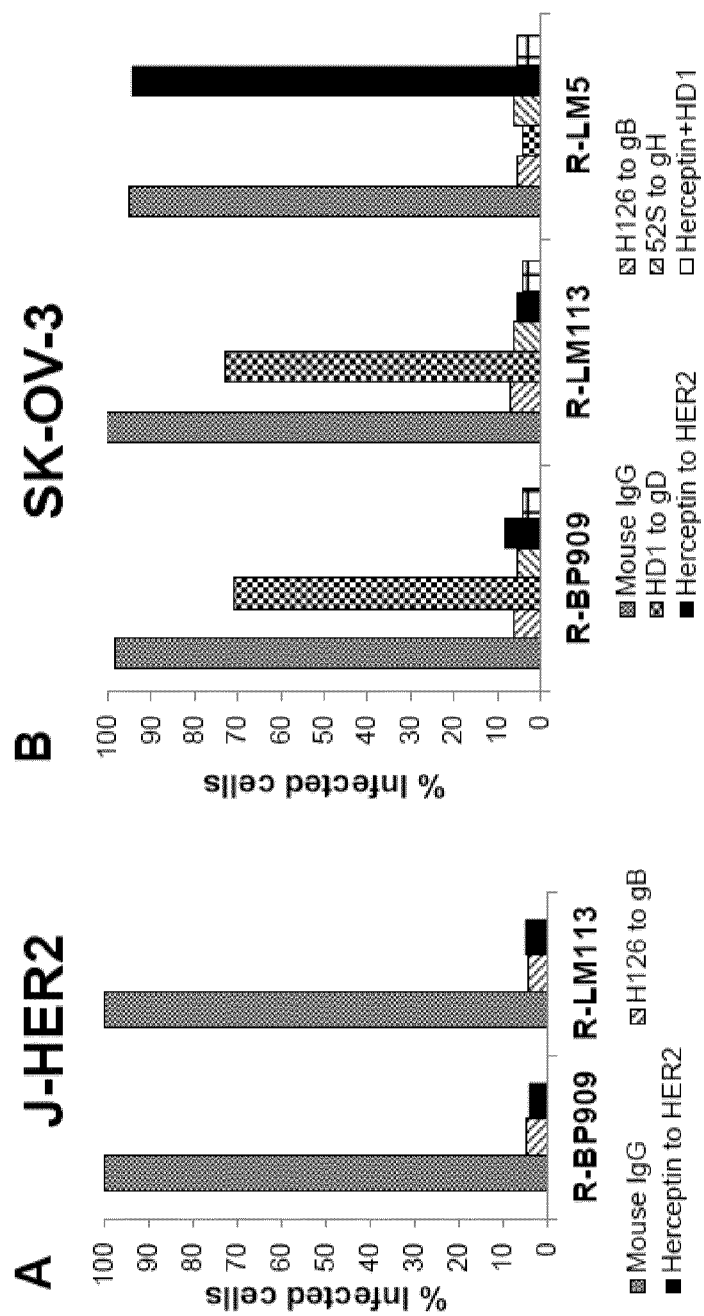

FIG. 5: Characterization of R-BP909 entry pathways in J-HER2 (A) and SK-OV-3 (B) cells. The indicated viruses were preincubated with HD1, 52S, H126 MAb and then allowed to infect J-HER2 or SK-OV-3 cells. When indicated, cells were pretreated with trastuzumab or control IgGs. Infection was quantified 24 h later by means of flow cytometry. (A) R-BP909 infection of J-HER2 cells is almost abolished by trastuzumab, and by MAb H126 to gB. (B) R-BP909 infection of SK-OV-3 cells is inhibited by trastuzumab and by MAb H126 to gB, 52S to gH, but not by MAb HD1 to gD. R-LM113, a recombinant retargeted to HER2 through insertion of scFv to HER2 in gD, behaved similarly to R-BP909.

Figure 6:
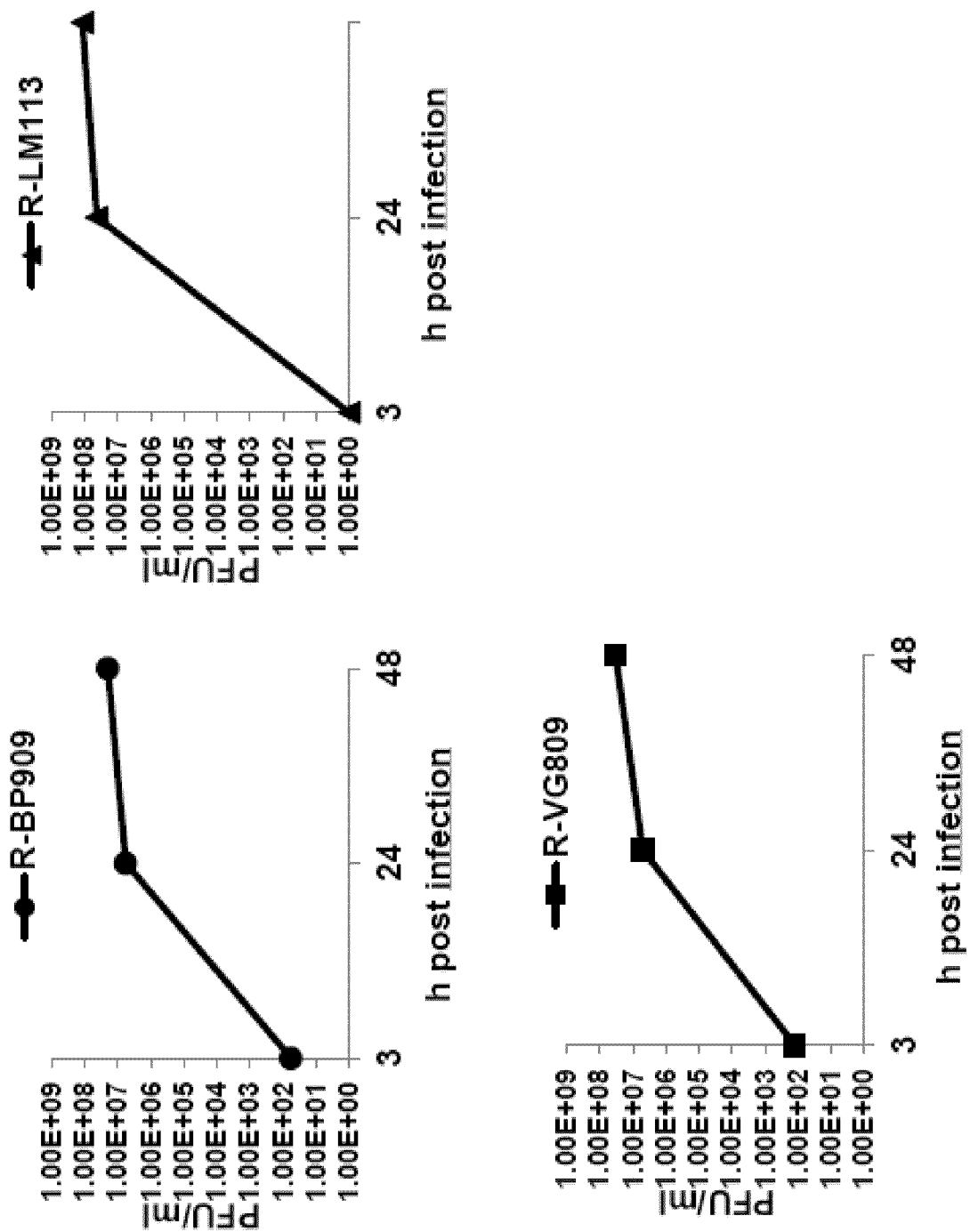

FIG. 6: Growth curves of R-BP909, and of the control recombinants R-VG809 (retargeted to HER2 through gH) and R-LM113 (retargeted to HER2 through gD). SK-OV-3 cells were infected with the indicated recombinants at an input multiplicity of infection of 0.1 PFU/cell and harvested at the indicated times (h) after infection. Progeny virus was titrated in SK-OV-3 cells. Growth curves indicate that R-BP909 replicated in a similar way to R-VG809, about one log less than R-LM113.

Figure 7:
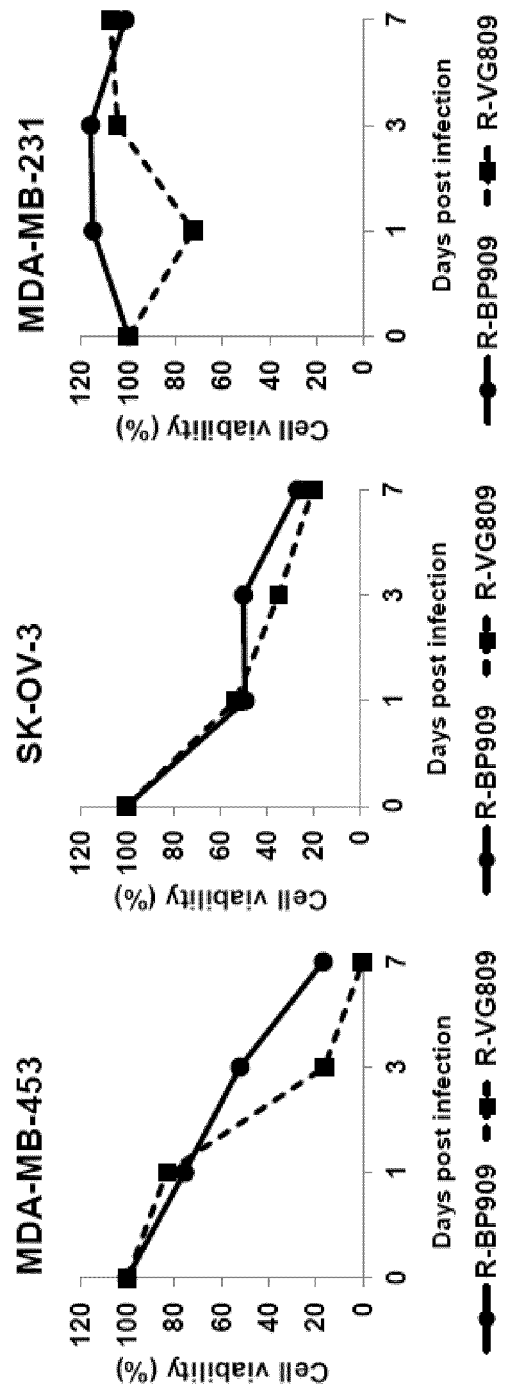

FIG. 7: Killing ability of R-BP909 and R-VG809 for SK-OV-3 and MDA-MB-453 cells infected, and lack of killing ability for HER2$^-$ cancer cells. The HER2-positive SK-OV-3 and MDA-MB-453 cells, and the HER2$^-$ MDA-MB-231 cancer cells were infected with the indicated viruses at 2 PFU/cell (0.1 PFU/cell for MDA-MD-231 cells), respectively. Viability was quantified by AlamarBlue assay. R-BP909 killed the SK-OV-3 and MDA-MB-453 cells with similar efficiency to R-VG809. Both viruses failed to kill the HER2$^-$ negative MDA-MD-231 cancer cells, consistent with their inability to infect these cells.

FIG. 8: Pattern of infection of the recombinants R-313, R-315, R-317 and R-319. wt-Vero, Vero-GCN4R, SK-OV-3, parental J and J cells that express receptors for wt-HSV J-HVEM and J-Nectin were infected with the indicated viruses and monitored for green fluorescence microscopy 24 h post infection. R-313, R-315, R-317 and R-319 infect cells that express HER2 (both human and simian) and GCN4 as receptors and fails to infect through Nectin and HVEM, as a consequence of gD deletion of AA 6-38. All the engineered viruses are retargeted to HER2 and GCN4 and detargeted from HSV-1 gD natural receptors. Inhibition of infection in HER2-positive cell lines exposed to Trastuzumab (alias Herceptin) confirms that R-313, R-315, R-317 and R-319 employ the HER2 as the portal of entry in these cells.

FIG. 9: Growth curves of R-313, R-315, R-317, R-319 and of the control recombinants R-LM113 (retargeted to HER-2 through gD) and R-LM5 (wt for HSV glycoproteins and with other genomic modifications present in R-313, R-315, R-317, R-319 and R-LM113). Vero-GCN4R and SK-OV-3 cells were infected with the indicated recombinants at an input multiplicity of infection of 0.1 PFU/cell (as titrated in the respective cell lines) and harvested at the indicated times (h) after infection. Progeny virus was titrated in SK-OV-3 cells.

FIG. 10: Plating efficiency of R-313, R-315, R-317, R-319 and of the control recombinants R-LM113 and R-LM5 in different cell lines. Replicate aliquots of the recombinant viruses were plated onto Vero-GCN4R, wt-Vero and SK-OV-3. At 3 days after infection, plaques were scored under the fluorescence microscope.

FIG. 11: Relative plaque size of R-313, R-315, R-317 and R-319 in different cell lines. A) Replicate aliquots of R-313, R-315, R-317, R-319, R-LM113 and R-LM5 were plated in Vero-GCN4R, wt-Vero and SK-OV-3. Pictures of plaques were taken at the fluorescence microscope 3 days after infection. Representative plaques are shown. B) Quantification of plaque areas is shown pxE2.

FIG. 12: Schematic drawing of the chimeric scFv to GCN4-Nectin receptor. The receptor presents N-terminal leader peptide and HA tag sequence, followed by the scFv to GCN4, placed between two short linker, GA and GSGA linker. The second part of the molecule corresponds to human Nectin-1 (PVRL1) residues Met143 to Val517 comprising the Nectin-1 extracellular domains 2 and 3, the TM segment and the intracellular cytoplasmic tail.

FIG. 13: Stability of Vero-GCN4 positive cells. The expression of the scFv GCN4-Nectin receptor was analysed by FACS by means of Mab to HA tag.

Diagrams show the percentage positive cells from Vero GCN4 clone 11.2 cells at passages 10, 15, 30, 40. Result: the expression of the artificial receptor remained stable after 40 consecutive passages.

FIG. 14: Genome arrangement of the recombinant R-321. The HSV-1 genome is represented as a line bracketed by internal repeats (IR). The Lox-P-bracketed BAC sequence and eGFP fluorescent marker are inserted in the intergenic region $U_L3$-$U_L4$. R-321, carries the deletion of AA 30 and 38 of mature gD and the insertion of scFv-HER2 after AA 37 of gD. R-321 carries the insertion of GCN4 peptide, with one upstream and one downstream Ser-Gly linker, between AA 43-44 of immature gB.

FIG. 15: Pattern of infection of the recombinant R-321. wt-Vero, Vero-GCN4R, SK-OV-3, parental J and J cells that express receptors for wt-HSV J-HVEM and J-Nectin were infected with the indicated viruses and monitored for green fluorescence microscopy 24 h post infection. R-321 infects cells that express HER2 (both human and simian) and GCN4 as receptors and fails to infect through Nectin and HVEM, as a consequence of gD deletion of AA 30 and 38. R-321 is retargeted to HER2 and GCN4 and detargeted from HSV-1 gD natural receptors. Inhibition of infection in HER2-positive cell lines exposed to Trastuzumab (alias Herceptin) confirms that R-321 employs the HER2 as the portal of entry in these cells.

FIG. 16: Growth curves of R-321 and of the control recombinants R-LM113 (retargeted to HER-2 through gD) and R-LM5 (wt for HSV glycoproteins and with other genomic modifications present in R-321). Vero-GCN4R and SK-OV-3 cells were infected with the indicated recombinants at an input multiplicity of infection of 0.1 PFU/cell (as titrated in the correspondent cell lines) and harvested at the indicated times (h) after infection. Progeny virus was titrated in SK-OV-3 cells.

SEQUENCES

SEQ ID NO: 1: amino acid sequence of HSV-1 gB wild type, precursor (Human herpesvirus 1 strain F, GenBank accession number: GU734771.1; gB encoded by positions 52996 to 55710).

SEQ ID NO: 2: amino acid sequence of the precursor of gB (SEQ ID NO: 1) having inserted the trastuzumab scFv between amino acids 43 and 44, as encoded by constructs R-BP903 and R-BP909. Linker SSGGGSGSGGSG (SEQ ID NO: 30) is introduced between the C-terminal amino acid sequence of the scFV insert and amino acid 44 of gB.

SEQ ID NO: 3: amino acid sequence of the precursor of gB (SEQ ID NO: 1) having inserted the trastuzumab scFv between amino acids 81 and 82, as encoded by construct R-BP901. Linker HSSGGGSG (SEQ ID NO: 29) is introduced between amino acid 81 of gB and the N-terminal amino acid sequence of the scFV insert. Linker SSGGGSGSGGSG (SEQ ID NO: 30) is introduced between the C-terminal amino acid sequence of the scFV insert and amino acid 82 of gB.

SEQ ID NO: 4: amino acid sequence of HSV-1 gD wild type, precursor (Human herpesvirus 1 strain F, GenBank accession ID: GU734771.1; gD encoded by positions 138281 to 139465).

SEQ ID NO: 5: amino acid sequence of HSV-1 gD wild type, precursor (SEQ ID NO: 4), with deletion of amino acids 6 to 38 of mature gD, as encoded by R-BP909.

SEQ ID NO: 6: amino acid sequence of HSV-1 deleted gD (SEQ ID NO: 5), having inserted the trastuzumab scFv between amino acids 30 and 64, as encoded by construct R-LM113. Amino acids EN were introduced to insert a restriction site for easiness of engineering and screening.

SEQ ID NO: 7: Trastuzumab scFv cassette bracketed by Ser-Gly linkers, present in plasmid named pSG-scFvHER2-SG, as in R-BP901, encoding the insert in SEQ ID NO: 3.

SEQ ID NO: 8: amino acid sequence encoded by SEQ ID NO: 7; amino acids 1 to 8 are the upstream Ser-Gly linker (SEQ ID NO: 29), amino acids 9 to 116 are the $V_L$ region, amino acids 117 to 136 is the linker that connects the $V_L$ and $V_H$ regions (SEQ ID NO: 31), amino acids 137 to 255 encode the $V_H$ region, amino acids 256 to 267 encode the downstream 12 Ser-Gly linker (SEQ ID NO: 30).

SEQ ID NO: 9: The Trastuzumab scFv cassette, present in plasmid named p-SG-scFvHER2-SG, but lacking the 8 residues long upstream Ser-Gly linker in R-BP903 and R-BP909, encoding the insert in SEQ ID NO: 2.

SEQ ID NO: 10: amino acid sequence encoded by SEQ ID NO: 9; amino acids 1 to 108 are the $V_L$ region, amino acids 109 to 128 is the linker that connects the $V_L$ and $V_H$ regions (SEQ ID NO: 31), amino acids 129 to 247 encode the $V_H$ region, amino acids 248 to 259 encode the downstream 12 Ser-Gly linker (SEQ ID NO: 30).

SEQ ID NO: 11: gB43GalKfor

SEQ ID NO: 12: gB43GalKrev

SEQ ID NO: 13: gB43_sc4D5_for

SEQ ID NO: 14: gB43_sc4D5_rev

SEQ ID NO: 15: gB81fGALK
SEQ ID NO: 16: gB81GALKrev
SEQ ID NO: 17: gB81sc4D5f
SEQ ID NO: 18: gB81SGr
SEQ ID NO: 19: scFv4D5_358_r
SEQ ID NO: 20: scFv4D5_315_f
SEQ ID NO: 21: gD5_galK_f
SEQ ID NO: 22: gD39_galK_r
SEQ ID NO: 23: gD_aa5_39_f
SEQ ID NO: 24: gD_aa5_39_r
SEQ ID NO: 25: galK_129_f
SEQ ID NO: 26: galK_417_r
SEQ ID NO: 27: gB_ext_for
SEQ ID NO: 28: gB_431_rev
SEQ ID NO: 29: 8 Ser-Gly linker
SEQ ID NO: 30: 12 Ser-Gly linker
SEQ ID NO: 31: Linker connecting $V_L$ and $V_H$ regions
SEQ ID NO: 32: Trastuzumab scFv
SEQ ID NO: 33: GCN4gB_43_44_JB
SEQ ID NO: 34: GCN4gB_43_44_rB
SEQ ID NO: 35: amino acid sequence of the precursor of gB (SEQ ID NO: 1) having inserted the GCN4 peptide between amino acids 43 and 44, as encoded by the construct R-313. The GCN4 peptide is flanked by a Ser-Gly linker.
SEQ ID NO: 36: nucleotide sequence encoding GCN4 peptide with upstream and downstream linkers for recombination into gB
SEQ ID NO: 37: GCN4 peptide
SEQ ID NO: 38: GCN4 epitope
SEQ ID NO: 39: amino acid sequence of scFv to GCN4 peptide
SEQ ID NO: 40: nucleotide sequence encoding scFv-GCN4-Nectin1 chimera
SEQ ID NO: 41: amino acid sequence encoded by SEQ ID NO: 40; amino acid sequence of the scFv capable of binding to the GCN4 peptide comprising an N-terminal leader peptide, an HA tag sequence, a short GA linker, the scFv sequence from amino acids 33 to 275, a short GSGA linker, and human Nectin-1 (PVRL1) residues Met143 to Val517
SEQ ID NO: 42: Genbank accession number AJ585687.1 (gene encoding the GCN4 yeast transcription factor
SEQ ID NO: 43: amino acid sequence of the GCN4 yeast transcription factor UniProtKB—P03069 (GCN_YEAST)
SEQ ID NO: 44: gB_76_galK_for
SEQ ID NO: 45: gB_76_galK_rev
SEQ ID NO: 46: gB_76_GCN4_for
SEQ ID NO: 47: gB_76_GCN4_rev
SEQ ID NO: 48: amino acid sequence of the precursor of gB (SEQ ID NO: 1) having inserted the GCN4 peptide between amino acids 76 and 77, as encoded by the construct R-317. The GCN4 peptide is flanked by a Ser-Gly linker.
SEQ ID NO: 49: gB_81_GCN4_for
SEQ ID NO: 50: gB_81_GCN4_rev
SEQ ID NO: 51: amino acid sequence of the precursor of gB (SEQ ID NO: 1) having inserted the GCN4 peptide between amino acids 81 and 82, as encoded by the construct R-315. The GCN4 peptide is flanked by a Ser-Gly linker.
SEQ ID NO: 52: gB_95_galK_for
SEQ ID NO: 53: gB_95_galK_rev
SEQ ID NO: 54: gB_95_GCN4_for
SEQ ID NO: 55: gB_95_GCN4_rev
SEQ ID NO: 56: amino acid sequence of the precursor of gB (SEQ ID NO: 1) having inserted the GCN4 peptide between amino acids 95 and 96, as encoded by the construct R-319. The GCN4 peptide is flanked by a Ser-Gly linker.
SEQ ID NO: 57: gD5_galK_f
SEQ ID NO: 58: scFv_galK_rev
SEQ ID NO: 59: gDdel30_38 for
SEQ ID NO: 60: gDdel30_38 rev
SEQ ID NO: 61: amino acid sequence of the precursor of gD (SEQ ID NO: 4) having deleted amino acids 30 and 38 and inserted the trastuzumab scFv after amino acid 37 with regard to mature gD, as encoded by the construct R-321.
SEQ ID NO: 62: amino acid sequence of HSV-1 gD wild type, mature form (Human herpesvirus 1 strain F, GenBank accession ID: GU734771.1).

EXAMPLES

Example 1: Construction of HSV Recombinants Expressing Genetically Modified gBs Carrying a Single Chain Antibody (scFv) Directed to HER2 (scFv-HER2) (R-BP901, R-BP903, R-BP909), without or with Deletion in the gD HSV Gene, and Encoding eGFP as Reporter Gene, or Carrying the GCN4 Peptide (R-313)

A) R-BP903: insertion of scFv-HER2 between AA (amino acid) 43 and 44 of HSV gB.

The inventors engineered R-BP903—this clone has also the name R-903—(FIG. 1A) by insertion of the sequence encoding the trastuzumab scFv between AA 43 and 44 of immature gB, corresponding to AA 13 and 14 of mature gB, after cleavage of the signal sequence, which encompasses AA 1-30. The starting genome was the BAC LM55, which carries LOX-P-bracketed pBeloBAC11 and eGFP sequences inserted between UL3 and UL4 of HSV-1 genome (Menotti et al., 2008). The engineering was performed by means of galK recombineering. Briefly, the galK cassette with homology arms to gB was amplified by means of primers gB43GalKfor GGTGGCGTCGGCGGCTCCGAGTTCCCCCGGCACG CCTGGGGTCGCGGCCG CGCCTGTTGACAATTAATCATCGGCA (SEQ ID NO: 11) and gB43GalKrev GGCCAGGGGCGGGCGGCGCCG-GAGTGGCAGGTCCCCCGTTCGCCGCCTG GGTTCAGCACTGTCCTGCTCCTT (SEQ ID NO: 12) using pGalK as template. This cassette was electroporated in SW102 bacteria carrying LM55 BAC. The recombinant clones carrying the galK cassette were selected on plates containing M63 medium (15 mM $(NH_4)_2 50_4$, 100 mM $KH_2PO_4$, 1.8 μg $FeSO_4.H_2O$, adjusted to pH7) supplemented with 1 mg/L D-biotin, 0.2% galactose, 45 mg/L L-leucine, 1 mM $MgSO_4.7H_2O$ and 12 μg/ml chloramphenicol. In order to exclude galK false positive bacterial colonies, they were streaked also on MacConkey agar base plates supplemented with 1% galactose and 12 μg/ml chloramphenicol and checked by colony PCR with primer galK_129_f ACAATCTCTGTTTGCCAACGCATTTGG (SEQ ID NO: 25) and galK_417_r CATTGCCGCTGATCACCATGTCCACGC (SEQ ID NO: 26). Next, the trastuzumab scFv cassette with the downstream Ser-Gly linker described below (SEQ ID NO: 9; encoding SEQ ID NO: 10) and bracketed by homology arms to gB was generated through the annealing and extension of primers gB43_sc4 D5_for GGTGGCGTCGGCGGCTCCGAGTTCCCCCGGCACG CCTGGGGTCGCGGCCG CGTCCGATATCCAGATGACCCAGTCCCCG (SEQ ID NO: 13) and gB43_sc4 D5_rev GGCCAGGGGCGGGCGGCGCCG-GAGTGGCAGGTCCCCCGTTCGCCGCCTG GGTACCGGATCCACCGGAACCAGAGCC (SEQ ID NO: 14). The recombinant genome encodes for the chimeric gB, which carries the scFv to HER2 and one downstream Ser-Gly linker, with sequence SSGGGSGSGGSG (SEQ ID NO: 30), and one linker between VL and VH region with the sequence SDMPMADPNRFRGKNLVFHS (SEQ ID NO: 31). The recombinant clones carrying the excision of the galK cassette and the insertion of the sequence of choice, scFv-HER2, were selected on plates containing M63 medium (see above) supplemented with 1 mg/L D-biotin, 0.2% deoxy-2-galactose, 0.2% glycerol, 45 mg/L L-leucine, 1 mM MgSO$_4$.7H$_2$O and 12 µg/ml chloramphenicol. Bacterial colonies were also checked for the presence of sequence of choice by means of colony PCR with primers gB_ext_for GAGCGCCCCCGACGGCTGTATCG (SEQ ID NO: 27) and gB_431_rev TTGAAGACCACCGCGATGCCCT (SEQ ID NO: 28).

B) R-BP909 (FIG. 1B): deletion of AA 6-38 from mature gD of R-BP903. R-BP909—this clone has also the name R-909—is identical to R-BP903 and, in addition, it carries the deletion of the sequence corresponding to AA 6-38 in gD. The starting material was the R-BP903 BAC genome. To generate the AA 6-38 deletion in gD, galK cassette flanked by homology arms to gD was amplified with primers gD5_galK_f TTGTCGTCATAGTGGGCCTCCATGGGGTCCGCGGCAAATATGCCTTGGCGC CTGTTGACAATTAATCATCGGCA (SEQ ID NO: 21) and gD39_galK_r ATCGGGAGGCTGGGGGGCTGGAACGGGTCCGGTAGGCCCGCCTGGATGTG TCAGCACTGTCCTGCTCCTT (SEQ ID NO: 22). Next, the inventors replaced galK sequence with a synthetic double-stranded oligonucleotide made of gD_aa5_39 f TTGTCGTCATAGTGGGCCTC-CATGGGGTCCGCGGCAAATATGCCTTGGCGCA CATCCAGGCGGGCC-TACCGGACCCGTTCCAGCCCCCCAGCCTCCCGAT (SEQ ID NO: 23) and of gD_aa5_39 r ATCGG-GAGGCTGGGGGGCTG-GAACGGGTCCGGTAGGCCCGCCTGGATGTG CGC-CAAGGCATATTTGCCGCGGACCCCATGGAGGCCC ACTATGACGACAA (SEQ ID NO: 24).

C) R-BP901—this clone has also the name R-901—(FIG. 1C): insertion of scFv-HER2 between aa 81 and 82 of HSV gB.

The procedure was the same as described above to engineer the scFv-HER2 in gB of R-BP903, with the following differences. First, the galK cassette was amplified by means of primers gB81fGALK CGGGGGACACGAAACCGAAGAAGAACAAAAAA CCGAAAAACCCACCGCCGC CGCCTGTTGACAAT-TAATCATCGGCA (SEQ ID NO: 15) and gB81GALKrev CGCAGGGTGGCGTGGCCCGCGGCGACGGTCGCG TTGTCGCCGGCGGGGC GTCAGCACTGTCCTGCTCCTT (SEQ ID NO: 16). Next, the trastuzumab scFv cassette bracketed by the Ser-Gly linkers described below and by homology arms to gB was amplified as two separate fragments, named fragment #1 and fragment #2, from pSG-ScFvHER2-SG. pSG-ScFvHER2-SG carries a trastuzumab scFv cassette bracketed by Ser-Gly linkers (SEQ ID NO: 7, encoding SEQ ID NO: 8). Fragment #1 was amplified by means of primers gB81sc4D5f CGGGGGACACGAAACCGAAGAAGAACAAAAAA CCGAAAAACCCACCGCCGC CGCAT-AGTAGTGGCGGTGGCTCTGGATCCG (SEQ ID NO: 17) and scFv4D5_358_r GGAAACGGTTCGGATCAGC-CATCGG (SEQ ID NO: 19), using p-SG-ScFv-HER2-SG as template. Fragment #2 was amplified by means of primers gB81SGr CGCAGGGTGGCGTGGCCCGCGGCGACGGTCGCG TTGTCGCCGGCGGGGC GACCGGATCCACCGGAACCAGAGCC (SEQ ID NO: 18) and scFv4D5_315_f GGAGATCAAATCGGA-TATGCCGATGG (SEQ ID NO: 20) using pSG-ScFvHER2-SG as template. Fragments #1 and #2 were annealed and extended to generate the scFv-HER2 cassette, bracketed by the Ser-Gly linkers and the homology arms to gB. The recombinant genome carries the scFv to HER2 bracketed by an upstream Ser-Gly linker, with sequence HSSGGGSG (SEQ ID NO: 29), and a downstream Ser-Gly linker, with sequence SSGGGSGSGGSG (SEQ ID NO: 30). The linker between VL and VH is SDMPMADPNRFRGKNLVFHS (SEQ ID NO: 31).

D) R-313: insertion of GCN4 peptide between AA 43 and 44 of HSV gB in HSV recombinant already expressing a scFv-HER2 in the deletion of AA 6-38 in gD.

The inventors engineered R-313 (FIG. 1D) by insertion of the sequence encoding the GCN4 peptide between AA 43 and 44 of immature gB, corresponding to AA 13 and 14 of mature gB after cleavage of the signal sequence, which encompasses AA 1-30. The starting genome was the BAC LM113, which carries scFv-HER2 in place of AA 6 to 38 of gD, LOX-P-bracketed pBeloBAC11 and eGFP sequences inserted between U$_L$3 and U$_L$4 of HSV-1 genome (Menotti et al., 2008). The engineering was performed by means of galK recombineering. Briefly, in order to insert the GCN4 peptide in gB, the galK cassette with homology arms to gB was amplified by means of primers gB43GalKfor GGTGGCGTCGGCGGCTCCGAGTTCCCCCGGCACG CCTGGGGTCGCGGCCG CGCCTGTTGACAATTAAT-CATCGGCA (SEQ ID NO: 11) and gB43GalKrev GGCCAGGGGCGGGCGGCGCCG-GAGTGGCAGGTCCCCCGTTCGCCGCCTG GGTTCAGCACTGTCCTGCTCCTT (SEQ ID NO: 12) using pGalK as template. This cassette was electroporated in SW102 bacteria carrying the BAC LM 113 BG. The recombinant clones carrying the galK cassette were selected on plates containing M63 medium (15 mM (NH$_4$)$_2$SO$_4$, 100 mM KH$_2$PO$_4$, 1.8 µg FeSO$_4$.H$_2$O, adjusted to pH7) supplemented with 1 mg/L D-biotin, 0.2% galactose, 45 mg/L L-leucine, 1 mM MgSO$_4$.7H$_2$O and 12 µg/ml chloramphenicol. In order to exclude galK false positive bacterial colonies, they were streaked also on MacConkey agar base plates supplemented with 1% galactose and 12 µg/ml chloramphenicol and checked by colony PCR with primer galK_129_f ACAATCTCTGTTTGCCAACGCATTTGG (SEQ ID NO: 25) and galK_417_r CATTGCCGCTGAT-CACCATGTCCACGC (SEQ ID NO: 26). Next, the GCN4 peptide cassette (SEQ ID NO: 36, encoding SEQ ID NO: 37) with the downstream and upstream Ser-Gly linkers and bracketed by homology arms to gB was generated through the annealing and extension of primers GCN4gB_43_44 JB GGTGGCGTCGGCGGCTCCGAGTTCCCCCGGCACG CCTGGGGTCGCGGCCG CGGGATCCAAGAACTAC-CACCTGGAGAACGAGGTGGCCAGACTGAAGAAGC TGGTGGGCAGC (SEQ ID NO: 33) and GCN4gB_43_44_rB GGCCAGGGGCGGGCGGCGCCG-GAGTGGCAGGTCCCCCGTTCGCCGCCTG GGTGCTGCCCACCAGCTTCTTCAGTCTGGC-CACCTCGTTCTCCAGGTGGTAG TTCTTGGATCC (SEQ ID NO: 34) which introduce a silent restriction site for the BamHI endonuclease, useful for screening of colonies by means of restriction analysis. The recombinant genome encodes the chimeric gB (SEQ ID NO: 35), which carries the GCN4 peptide including one downstream and one upstream Ser-Gly linker with the sequence GS. The recombinant clones carrying the excision of the galK cassette and the insertion of the sequence of choice, GCN4 peptide, were selected on plates containing M63 medium (see above) supplemented with 1 mg/L D-biotin, 0.2% deoxy-2-galactose, 0.2% glycerol, 45 mg/L L-leucine, 1 mM $MgSO_4.7H_2O$ and 12 μg/ml chloramphenicol. Bacterial colonies were checked for the presence of sequence of choice by means of colony PCR with primers gB_ext_for GAGCGCCCCCGACGGCTGTATCG (SEQ ID NO: 27) and gB_431_rev TTGAAGACCACCGCGATGCCCT (SEQ ID NO: 28).

To reconstitute the recombinant virus R-BP909, 500 ng of recombinant BAC DNA was transfected into the gD-complementing cell line named R6 (rabbit skin cell line expressing wt-gD under the control of the HSV late UL26.5 promoter (Zhou et al., 2000) by means of Lipofectamine 2000 (Life Technologies), and then grown in SK-OV-3 cells. Virus growth was monitored by green fluorescence. The structure of the recombinants was verified by sequencing the entire gB and also gD and gH ORFs for R-BP909, the scFv HER2 and the insertion site in gB of R-BP903 and R-BP901. Virus stocks were generated and titrated in SK-OV-3 cells.

To reconstitute the recombinant viruses R-BP901, R-BP903, R-313, 500 ng of recombinant BAC DNA was transfected into SK-OV-3 cells by means of Lipofectamine 2000 (Life Technologies). Virus growth was monitored by green fluorescence. The R-313 virus was passaged six times in SK-OV-3, frozen/thaw to lyse the SK-OV-3 cells and subsequently growth in Vero-GCN4 cells. Virus stocks were generated in Vero-GCN4 and titrated in Vero-GCN4, wt-Vero and SK-OV-3 cells. The structure of the recombinant R-313 was verified by sequencing the GCN4 and the insertion site in gB.

Example 2: Verification of Expression of the Chimeric scFv-HER2-gB of R-BP901 and R-BP909

SK-OV-3 cells were infected at an input multiplicity of infection of 3 PFU/cell with R-BP901, R-BP909, and with R-LM5, for comparison, and harvested 72 h after infection. Cell lysates were subjected to polyacrylamide gel electrophoresis, transferred to PVDF membranes and immunoblotted with monoclonal antibody (H1817) to gB. FIG. 2 shows that the chimeric scFv-HER2-gB from R-BP901 and R-BP909 migrated with a slower electrophoretic mobility than wt-gB from R-LM5, and an apparent $M_r$ of 130 KDaltons. Arrows point to the migration position of chimeric and wt gB. figures to the left indicate the migration position of molecular weight markers, expressed in kDaltons.

Example 3: Infection of J Cells Expressing Single Receptors with Recombinants R-BP903, R-BP909 and R-BP901

It has previously been shown that the insertion of scFv-HER2 in gD confers to the recombinant virus R-LM113 the ability to enter cells through the HER2 receptor. To provide evidence that the insertion of scFV-HER2 at positions 43-44 or 81-82 of gB confers the ability to enter cells through the HER2 receptor, the inventors made use of cells that express HER2 as the sole receptor. The parental J cells express no receptor for gD, hence cannot activate gD, and are not infected by wt-HSV. J-HER2 cells transgenically express HER2 as the sole receptor. As controls, the inventors included J-Nectin and J-HVEM cells, which transgenically express Nectin-1 or HVEM as receptors and are infected by wt-HSV. The indicated cells were infected with R-BP903, R-BP909 and R-BP901 and monitored for green fluorescence microscopy 24 h post infection.

As shown in FIG. 3A, R-BP903 infected J-HER2 cells. The infection of J-Nectin, J-HVEM was not surprising, inasmuch as R-BP903 encodes a wt-gD. This virus is retargeted to HER2 and retains the natural tropism.

The inventors engineered a recombinant carrying the scFv-HER2 in position 43-44 of gB and the deletion of portions of receptors' binding sites from gD. The two major receptors of gD are Nectin-1 and HVEM. The binding site of HVEM in gD maps to AA 1-32. The binding site of Nectin-1 in mature gD is more widespread and includes the Ig-folded core and portions located between AA 35-38, 199-201, 214-217, 219-221. The inventors deleted from R-BP903 mature gD the AA 6-38 region, i.e. the same region which was previously deleted from R-LM113, a HSV retargeted to HER2 by insertion of the scFv-HER2 between AA 5 and 39 of mature gD. The deletion removes the entire HVEM binding site and some residues implicated in the interaction with Nectin-1, including portions located between AA 35-38. Even though a few AA implicated in the interaction with Nectin-1 were deleted, R-LM113 was shown to be detargeted from both Nectin-1 and HVEM. The recombinant virus named R-BP909 failed to infect not only J-HVEM cells, but also J-Nectin cells, and maintained the ability to infect efficiently J-HER2 cells (FIG. 3B). R-BP909 tropism is strikingly different from that of R-BP903 (compare FIG. 3A with FIG. 3B). The inventors conclude that R-BP909 infection via the HER2-retargeted gB does not require the binding sites for HVEM and for Nectin-1 in gD, and, consequently, the receptor-mediated gD activation. In summary, R-BP909 exhibits a fully redirected tropism, retargeted to the HER2 receptor via gB and detargeted from gD receptors.

The recombinant R-BP901 which carries the scFv HER2 between AA 81 and 82 of gB and has wt gD fails to infect J-HER2 cells; this virus is not retargeted to HER2 (FIG. 3C).

Example 4: Infection of $HER2^+$ and $HER2^-$ Cancer Cells

The SK-OV-3, BT-474, MDA-MB-453 HER2+ cancer cells, and the $HER2^-$ HeLa and MDA-MB-231 cancer cells, and the $HER2^-$ non-cancer HaCaT cells were infected at an input multiplicity of infection of 5 PFU/cell (as titrated in SK-OV-3) for 90 min at 37° C. with R-BP909 and R-BP903. Pictures were taken 24 h after infection at fluorescence microscope. R-BP909 infects the HER2-positive cancer cells and fails to infect the HER2-negative cells. R-BP903 infects cells irrespective of the expression of HER2, in agreement with the lack of detargeting (FIG. 4).

Example 5: Characterization of R-BP909 Entry Pathways in J-HER2 and SK-OV-3

To prove that entry of R-BP909 into J-HER2 cells occurs through HER2 as the cellular receptor, and to investigate the role of gD in the entry pathway of R-BP909 into SK-OV-3 cells, the inventors performed a series of blocking assays.

In addition, R-LM5, which carries a wt-gD and the other genomic modifications present in R-BP909 and R-LM113, namely the insertion of the BAC sequences and the insertion of the GFP marker, was employed as control. The inventors first confirmed that infection of R-BP909 occurs through the HER2 receptor. Replicate monolayers of J-HER2 cells, or SK-OV-3 cells in 12-well plates were preincubated with trastuzumab, the MAb to HER2 from which the scFv-HER2 was derived or with non-immune mouse IgG (28 μg/ml final concentration). After 1 h at 37° C. of pre-incubation with antibodies, the cells were infected at an input multiplicity of infection of 5 PFU/cell (as titrated in SK-OV-3) with R-BP909 and R-LM113 or R-LM5, as comparison. R-BP909 infection of both cell types was almost abolished by trastuzumab, indicating that R-BP909 uses HER2 as portal of entry, and does not make use of an off-target pathway of entry. The finding that R-BP909 can make use of HER2 as receptor provides evidence that the tropism of HSV can be modified by engineering a heterologous ligand in gB. Furthermore, the infection of the gB-retargeted HSV R-BP909 into J-HER2 cells can take place in cells which lack a gD receptor, cannot be activated by its cognate receptors and cannot transmit the activation to gB. The inventors conclude that infection of R-BP909 does not necessitate a gD with functional receptor-binding sites. This validates the conclusion that the retargeted R-BP909 uses HER2 as the portal of entry in J-HER2 cells.

To elucidate the contribution of the essential glycoproteins, gD, gH/gL and as well as the portion of gB which was not modified by genetic engineering, virions were pre-incubated with MAbs to gD HD1 (1.5 ug/ml), MAbs to gB H126 (1:2000), MAb 52S to gH (ascites fluid 1:25) for 1 h at 37° C. as indicated, and then allowed to adsorb to cells for 90 min. In the case of MAb HD1, the combination of HD1 plus trastuzumab (alia herceptin) was also tested. Viral inocula were then removed, and cells were overlaid with medium containing the indicated antibodies.

Infection was quantified by fluorescent activated cell sorter (FACS) (FIG. 5). MAb H126 to gB recognizes a linear epitope in Domain I of gB, with critical residue at $Tyr_{303}$. MAb 52S to gH recognizes a continuous epitope, independent of gL, with critical residues at $Ser_{536}$ and $Ala_{537}$. R-BP909 infection of both SK-OV-3 and J-HER2 cells was abolished by MAb H126 (1:2000) (FIGS. 5A and B), indicating that a key functional domain in wt-gB was preserved in the chimera, and a role for gH/gL. MAb HD1 failed to inhibit R-BP909 and R-LM113 infection, consistent with previous findings (Gatta et al, 2015); the results support the conclusion that R-BP909 is retargeted to HER2 by means of gB, and detargeted from Nectin1/HVEM in consequence of the AA 6-38 deletion in mature gD.

Example 6: Extent of Replication of Recombinants

The inventors compared the extent of replication of R-BP909 to that of the recombinants, R-LM113 and R-VG809 that are retargeted to HER2 through the insertion of scFv-HER2 in gD and gH, respectively. Replication was measured in SK-OV-3 cells, which express HER2 and Nectin-1/HVEM as receptors.

Cells were infected at an input multiplicity of infection of 0.1 PFU/cell for 90 min at 37° C.; unabsorbed virus was inactivated by means of an acidic wash (40 mM citric acid, 10 mM KCl, 135 mM NaCl [pH 3]). Replicate cultures were frozen at the indicated times (3, 24 and 48 h) after infection and the progeny was titrated in SK-OV-3. The results in FIG. 6 show that R-BP909 replicated to a similar extent to R-VG809, about one log less than R-LM113.

Example 7: Ability of R-BP909, and of R-VG809 for Comparison, to Kill HER2-Positive Cancer Cells, and Lack of Killing Ability for HER2⁻ Cancer Cells The HER2-positive SK-OV-3 and MDA-MB-453 and the HER2-negative MDA-MB-231 cells were seeded in 96 well plates 8×10E3 cells/well, and exposed to the recombinant R-BP909, R-VG809 for comparison or mock-infected for 90 min at 37° C. The input multiplicity of infection (as titrated in the correspondent cell line) was 2 PFU/cell for the SK-OV-3 and MDA-MB-453 and of 0.1 PFU/cells for the MDA-231 cells. Alamar-Blue (10 μl/well Life Technologies) was added to the culture media at the indicated times after virus exposure and incubated for 4 h at 37° C. Plates were read at 560 and 600 nm with GloMax Discover System (Promega). For each time point, cell viability was expressed as the percentage of AlamarBlue reduction in infected versus uninfected cells, excluding for each samples the contribution of medium alone. Cytotoxicity caused by R-BP909 and R-VG809 in HER2-positive SK-OV-3 and MDA-MB-453 ranged from 70 to 90% at 7 days after infection. Both viruses failed to kill the HER2-negative MDA-MD-231 cancer cells, consistent with their inability to infect these cells (FIG. 7).

Example 8 Ability of R-313 to Replicate in Vero-GCN4 and in the Cancer Cell Line SK-OV-3

It has previously been shown that the insertion of scFv-HER2 in place of AA 6-38 of gD confers to the recombinant virus R-LM113 the retargeting to HER2 receptor and the detargeting from both Nectin-1 and HVEM. In the present invention the inventors provide evidence that R-BP909, which carries the scFv-HER2 between AA 43-44 of gB, exhibits a fully redirected tropism, retargeted to the HER2 receptor via gB.

The inventors further investigated whether gB is a suitable glycoprotein in order to retarget HSV by means of a short peptide, exemplified here by the epitope YHLENE-VARLKK (SEQ ID NO: 38) of GCN4 yeast transcription factor with two flanking wt GCN4 residues and two GS linkers, herein named GCN4 peptide. The 20 amino acid peptide should confer to R-313 the ability to infect and replicate in the Vero-GCN4 cell line, expressing the artificial receptor made of the scFv to GCN4 (Zahnd et al., 2004) fused to extracellular domains 2, 3, TM and C-tail of Nectin-1.

To test the tropism of the R-313 the inventors made use of simian wt-Vero, Vero-GCN4, SK-OV-3 and of the previously described J cells expressing or not receptors for gD. The indicated cells were infected with R-313 and, where indicated, the cells were pretreated with Trastuzumab (alias Herceptin) (28 μg/ml final concentration). The infection was monitored by green fluorescence microscopy 24 h after infection.

As shown in FIG. 8, R-313 infected both untreated Vero-GCN4 and Vero-wt, but in the presence of Trastuzumab, only the infection in Vero-GCN4 was observed. This result indicates that R-313 was able to infect Vero-GCN4. In contrast to the infection with R-313 of wt-Vero cells, this infection was not inhibited by herceptin, indicating that it was indeed mediated by the GCN4 peptide inserted in gB. The infection with R-313 of wt-Vero cells occurs through the simian ortholog of HER2 present in Vero cells, as it is indeed inhibited by exposure of cells to herceptin.

The scFv-HER2 fused to gD still enabled infection of SK-OV-3 cells through HER2, as documented by inhibition by herceptin. The lack of infection of J, J-Nectin and J-HVEM confirmed the deretargeting profile already exhibited by R-LM113, due to the deletion of AA 6-38 of gD. Cumulatively this series of results indicates that R-313 has the ability to infect Vero-GCN4 cells through the GCN4 peptide fused in gB, and the SK-OV-3 cells through HER2 in gD.

Example 9: Extent of Replication of R-313 in Vero-GCN4 and in SK-OV-3 Cells

Figure 9:
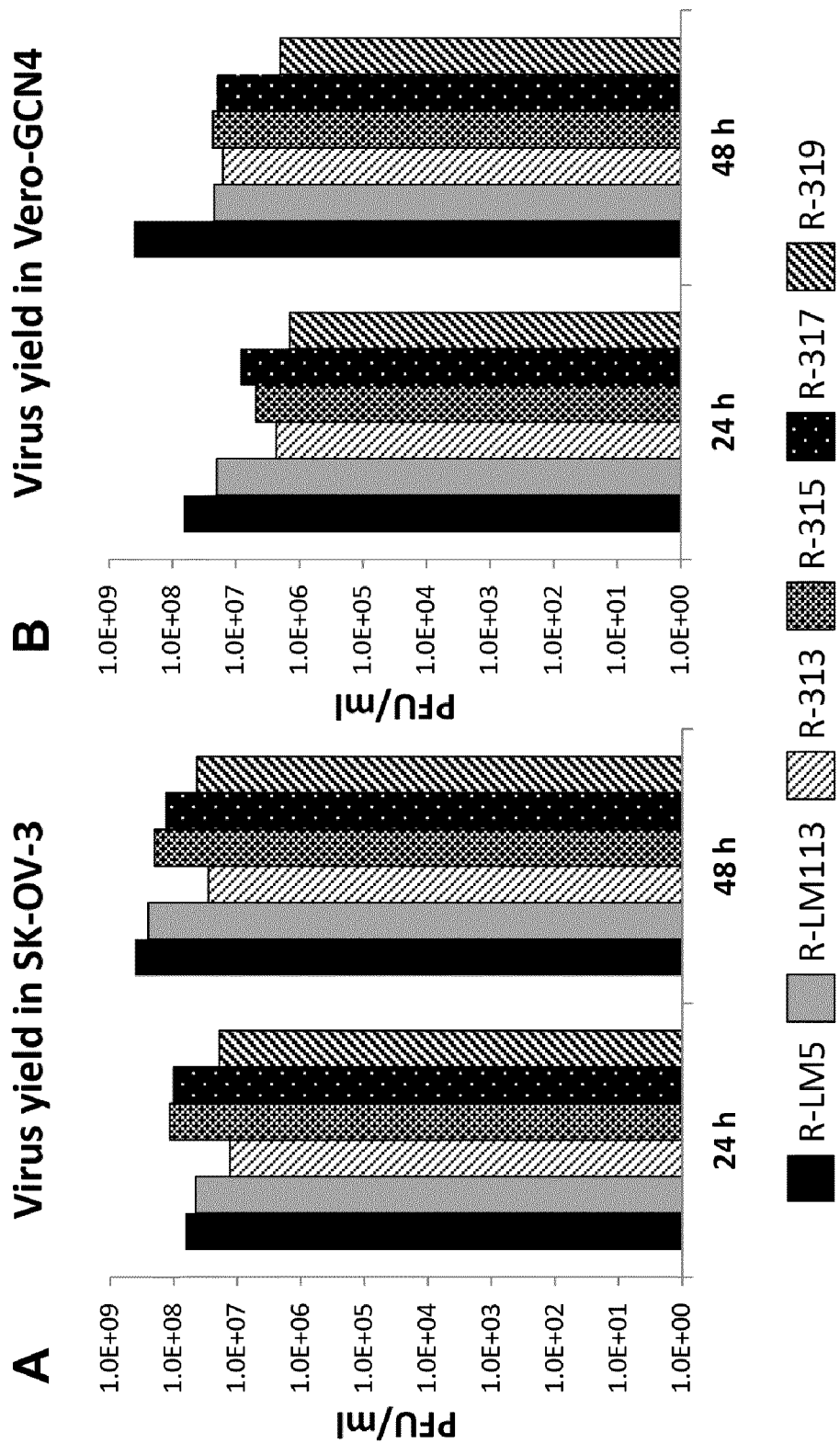

The inventors compared the extent of replication of R-313 to that of the recombinants R-LM113 and R-LM5 in Vero-GCN4 and in SK-OV-3 cells. Cells were infected at an input multiplicity of infection of 0.1 PFU/cell (as titrated in the correspondent cell line) for 90 min at 37° C.; unabsorbed virus was inactivated by means of an acidic wash (40 mM citric acid, 10 mM KCl, 135 mM NaCl [pH 3]). Replicate cultures were frozen at the indicated times (3, 24 and 48 h) after infection and the progeny was titrated in SK-OV-3. The results in FIG. 9 show that R-313 replicated in Vero-GCN4 to a higher extent than R-LM113, and to similar extent as R-LM5. R-313 can replicate in SK-OV-3 to a similar extent as R-LM113, and almost one log lower than R-LM5.

Cumulatively, the results show that R-313 is simultaneously retargeted through GCN4 and through HER2.

Example 10: Plating Efficiency of R-313 in Different Cell Lines

Figure 10:
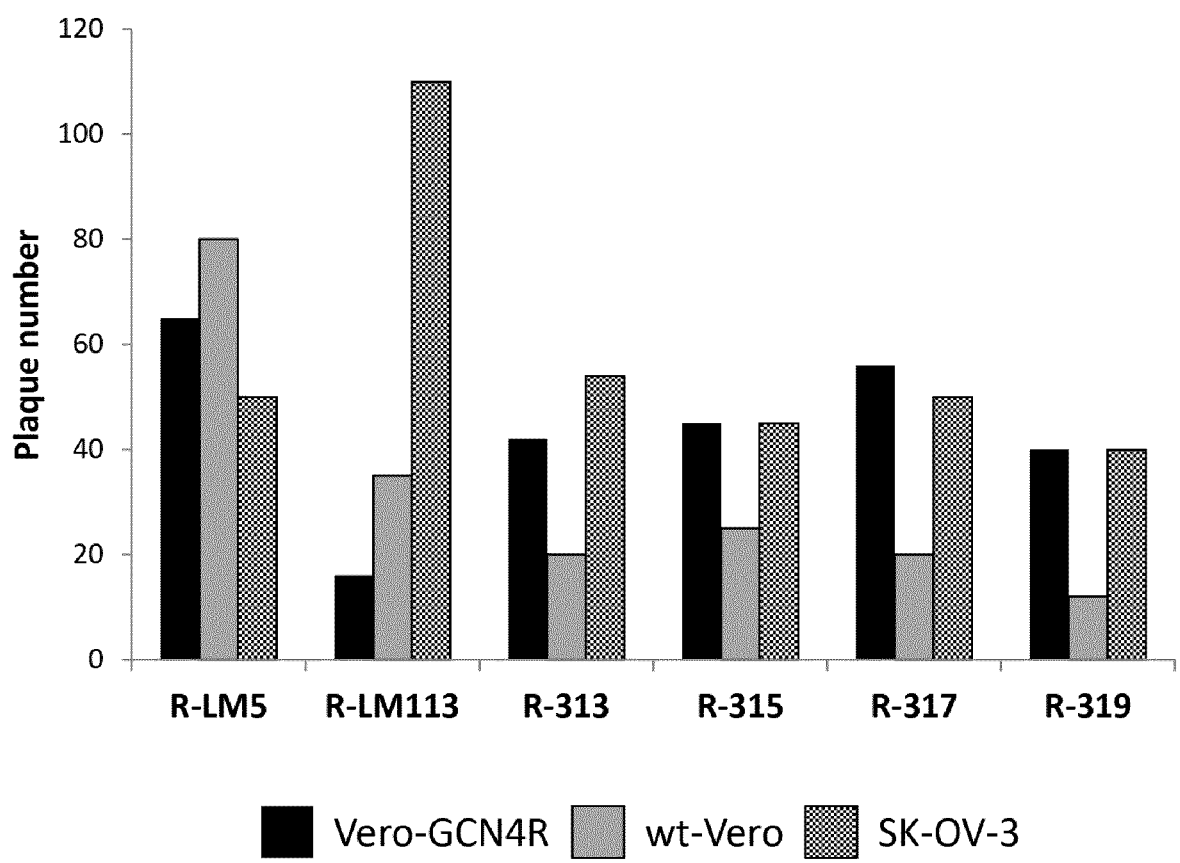

For plating efficiency experiments, the indicated cell monolayers were infected with replicate aliquots of serial dilutions (from $10^{-5}$ to $10^{-10}$) of R-313. After infection and removal of inoculum, medium containing agar was added to the plates and monolayers were incubated for 3 days at 37° C. to allow plaque formation. At $3^{rd}$ day plaques were scored under the fluorescence microscope. Figures indicate that the R-313 plating efficiency in SK-OV-3 is very similar to that in Vero-GCN4; both are slightly higher than that observed in wt-Vero cells, confirming that R-313 can make use alternatively of the GCN4 peptide engineered in gB and of the scFv-HER2 inserted in gD to enter Vero-GCN4 and SK-OV-3 cells, respectively. The plating efficiency of R-313 in J-HER2 cells could not be differentiated from that R-LM113 in the same cells, indicating that the insertion of the GCN4 peptide is not detrimental (FIG. 10).

Example 11: Relative Plaque Size of R-313 in Different Cell Lines

To perform a plaque size assay, 10-fold dilutions of R-313, R-LM113 and R-LM5 were plated onto Vero-GCN4, wt-Vero and SK-OV-3 monolayers. The infected monolayers were overlaid with medium containing agar. Three days later pictures were taken at the fluorescence microscope. Representative pictures show that in any cell line tested R-313 forms larger plaques than R-LM113. In turn, plaques formed by R-LM5 were even larger that those formed by R-313 (FIG. 11).

Example 12

A) R-315: insertion of GCN4 peptide between AA 81 and 82 of HSV gB in HSV recombinant already expressing a scFv-HER2 in the deletion of AA 6-38 in gD.

The procedure was the same as described above to engineer the GCN4 peptide in gB of R-313, with the following differences. First, the galK cassette was amplified by means of primers gB81fGALK CGGGGGACACGAAACCGAAGAAGAACAAAAA ACCGAAAAACCCACCGCCGC CGCCTGTTGACAAT-TAATCATCGGCA (SEQ ID NO: 15) and gB81GALKrev CGCAGGGTGGCGTGGCCCGCGGCGACGGTCGCG TTGTCGCCGGCGGGGC GTCAGCACTGTCCTGCTCCTT (SEQ ID NO: 16) using pGalK as template. Next, the GCN4 peptide cassette (SEQ ID NO: 36, encoding SEQ ID NO: 37) with the downstream and upstream Ser-Gly linkers and bracketed by homology arms to gB was generated through the annealing and extension of primers gB_81_GCN4_for CGGGGGACACGAAACCGAAGAAGAACAAAAA CCGAAAAACCCACCGCCGC CGGGATCCAAGAAC-TACCACCTGGAGAACGAGGTGGCCAGACT-GAAGAAGC TGGTGGGCAGC (SEQ ID NO: 49) and gB_81_GCN4_rev CGCAGGGTGGCGTGGCCCGCGGCGACGGTCGCG TTGTCGCCGGCGGGGC GGCTGCC-CACCAGCTTCTTCAGTCTGGC-CACCTCGTTCTCCAGGTGGTAGTT CTTGGATCC (SEQ ID NO: 50) which introduce a silent restriction site for the BamHI endonuclease, useful for screening of colonies by means of restriction analysis. The recombinant genome encodes the chimeric gB (SEQ ID NO: 51), which carries the GCN4 peptide including one downstream and one upstream Ser-Gly linker with the sequence GS.

B) R-317: insertion of GCN4 peptide between AA 76 and 77 of HSV gB in HSV recombinant already expressing a scFv-HER2 in the deletion of AA 6-38 in gD.

The procedure was the same as described above to engineer the GCN4 peptide in gB of R-315, with the following differences. First, the galK cassette was amplified by means of primers gB_76_galK_for GGCCCCGCCC-CAACGGGGGACACGAAACCGAAGAAGAACAAA AAACCGAAA CCTGTTGACAATTAATCATCGGCA (SEQ ID NO: 44) and gB_76_galK_rev CCCGCGGCGACGGTCGCGTTGTCGCCGGCGGGGC GCGGCGGCGGTGGGT TTCAGCACTGTCCTGCTCCTT (SEQ ID NO: 45) using pGalK as template. Next, the GCN4 peptide cassette (SEQ ID NO: 36, encoding SEQ ID NO: 37) with the downstream and upstream Ser-Gly linkers and bracketed by homology arms to gB was generated through the annealing and extension of primers gB_76_GCN4_for GGCCCCGCCC-CAACGGGGGACACGAAACCGAAGAAGAACAAA AAACCGAAA GGATCCAAGAACTACCACCTG-GAGAACGAGGTGGCCAGACTGAAGAAGCTG GTGGGCAGC (SEQ ID NO: 46) and gB_76_GCN4_rev CCCGCGGCGACGGTCGCGTTGTCGCCGGCGGGG CGCGGCGGCGGTGGGT TGCTGCC-CACCAGCTTCTTCAGTCTGGC-CACCTCGTTCTCCAGGTGGTAGTT CTTGGATCC (SEQ ID NO: 47) which introduce a silent restriction site for the BamHI endonuclease, useful for screening of colonies by means of restriction analysis. The recombinant genome encodes the chimeric gB (SEQ ID NO: 48), which carries the GCN4 peptide including one downstream and one upstream Ser-Gly linker with the sequence GS.

C) R-319: insertion of GCN4 peptide between AA 95 and 96 of HSV gB in HSV recombinant already expressing a scFv-HER2 in the deletion of AA 6-38 in gD. The procedure was the same as described above to engineer the GCN4 peptide in gB of R-317, with the following differences. First, the galK cassette was amplified by means of primers gB_95_galK_for CGCCGCCGCCCCGCCGGCGACAACGCG ACCGTCGCCGCGGGCCACGC CCCTGTTGACAAT-TAATCATCGGCA (SEQ ID NO: 52) and gB_95_galK_rev GTTTGCATCGGTGTTCTCCGCCTT- GATGTCCCGCAGGTGCTCGCGCAGGGTT CAGCACTGTCCTGCTCCTT (SEQ ID NO: 53) using pGalK as template. Next, the GCN4 peptide cassette (SEQ ID NO: 36, encoding SEQ ID NO: 37) with the downstream and upstream Ser-Gly linkers and bracketed by homology arms to gB was generated through the annealing and extension of primers gB_95_GCN4_for CGCCGCCGCGCCCCGCCGGCGACAACGCGACCG TCGCCGCGGGCCACGC CGGATCCAAGAACTAC-CACCTGGAGAACGAGGTGGCCAGACT-GAAGAAGCT GGTGGGCAGC (SEQ ID NO: 54) and gB_95_GCN4_rev GTTTGCATCGGTGTTCTCCGCCTT-GATGTCCCGCAGGTGCTCGCGCAGGGT GCTGCC-CACCAGCTTCTTCAGTCTGGC-CACCTCGTTCTCCAGGTGGTAGTTC TTGGATCC (SEQ ID NO: 55) which introduce a silent restriction site for the BamHI endonuclease, useful for screening of colonies by means of restriction analysis. The recombinant genome encodes the chimeric gB (SEQ ID NO: 56), which carries the GCN4 peptide including one downstream and one upstream Ser-Gly linker with the sequence GS.

To reconstitute the recombinant virus R-BP909, 500 ng of recombinant BAC DNA was transfected into the gD-complementing cell line named R6 (rabbit skin cell line expressing wt-gD under the control of the HSV late UL26.5 promoter (Zhou et al., 2000) by means of Lipofectamine 2000 (Life Technologies), and then grown in SK-OV-3 cells. Virus growth was monitored by green fluorescence. The structure of the recombinants was verified by sequencing the entire gB and also gD and gH ORFs for R-BP909, the scFv HER2 and the insertion site in gB of R-BP903 and R-BP901. We identified for gB of the recombinant virus R-909 one mutation (Y276S), not present in the engineered BAC-DNA. Virus stocks were generated and titrated in SK-OV-3 cells.

To reconstitute the recombinant viruses R-BP901, R-BP903, R-313, R-315, R-317 and R-319 500 ng of recombinant BAC DNA was transfected into SK-OV-3 cells by means of Lipofectamine 2000 (Life Technologies). Virus growth was monitored by green fluorescence. The R-313 virus was passaged six times in SK-OV-3, frozen/thawed to lyse the SK-OV-3 cells and subsequently growth in Vero-GCN4R cells. Virus stocks were generated in Vero-GCN4R and titrated in Vero-GCN4R, wt-Vero and SK-OV-3 cells. The genome of the recombinant R-313, R-315, R-317 and R-319 was partially verified by sequencing the entire gB.

Example 13: Ability of R-313, R-315, R-317 and R-319 to Replicate in Vero-GCN4R and in the Cancer Cell Line SK-OV-3

It has previously been shown that the insertion of scFv-HER2 in place of AA 6-38 of gD confers to the recombinant virus R-LM113 the retargeting to HER2 receptor and the detargeting from both Nectin-1 and HVEM. In the present invention the inventors provide evidence that R-BP909, which carries the scFv-HER2 between AA 43-44 of gB, exhibits a fully redirected tropism, retargeted to the HER2 receptor via gB.

The inventors further investigated whether gB is a suitable glycoprotein in order to retarget HSV by means of a short peptide, exemplified here by the epitope YHLENE-VARLKK (SEQ ID NO: 38) of GCN4 yeast transcription factor with two flanking wt GCN4 residues and two GS linkers, herein named GCN4 peptide. The 20 amino acid peptide should confer to R-313, R-315, R-317 and R-319 the ability to infect and replicate in the Vero-GCN4R cell line, expressing the artificial receptor made of the scFv to GCN4 (Zahnd et al., 2004) fused to extracellualr domains 2, 3, TM and C-tail of Nectin-1.

To test the tropism of the R-313, R-315, R-317 and R-319, the inventors made use of simian wt-Vero, Vero-GCN4R, SK-OV-3 and of the previously described J cells expressing or not receptors for gD. The indicated cells were infected with the indicated recombinant and, where indicated, the cells were pretreated with Trastuzumab (alias Herceptin) (28 µg/ml final concentration). The infection was monitored by green fluorescence microscopy 24 h after infection.

As shown in FIG. 8, R-313 (panel A), R-315 (panel B), R-317 (panel C) and R-319 (panel D) infected both untreated Vero-GCN4R and Vero-wt, but in the presence of Trastuzumab (alias Herceptin), only the infection in Vero-GCN4R was observed. This result indicates that all the recombinant viruses that carry the insertion of GCN4 peptide in different position of gB were able to infect Vero-GCN4R. In contrast to the infection of wt-Vero cells, the infection of Vero-GCN4R, was not inhibited by Herceptin, indicating that it was indeed mediated by the GCN4 peptide inserted in gB. The infection with R-313,R-315, R-317 and R-319 of wt-Vero cells occurs through the simian ortholog of HER2 present in Vero cells, as it is indeed inhibited by exposure of cells to Herceptin.

The scFv-HER2 inserted in gD still enabled infection of SK-OV-3 cells through HER2, as documented by inhibition by Herceptin. The lack of infection of J, J-Nectin and J-HVEM confirmed the deretargeting profile already exhibited by R-LM113, due to the deletion of AA 6-38 of gD. Cumulatively this series of results indicates that R-313, R-315, R-317 and R-319 have the ability to infect Vero-GCN4R cells through the GCN4 peptide inserted in gB, and the SK-OV-3 cells through HER2 in gD.

Example 14: Extent of Replication of R-313, R-315, R-317 and R-319 in Vero-GCN4R and in SK-OV-3 Cells The inventors compared the extent of replication of R-313, R-315, R-317, R-319 to that of the recombinants R-LM113 and R-LM5 in SK-OV-3 cells (FIG. 9 A) and in Vero-GCN4R (FIG. 9 B). Cells were infected at an input multiplicity of infection of 0.1 PFU/cell (as titrated in the correspondent cell line) for 90 min at 37° C.; unabsorbed virus was inactivated by means of an acidic wash (40 mM citric acid, 10 mM KCl, 135 mM NaCl [pH 3]). Replicate cultures were frozen at the indicated times (24 and 48 h) after infection and the progeny was titrated in SK-OV-3. It can be seen from FIG. 9 A that R-315 and R-317 grew to similar titers as R-LM5 and R-LM113 in SK-OV-3 cells. In contrast, R-313 and R-319 grew about one-two log less than R-315 and R-317. The results in FIG. 9 B show that R-313, R-315 and R-317 replicated in Vero-GCN4R to a similar extent as R-LM113, and one log lower than R-LM5. In turn, R-319 grew about one-two log less than R-315, R-317 and R-319.

Cumulatively, the results show that R-313, R-315, R-317 and R-319 are simultaneously retargeted through GCN4 and through HER2.

Example 15: Plating Efficiency of R-313, R-315, R-317 and R-319 in Different Cell Lines The inventors compared the ability of R-313, R-315, R-317 and R-319 to form plaques in different cell lines, with respect to the number (FIG. 10). Replicate aliquots of R-LM5, R-LM113, R-313, R-315, R-317 and R-319, containing a same amount of virus (50 PFU), as titrated in SK-OV-3 cells, were plated on wt-Vero, Vero-GCN4R and SK-OV-3. The infected monolayers were overlaid with medium containing agar and the number of plaques was scored 3 days later.

The results of the experiment indicate that the plating efficiency of all recombinant virus carrying the GCN4 peptide insertion in gB (R-313, R-315, R-317 and R-319), but not of the control viruses, was higher on Vero-GCN4R cells in comparison to wt-Vero. All the gB-recombinants exhibited similar plating efficiency in Vero-GCN4R and in SK-OV-3 cells.

Example 16: Relative Plaque Size of R-313, R-315, R-317 and R-319 in Different Cell Lines To perform a plaque size assay, 10-fold dilutions of R-313, R-315, R-317 and R-319 were plated onto Vero-GCN4R, wt-Vero and SK-OV-3 monolayers. The infected monolayers were overlaid with medium containing agar. Three days later pictures were taken at the fluorescence microscope. Representative pictures show that in any cell line tested R-313, R-315, R-317 and R-319 form larger plaques than R-LM113. Plaques formed by R-LM5 were even larger (FIG. 11). For plaque size determinations (FIG. 11B), pictures of 5 plaques were taken for each virus. Plaque areas (pxE2) were measured with Nis Elements-Imaging Software (Nikon). Each result represents average areas±SD.

Example 17: R-321: Reintroduction of AA 6-29 and 31-37 of gD in HSV Recombinant Already Expressing a scFv-HER2 in the Deletion of AA 6-38 in gD and GCN4 Peptide Between AA 43 and 44 of gB First, the galK cassette was amplified by means of primers gD5_galK_f
TTGTCGTCATAGTGGGCCTC-CATGGGGTCCGCGGCAAATATGCCTTGGCGC CTGTTGACAATTAATCATCGGCA (SEQ ID NO: 57) and scFv_galK_rev GAGGCGGACAGG-GAGCTCGGGGACTGGGTCATCTGGATATCGGAAT-TCTCT CAGCACTGTCCTGCTCCTT (SEQ ID NO: 58) using pGalK as template. The galK cassette was inserted in R-313 backbone by means of galK recombineering. Next, the oligo that comprises AA 6-29 and 31-37 of gD was generated through the annealing and extension of primers gDdel30_38 for TTGTCGTCATAGTGGGCCTC-CATGGGGTCCGCGGCAAATATGCCTTGGCGG ATGCCTCTCTCAAGATGGCCGACCC-CAATCGCTTTCGCGGCAAAGACCTTCC GGTCC (SEQ ID NO: 59) and gDde130_38 rev GAGGCGGACAGGGAGCTCGGGGACTGGGT-CATCTGGATATCGGAATTCTCC ACGCGCCGGACCCCCG-GAGGGGTCAGCTGGTCCAGGACCGGAAGGTCTTT GCCGCGA (SEQ ID NO: 60). The recombinant genome encodes the chimeric gD (SEQ ID NO: 61), which carries the deletion of AA 30 and 38 of gD and the insertion of scFv-HER2 after AA 37 of gD. SEQ ID NO: 35 shows the chimeric gB having inserted the GCN4 peptide between amino acids 43 and 44. The structure of the recombinant BAC was verified by sequencing the upstream and downstream the region 6-37 of gD.

To reconstitute the recombinant virus R-321, 500 ng of recombinant BAC DNA was transfected into SK-OV-3 cells by means of Lipofectamine 2000 (Life Technologies). Virus growth was monitored by green fluorescence. The R-321 virus was passaged six times in SK-OV-3, frozen/thaw to lyse the SK-OV-3 cells and subsequently growth in Vero-GCN4R cells.

Example 18: R-321 is Retargeted from HSV-1 Natural Receptors

It has previously been shown that the insertion of scFv-HER2 in place of AA 6-38 of gD confers to the recombinant virus R-LM113 the retargeting to HER2 receptor and the detargeting from both Nectin-1 and HVEM. In the present invention the inventors provide evidence that R-321, which carries the deletion of only AA 30 and 38 of gD and the insertion of scFv-HER2 after AA 37 of gD, exhibits a fully de-targeted profile, since it loss the ability to infect trough HSV-1 natural receptors. Moreover, R-321 carries the GCN4 peptide between AA 43 and 44 of gB, like R-313.

To test the tropism of the R-321, inventors made use of simian wt-Vero, Vero-GCN4R, SK-OV-3 and of the previously described J cells expressing or not receptors for gD. The indicated cells were infected with R-321 and, where indicated, the cells were pretreated with Trastuzumab (alias Herceptin) (28 µg/ml final concentration). The infection was monitored by green fluorescence microscopy 24 h after infection.

Figure 15:
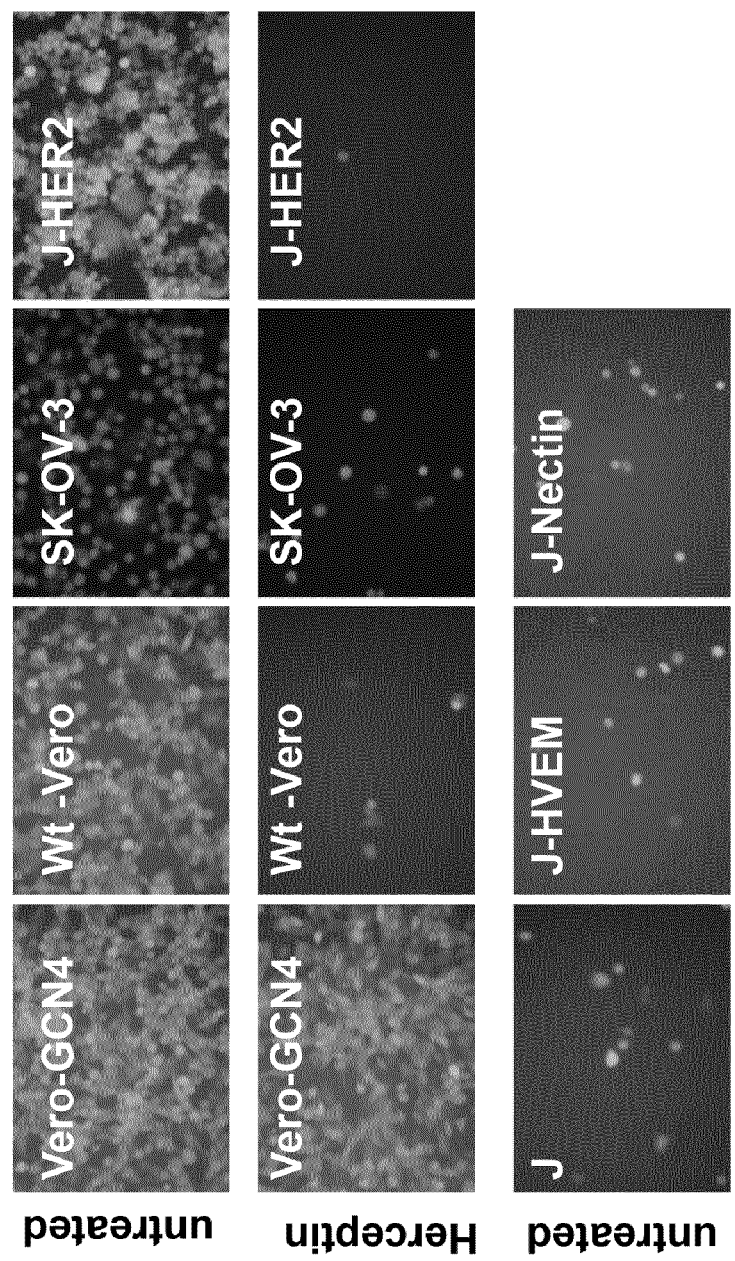

The lack of infection of J, J-Nectin and J-HVEM (FIG. 15) indicates that R-321 is de-targeted from HSV-1 natural receptors, due to the deletion of AA 30 and 38 of gD. The scFv-HER2 fused to gD enabled infection of SK-OV-3 cells through HER2, as documented by inhibition by Herceptin. As shown in FIG. 15, R-321 infected both untreated Vero-GCN4R and Vero-wt, but in the presence of Trastuzumab (alias Herceptin), only the infection in Vero-GCN4R was observed. This result indicates that R-321 is able to infect Vero-GCN4R, as R-313. In contrast to the infection of wt-Vero cells, the infection of Vero-GCN4R, was not inhibited by Herceptin, indicating that it was indeed mediated by the GCN4 peptide inserted in gB. The infection with R-321 occurs through the simian ortholog of HER2 present in Vero cells, as it is indeed inhibited by exposure of cells to Herceptin.

Cumulatively, the results show that R-321 is simultaneously retargeted through GCN4 and through HER2 and de-targeted from HSV natural receptor as a consequence of deletion of aa 30 and 38 in gD.

Example 19: Extent of Replication of R-321 in Vero-GCN4R and in SK-OV-3 Cells

Figure 16:
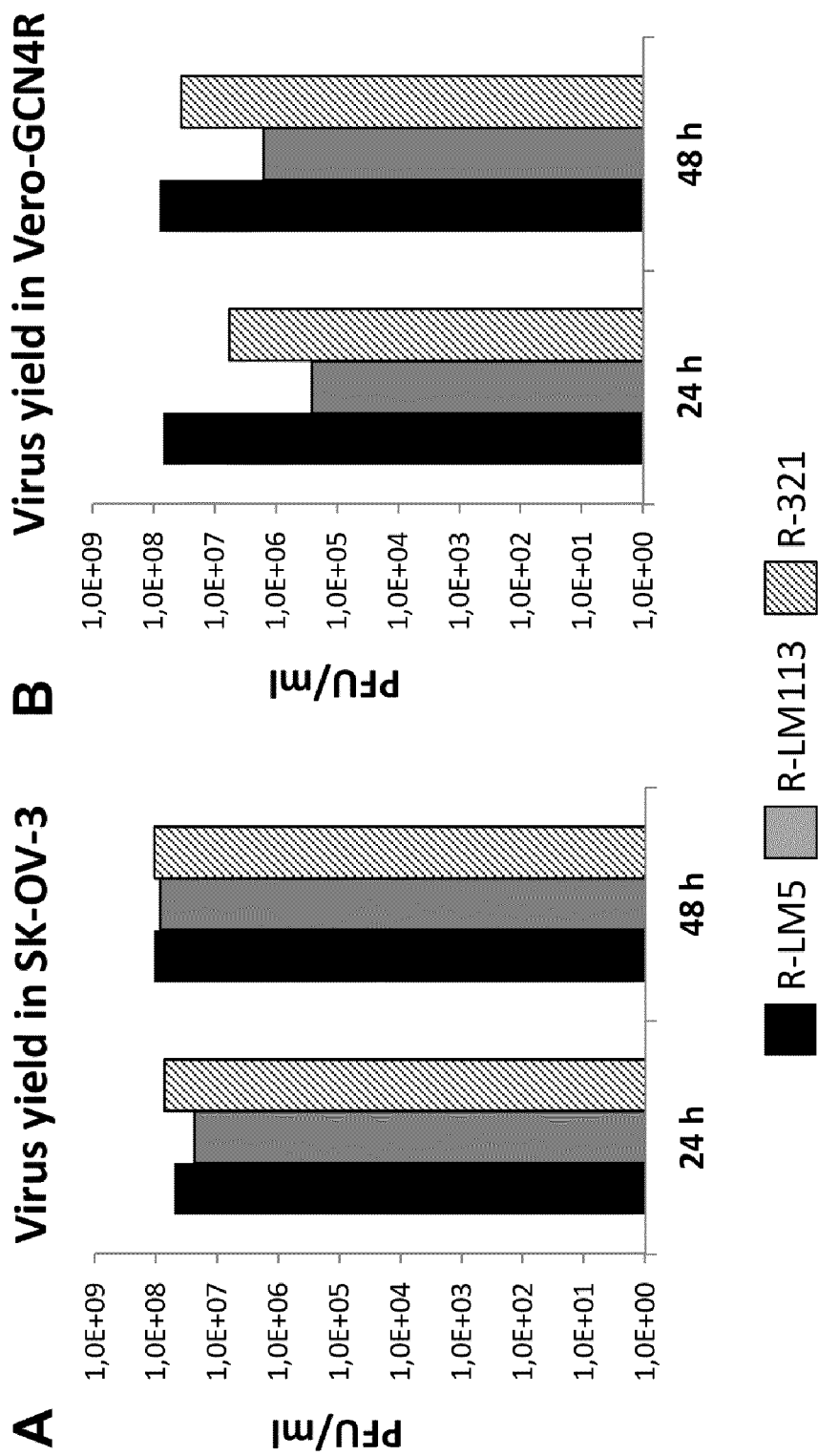

The inventors compared the extent of replication of R-321 to that of the recombinants R-LM113 and R-LM5 in SK-OV-3 cells (FIG. 16 A) and in Vero-GCN4R (FIG. 16 B). Cells were infected at an input multiplicity of infection of 0.1 PFU/cell (as titrated in the correspondent cell line) for 90 min at 37° C.; unabsorbed virus was inactivated by means of an acidic wash (40 mM citric acid, 10 mM KCl, 135 mM NaCl [pH 3]). Replicate cultures were frozen at the indicated times (24 and 48 h) after infection and the progeny was titrated in SK-OV-3. It can be seen from FIG. 16 A that R-321 grew to similar titers as R-LM5 and R-LM113 in SK-OV-3 cells. The results in FIG. 16 B show that R-321 replicated in Vero-GCN4R one log higher than R-LM113, and to similar extent than R-LM5.

Example 20: Vero-GCN4 Cell Line

Figure 12:
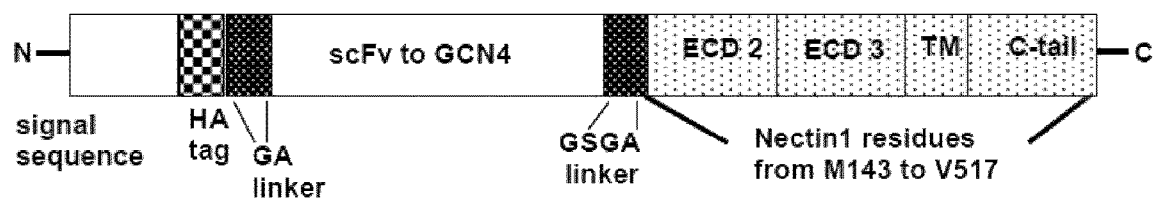

The Vero GCN4 cell line expresses an artificial chimeric receptor, made of an scFv to the GCN4 peptide (Zahnd et al., 2004), with the sequence optimized for human codon usage as reported in SEQ ID NO: 39, fused to Nectin-1. The GCN4 peptide is part of the *Saccharomyces cerevisiae* transcription factor GCN4, whose partial mRNA sequence is reported in SEQ ID NO 42. More in detail, an N-terminal leader peptide and HA tag sequence is present like in the pDISPLAY (Invitrogen) vector. This should ensure efficient and proper processing of the leader peptide. After the HA tag, a short GA linker is present upstream of the scFv. The amino acid sequence of the scFv to GCN4 is reported in SEQ ID NO: 39. C-terminal to the scFv a short GSGA linker is present. The rest of the molecule corresponds to human Nectin-1 (PVRL1) residues Met143 to Val517 comprising the Nectin-1 extracellular domains 2 and 3, the TM segment and the intracellular cytoplasmic tail (FIG. 12). The chimera was synthesized in vitro by Gene Art, and cloned into pcDNA3.1—Hygro_(+), resulting in plasmid scFv_GCN4_Nectin1 chimera, whose insert has the nucleotide sequence identified by SEQ ID NO: 40, encoding the amino acid sequence of the scFv-GCN4 nectin1 chimera SEQ ID NO: 41.

The DNA from plasmid scFv_GCN4_Nectin1 chimera was transfected into Vero cells (ATCC CCL-81™) by means of Lipofectamine 2000. Vero cells expressing the artificial receptor to the GCN4 peptide were selected by means of Hygromycin (200 µg/ml), and subsequently sorted by means of magnetic beads (Miltenyi), in combination with MAb to HA tag. The sorted cells were subjected to single cell cloning in 96 well (0.5 cell/well).

Figure 13:
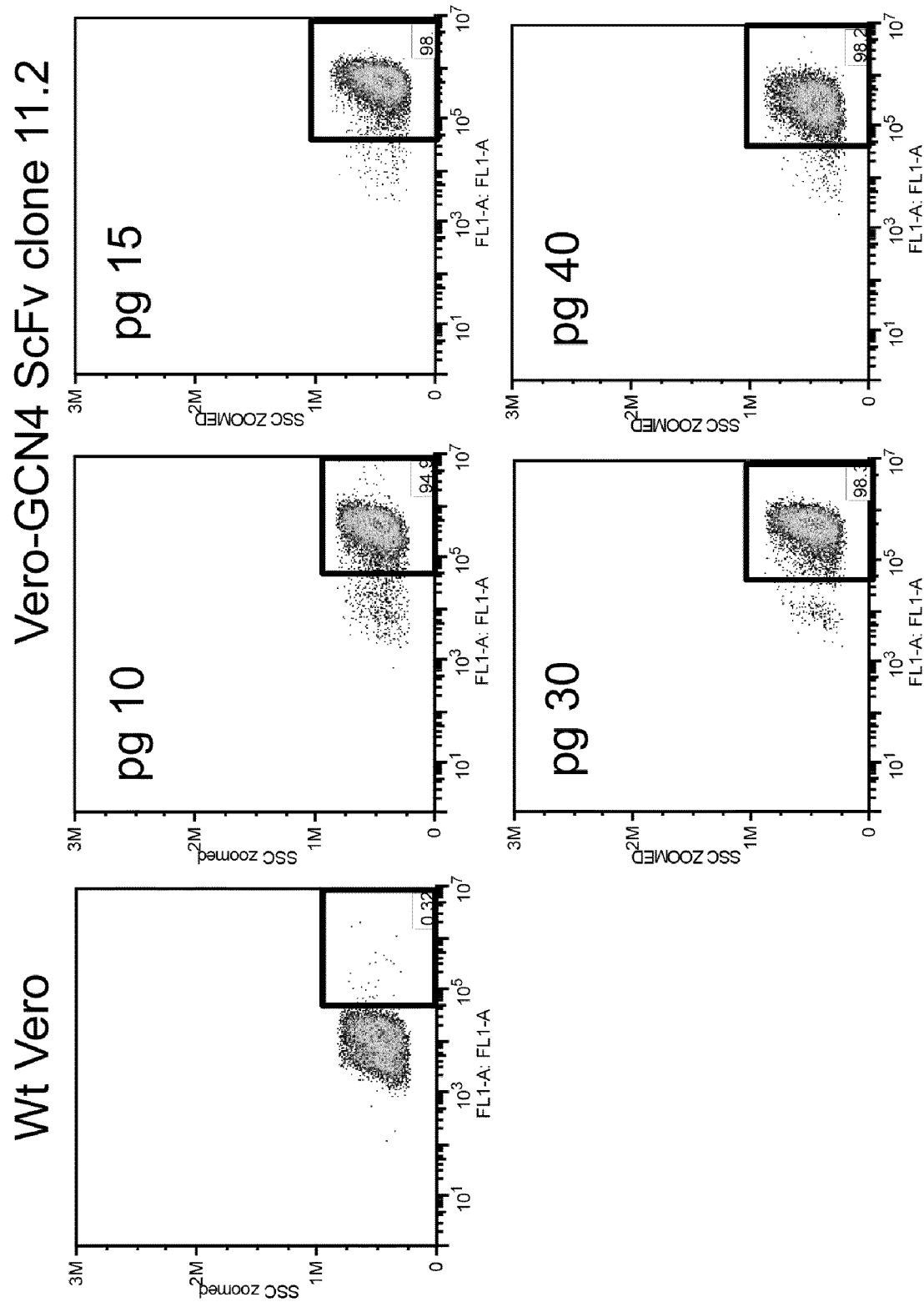
Figure 14:
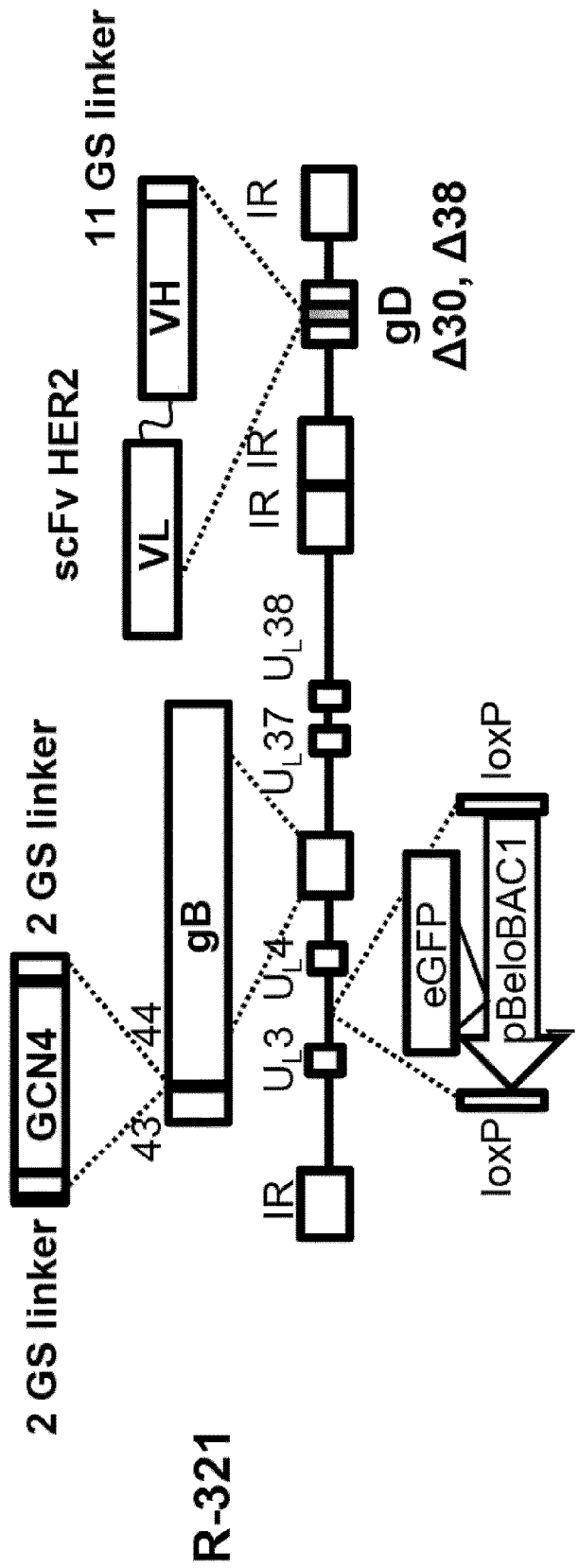

Single clones were analysed by FACS for detection of expression of the scFv to the GCN4 peptide by means of MAb to HA tag. The selected clone was 11.2. We ascertained that during serial passages of the Vero-GCN4 cell line, the expression of the artificial receptor remained stable after 40 consecutive passages (FIG. 13).

```
                    85                  90                  95
Leu Arg Glu His Leu Arg Asp Ile Lys Ala Glu Asn Thr Asp Ala Asn
            100                 105                 110
Phe Tyr Val Cys Pro Pro Thr Gly Ala Thr Val Gln Phe Glu
            115                 120                 125
Gln Pro Arg Arg Cys Pro Thr Arg Pro Glu Gly Gln Asn Tyr Thr Glu
130                 135                 140
Gly Ile Ala Val Val Phe Lys Glu Asn Ile Ala Pro Tyr Lys Phe Lys
145                 150                 155                 160
Ala Thr Met Tyr Tyr Lys Asp Val Thr Val Ser Gln Val Trp Phe Gly
                    165                 170                 175
His Arg Tyr Ser Gln Phe Met Gly Ile Phe Glu Asp Arg Ala Pro Val
            180                 185                 190
Pro Phe Glu Glu Val Ile Asp Lys Ile Asn Ala Lys Gly Val Cys Arg
            195                 200                 205
Ser Thr Ala Lys Tyr Val Arg Asn Asn Leu Glu Thr Thr Ala Phe His
            210                 215                 220
Arg Asp Asp His Glu Thr Asp Met Glu Leu Lys Pro Ala Asn Ala Ala
225                 230                 235                 240
Thr Arg Thr Ser Arg Gly Trp His Thr Thr Asp Leu Lys Tyr Asn Pro
                    245                 250                 255
Ser Arg Val Glu Ala Phe His Arg Tyr Gly Thr Thr Val Asn Cys Ile
            260                 265                 270
Val Glu Glu Val Asp Ala Arg Ser Val Tyr Pro Tyr Asp Glu Phe Val
            275                 280                 285
Leu Ala Thr Gly Asp Phe Val Tyr Met Ser Pro Phe Tyr Gly Tyr Arg
            290                 295                 300
Glu Gly Ser His Thr Glu His Thr Ser Tyr Ala Ala Asp Arg Phe Lys
305                 310                 315                 320
Gln Val Asp Gly Phe Tyr Ala Arg Asp Leu Thr Thr Lys Ala Arg Ala
                    325                 330                 335
Thr Ala Pro Thr Thr Arg Asn Leu Leu Thr Thr Pro Lys Phe Thr Val
            340                 345                 350
Ala Trp Asp Trp Val Pro Lys Arg Pro Ser Val Cys Thr Met Thr Lys
            355                 360                 365
Trp Gln Glu Val Asp Glu Met Leu Arg Ser Glu Tyr Gly Gly Ser Phe
            370                 375                 380
Arg Phe Ser Ser Asp Ala Ile Ser Thr Thr Phe Thr Thr Asn Leu Thr
385                 390                 395                 400
Glu Tyr Pro Leu Ser Arg Val Asp Leu Gly Asp Cys Ile Gly Lys Asp
                    405                 410                 415
Ala Arg Asp Ala Met Asp Arg Ile Phe Ala Arg Arg Tyr Asn Ala Thr
            420                 425                 430
His Ile Lys Val Gly Gln Pro Gln Tyr Tyr Leu Ala Asn Gly Gly Phe
            435                 440                 445
Leu Ile Ala Tyr Gln Pro Leu Leu Ser Asn Thr Leu Ala Glu Leu Tyr
            450                 455                 460
Val Arg Glu His Leu Arg Glu Gln Ser Arg Lys Pro Pro Asn Pro Thr
465                 470                 475                 480
Pro Pro Pro Pro Gly Ala Ser Ala Asn Ala Ser Val Glu Arg Ile Lys
                    485                 490                 495
Thr Thr Ser Ser Ile Glu Phe Ala Arg Leu Gln Phe Thr Tyr Asn His
            500                 505                 510
```

Ile Gln Arg His Val Asn Asp Met Leu Gly Arg Val Ala Ile Ala Trp
            515                 520                 525

Cys Glu Leu Gln Asn His Glu Leu Thr Leu Trp Asn Glu Ala Arg Lys
        530                 535                 540

Leu Asn Pro Asn Ala Ile Ala Ser Ala Thr Val Gly Arg Arg Val Ser
545                 550                 555                 560

Ala Arg Met Leu Gly Asp Val Met Ala Val Ser Thr Cys Val Pro Val
                565                 570                 575

Ala Ala Asp Asn Val Ile Val Gln Asn Ser Met Arg Ile Ser Ser Arg
                580                 585                 590

Pro Gly Ala Cys Tyr Ser Arg Pro Leu Val Ser Phe Arg Tyr Glu Asp
                595                 600                 605

Gln Gly Pro Leu Val Glu Gly Gln Leu Gly Glu Asn Asn Glu Leu Arg
        610                 615                 620

Leu Thr Arg Asp Ala Ile Glu Pro Cys Thr Val Gly His Arg Arg Tyr
625                 630                 635                 640

Phe Thr Phe Gly Gly Gly Tyr Val Tyr Phe Glu Tyr Ala Tyr Ser
                645                 650                 655

His Gln Leu Ser Arg Ala Asp Ile Thr Thr Val Ser Thr Phe Ile Asp
        660                 665                 670

Leu Asn Ile Thr Met Leu Glu Asp His Glu Phe Val Pro Leu Glu Val
        675                 680                 685

Tyr Thr Arg His Glu Ile Lys Asp Ser Gly Leu Leu Asp Tyr Thr Glu
        690                 695                 700

Val Gln Arg Arg Asn Gln Leu His Asp Leu Arg Phe Ala Asp Ile Asp
705                 710                 715                 720

Thr Val Ile His Ala Asp Ala Asn Ala Ala Met Phe Ala Gly Leu Gly
                725                 730                 735

Ala Phe Phe Glu Gly Met Gly Asp Leu Gly Arg Ala Val Gly Lys Val
                740                 745                 750

Val Met Gly Ile Val Gly Gly Val Val Ser Ala Val Ser Gly Val Ser
        755                 760                 765

Ser Phe Met Ser Asn Pro Phe Gly Ala Leu Ala Val Gly Leu Leu Val
        770                 775                 780

Leu Ala Gly Leu Ala Ala Ala Phe Phe Ala Phe Arg Tyr Val Met Arg
785                 790                 795                 800

Leu Gln Ser Asn Pro Met Lys Ala Leu Tyr Pro Leu Thr Thr Lys Glu
                805                 810                 815

Leu Lys Asn Pro Thr Asn Pro Asp Ala Ser Gly Glu Gly Glu Gly
                820                 825                 830

Gly Asp Phe Asp Glu Ala Lys Leu Ala Glu Ala Arg Glu Met Ile Arg
            835                 840                 845

Tyr Met Ala Leu Val Ser Ala Met Glu Arg Thr Glu His Lys Ala Lys
        850                 855                 860

Lys Lys Gly Thr Ser Ala Leu Leu Ser Ala Lys Val Thr Asp Met Val
865                 870                 875                 880

Met Arg Lys Arg Arg Asn Thr Asn Tyr Thr Gln Val Pro Asn Lys Asp
                885                 890                 895

Gly Asp Ala Asp Glu Asp Asp Leu
            900

<210> SEQ ID NO 2
<211> LENGTH: 1163

<212> TYPE: PRT
<213> ORGANISM: Artificial sequence
<220> FEATURE:
<223> OTHER INFORMATION: Amino acid sequence of the precursor of gB
      (SEQ ID NO: 1) having inserted the trastuzumab scFv between amino
      acids 43 and 44, as encoded by constructs R-BP903 and R-BP909

<400> SEQUENCE: 2

```
Met Arg Gln Gly Ala Pro Ala Arg Gly Cys Arg Trp Phe Val Val Trp
1               5                   10                  15

Ala Leu Leu Gly Leu Thr Leu Gly Val Leu Val Ala Ser Ala Ala Pro
            20                  25                  30

Ser Ser Pro Gly Thr Pro Gly Val Ala Ala Ser Asp Ile Gln Met
        35                  40                  45

Thr Gln Ser Pro Ser Ser Leu Ser Ala Ser Val Gly Asp Arg Val Thr
    50                  55                  60

Ile Thr Cys Arg Ala Ser Gln Asp Val Asn Thr Ala Val Ala Trp Tyr
65                  70                  75                  80

Gln Gln Lys Pro Gly Lys Ala Pro Lys Leu Leu Ile Tyr Ser Ala Ser
                85                  90                  95

Phe Leu Tyr Ser Gly Val Pro Ser Arg Phe Ser Gly Ser Arg Ser Gly
            100                 105                 110

Thr Asp Phe Thr Leu Thr Ile Ser Ser Leu Gln Pro Glu Asp Phe Ala
        115                 120                 125

Thr Tyr Tyr Cys Gln Gln His Tyr Thr Thr Pro Pro Thr Phe Gly Gln
    130                 135                 140

Gly Thr Lys Val Glu Ile Lys Ser Asp Met Pro Met Ala Asp Pro Asn
145                 150                 155                 160

Arg Phe Arg Gly Lys Asn Leu Val Phe His Ser Glu Val Gln Leu Val
                165                 170                 175

Glu Ser Gly Gly Gly Leu Val Gln Pro Gly Gly Ser Leu Arg Leu Ser
            180                 185                 190

Cys Ala Ala Ser Gly Phe Asn Ile Lys Asp Thr Tyr Ile His Trp Val
        195                 200                 205

Arg Gln Ala Pro Gly Lys Gly Leu Glu Trp Val Ala Arg Ile Tyr Pro
    210                 215                 220

Thr Asn Gly Tyr Thr Arg Tyr Ala Asp Ser Val Lys Gly Arg Phe Thr
225                 230                 235                 240

Ile Ser Ala Asp Thr Ser Lys Asn Thr Ala Tyr Leu Gln Met Asn Ser
                245                 250                 255

Leu Arg Ala Glu Asp Thr Ala Val Tyr Tyr Cys Ser Arg Trp Gly Gly
            260                 265                 270

Asp Gly Phe Tyr Ala Met Asp Tyr Trp Gly Gln Gly Thr Leu Val Thr
        275                 280                 285

Val Ser Ser Ser Gly Gly Ser Gly Ser Gly Ser Gly Thr Gln
    290                 295                 300

Ala Ala Asn Gly Gly Pro Ala Thr Pro Ala Pro Pro Ala Pro Gly Pro
305                 310                 315                 320

Ala Pro Thr Gly Asp Thr Lys Pro Lys Lys Asn Lys Pro Lys Asn
                325                 330                 335

Pro Pro Pro Pro Arg Pro Ala Gly Asp Asn Ala Thr Val Ala Ala Gly
            340                 345                 350

His Ala Thr Leu Arg Glu His Leu Arg Asp Ile Lys Ala Glu Asn Thr
        355                 360                 365

Asp Ala Asn Phe Tyr Val Cys Pro Pro Pro Thr Gly Ala Thr Val Val
```

```
            370                 375                 380
Gln Phe Glu Gln Pro Arg Arg Cys Pro Thr Arg Pro Glu Gly Gln Asn
385                 390                 395                 400

Tyr Thr Glu Gly Ile Ala Val Val Phe Lys Glu Asn Ile Ala Pro Tyr
                405                 410                 415

Lys Phe Lys Ala Thr Met Tyr Tyr Lys Asp Val Thr Val Ser Gln Val
            420                 425                 430

Trp Phe Gly His Arg Tyr Ser Gln Phe Met Gly Ile Phe Glu Asp Arg
            435                 440                 445

Ala Pro Val Pro Phe Glu Glu Val Ile Asp Lys Ile Asn Ala Lys Gly
450                 455                 460

Val Cys Arg Ser Thr Ala Lys Tyr Val Arg Asn Asn Leu Glu Thr Thr
465                 470                 475                 480

Ala Phe His Arg Asp Asp His Glu Thr Asp Met Glu Leu Lys Pro Ala
                485                 490                 495

Asn Ala Ala Thr Arg Thr Ser Arg Gly Trp His Thr Thr Asp Leu Lys
            500                 505                 510

Tyr Asn Pro Ser Arg Val Glu Ala Phe His Arg Tyr Gly Thr Thr Val
            515                 520                 525

Asn Cys Ile Val Glu Glu Val Asp Ala Arg Ser Val Tyr Pro Tyr Asp
            530                 535                 540

Glu Phe Val Leu Ala Thr Gly Asp Phe Val Tyr Met Ser Pro Phe Tyr
545                 550                 555                 560

Gly Tyr Arg Glu Gly Ser His Thr Glu His Thr Ser Tyr Ala Ala Asp
                565                 570                 575

Arg Phe Lys Gln Val Asp Gly Phe Tyr Ala Arg Asp Leu Thr Thr Lys
            580                 585                 590

Ala Arg Ala Thr Ala Pro Thr Thr Arg Asn Leu Leu Thr Thr Pro Lys
            595                 600                 605

Phe Thr Val Ala Trp Asp Trp Val Pro Lys Arg Pro Ser Val Cys Thr
610                 615                 620

Met Thr Lys Trp Gln Glu Val Asp Glu Met Leu Arg Ser Glu Tyr Gly
625                 630                 635                 640

Gly Ser Phe Arg Phe Ser Ser Asp Ala Ile Ser Thr Thr Phe Thr Thr
                645                 650                 655

Asn Leu Thr Glu Tyr Pro Leu Ser Arg Val Asp Leu Gly Asp Cys Ile
            660                 665                 670

Gly Lys Asp Ala Arg Asp Ala Met Asp Arg Ile Phe Ala Arg Arg Tyr
            675                 680                 685

Asn Ala Thr His Ile Lys Val Gly Gln Pro Gln Tyr Tyr Leu Ala Asn
690                 695                 700

Gly Gly Phe Leu Ile Ala Tyr Gln Pro Leu Leu Ser Asn Thr Leu Ala
705                 710                 715                 720

Glu Leu Tyr Val Arg Glu His Leu Arg Glu Gln Ser Arg Lys Pro Pro
                725                 730                 735

Asn Pro Thr Pro Pro Pro Gly Ala Ser Ala Asn Ala Ser Val Glu
            740                 745                 750

Arg Ile Lys Thr Thr Ser Ser Ile Glu Phe Ala Arg Leu Gln Phe Thr
            755                 760                 765

Tyr Asn His Ile Gln Arg His Val Asn Asp Met Leu Gly Arg Val Ala
            770                 775                 780

Ile Ala Trp Cys Glu Leu Gln Asn His Glu Leu Thr Leu Trp Asn Glu
785                 790                 795                 800
```

Ala Arg Lys Leu Asn Pro Asn Ala Ile Ala Ser Ala Thr Val Gly Arg
            805                 810                 815

Arg Val Ser Ala Arg Met Leu Gly Asp Val Met Ala Val Ser Thr Cys
        820                 825                 830

Val Pro Val Ala Ala Asp Asn Val Ile Val Gln Asn Ser Met Arg Ile
            835                 840                 845

Ser Ser Arg Pro Gly Ala Cys Tyr Ser Arg Pro Leu Val Ser Phe Arg
    850                 855                 860

Tyr Glu Asp Gln Gly Pro Leu Val Glu Gly Gln Leu Gly Glu Asn Asn
865                 870                 875                 880

Glu Leu Arg Leu Thr Arg Asp Ala Ile Glu Pro Cys Thr Val Gly His
                885                 890                 895

Arg Arg Tyr Phe Thr Phe Gly Gly Tyr Val Tyr Phe Glu Glu Tyr
            900                 905                 910

Ala Tyr Ser His Gln Leu Ser Arg Ala Asp Ile Thr Thr Val Ser Thr
            915                 920                 925

Phe Ile Asp Leu Asn Ile Thr Met Leu Glu Asp His Glu Phe Val Pro
    930                 935                 940

Leu Glu Val Tyr Thr Arg His Glu Ile Lys Asp Ser Gly Leu Leu Asp
945                 950                 955                 960

Tyr Thr Glu Val Gln Arg Arg Asn Gln Leu His Asp Leu Arg Phe Ala
                965                 970                 975

Asp Ile Asp Thr Val Ile His Ala Asp Ala Asn Ala Ala Met Phe Ala
            980                 985                 990

Gly Leu Gly Ala Phe Phe Glu Gly Met Gly Asp Leu Gly Arg Ala Val
        995                 1000                1005

Gly Lys Val Val Met Gly Ile Val Gly Gly Val Val Ser Ala Val
    1010                1015                1020

Ser Gly Val Ser Ser Phe Met Ser Asn Pro Phe Gly Ala Leu Ala
    1025                1030                1035

Val Gly Leu Leu Val Leu Ala Gly Leu Ala Ala Ala Phe Phe Ala
    1040                1045                1050

Phe Arg Tyr Val Met Arg Leu Gln Ser Asn Pro Met Lys Ala Leu
    1055                1060                1065

Tyr Pro Leu Thr Thr Lys Glu Leu Lys Asn Pro Thr Asn Pro Asp
    1070                1075                1080

Ala Ser Gly Glu Gly Glu Gly Gly Asp Phe Asp Glu Ala Lys
    1085                1090                1095

Leu Ala Glu Ala Arg Glu Met Ile Arg Tyr Met Ala Leu Val Ser
    1100                1105                1110

Ala Met Glu Arg Thr Glu His Lys Ala Lys Lys Lys Gly Thr Ser
    1115                1120                1125

Ala Leu Leu Ser Ala Lys Val Thr Asp Met Val Met Arg Lys Arg
    1130                1135                1140

Arg Asn Thr Asn Tyr Thr Gln Val Pro Asn Lys Asp Gly Asp Ala
    1145                1150                1155

Asp Glu Asp Asp Leu
    1160

<210> SEQ ID NO 3
<211> LENGTH: 1171
<212> TYPE: PRT
<213> ORGANISM: Artificial sequence
<220> FEATURE:

<223> OTHER INFORMATION: Amino acid sequence of the precursor of gB (SEQ ID NO: 1) having inserted the trastuzumab scFv between amino acids 81 and 82

<400> SEQUENCE: 3

```
Met Arg Gln Gly Ala Pro Ala Arg Gly Cys Arg Trp Phe Val Val Trp
1               5                   10                  15

Ala Leu Leu Gly Leu Thr Leu Gly Val Leu Val Ala Ser Ala Ala Pro
            20                  25                  30

Ser Ser Pro Gly Thr Pro Gly Val Ala Ala Ala Thr Gln Ala Ala Asn
        35                  40                  45

Gly Gly Pro Ala Thr Pro Ala Pro Pro Ala Pro Gly Pro Ala Pro Thr
    50                  55                  60

Gly Asp Thr Lys Pro Lys Lys Asn Lys Lys Pro Lys Asn Pro Pro Pro
65                  70                  75                  80

Pro His Ser Ser Gly Gly Gly Ser Gly Ser Asp Ile Gln Met Thr Gln
                85                  90                  95

Ser Pro Ser Ser Leu Ser Ala Ser Val Gly Asp Arg Val Thr Ile Thr
            100                 105                 110

Cys Arg Ala Ser Gln Asp Val Asn Thr Ala Val Ala Trp Tyr Gln Gln
        115                 120                 125

Lys Pro Gly Lys Ala Pro Lys Leu Leu Ile Tyr Ser Ala Ser Phe Leu
    130                 135                 140

Tyr Ser Gly Val Pro Ser Arg Phe Ser Gly Ser Arg Ser Gly Thr Asp
145                 150                 155                 160

Phe Thr Leu Thr Ile Ser Ser Leu Gln Pro Glu Asp Phe Ala Thr Tyr
                165                 170                 175

Tyr Cys Gln Gln His Tyr Thr Thr Pro Pro Thr Phe Gly Gln Gly Thr
            180                 185                 190

Lys Val Glu Ile Lys Ser Asp Met Pro Met Ala Asp Pro Asn Arg Phe
        195                 200                 205

Arg Gly Lys Asn Leu Val Phe His Ser Glu Val Gln Leu Val Glu Ser
    210                 215                 220

Gly Gly Gly Leu Val Gln Pro Gly Gly Ser Leu Arg Leu Ser Cys Ala
225                 230                 235                 240

Ala Ser Gly Phe Asn Ile Lys Asp Thr Tyr Ile His Trp Val Arg Gln
                245                 250                 255

Ala Pro Gly Lys Gly Leu Glu Trp Val Ala Arg Ile Tyr Pro Thr Asn
            260                 265                 270

Gly Tyr Thr Arg Tyr Ala Asp Ser Val Lys Gly Arg Phe Thr Ile Ser
        275                 280                 285

Ala Asp Thr Ser Lys Asn Thr Ala Tyr Leu Gln Met Asn Ser Leu Arg
    290                 295                 300

Ala Glu Asp Thr Ala Val Tyr Tyr Cys Ser Arg Trp Gly Gly Asp Gly
305                 310                 315                 320

Phe Tyr Ala Met Asp Tyr Trp Gly Gln Gly Thr Leu Val Thr Val Ser
                325                 330                 335

Ser Ser Gly Gly Gly Ser Gly Ser Gly Gly Ser Gly Arg Pro Ala Gly
            340                 345                 350

Asp Asn Ala Thr Val Ala Ala Gly His Ala Thr Leu Arg Glu His Leu
        355                 360                 365

Arg Asp Ile Lys Ala Glu Asn Thr Asp Ala Asn Phe Tyr Val Cys Pro
    370                 375                 380

Pro Pro Thr Gly Ala Thr Val Val Gln Phe Glu Gln Pro Arg Arg Cys
```

-continued

```
            385                 390                 395                 400
Pro Thr Arg Pro Glu Gly Gln Asn Tyr Thr Glu Gly Ile Ala Val Val
                    405                 410                 415
Phe Lys Glu Asn Ile Ala Pro Tyr Lys Phe Lys Ala Thr Met Tyr Tyr
                420                 425                 430
Lys Asp Val Thr Val Ser Gln Val Trp Phe Gly His Arg Tyr Ser Gln
                435                 440                 445
Phe Met Gly Ile Phe Glu Asp Arg Ala Pro Val Pro Phe Glu Glu Val
            450                 455                 460
Ile Asp Lys Ile Asn Ala Lys Gly Val Cys Arg Ser Thr Ala Lys Tyr
465                 470                 475                 480
Val Arg Asn Asn Leu Glu Thr Thr Ala Phe His Arg Asp Asp His Glu
                    485                 490                 495
Thr Asp Met Glu Leu Lys Pro Ala Asn Ala Ala Thr Arg Thr Ser Arg
                500                 505                 510
Gly Trp His Thr Thr Asp Leu Lys Tyr Asn Pro Ser Arg Val Glu Ala
            515                 520                 525
Phe His Arg Tyr Gly Thr Thr Val Asn Cys Ile Val Glu Glu Val Asp
            530                 535                 540
Ala Arg Ser Val Tyr Pro Tyr Asp Glu Phe Val Leu Ala Thr Gly Asp
545                 550                 555                 560
Phe Val Tyr Met Ser Pro Phe Tyr Gly Tyr Arg Glu Gly Ser His Thr
                    565                 570                 575
Glu His Thr Ser Tyr Ala Ala Asp Arg Phe Lys Gln Val Asp Gly Phe
                580                 585                 590
Tyr Ala Arg Asp Leu Thr Thr Lys Ala Arg Ala Thr Ala Pro Thr Thr
                595                 600                 605
Arg Asn Leu Leu Thr Thr Pro Lys Phe Thr Val Ala Trp Asp Trp Val
            610                 615                 620
Pro Lys Arg Pro Ser Val Cys Thr Met Thr Lys Trp Gln Glu Val Asp
625                 630                 635                 640
Glu Met Leu Arg Ser Glu Tyr Gly Gly Ser Phe Arg Phe Ser Ser Asp
                    645                 650                 655
Ala Ile Ser Thr Thr Phe Thr Thr Asn Leu Thr Glu Tyr Pro Leu Ser
                660                 665                 670
Arg Val Asp Leu Gly Asp Cys Ile Gly Lys Asp Ala Arg Asp Ala Met
            675                 680                 685
Asp Arg Ile Phe Ala Arg Arg Tyr Asn Ala Thr His Ile Lys Val Gly
            690                 695                 700
Gln Pro Gln Tyr Tyr Leu Ala Asn Gly Gly Phe Leu Ile Ala Tyr Gln
705                 710                 715                 720
Pro Leu Leu Ser Asn Thr Leu Ala Glu Leu Tyr Val Arg Glu His Leu
                    725                 730                 735
Arg Glu Gln Ser Arg Lys Pro Pro Asn Pro Thr Pro Pro Pro Pro Gly
                740                 745                 750
Ala Ser Ala Asn Ala Ser Val Glu Arg Ile Lys Thr Thr Ser Ser Ile
                755                 760                 765
Glu Phe Ala Arg Leu Gln Phe Thr Tyr Asn His Ile Gln Arg His Val
            770                 775                 780
Asn Asp Met Leu Gly Arg Val Ala Ile Ala Trp Cys Glu Leu Gln Asn
785                 790                 795                 800
His Glu Leu Thr Leu Trp Asn Glu Ala Arg Lys Leu Asn Pro Asn Ala
                    805                 810                 815
```

```
Ile Ala Ser Ala Thr Val Gly Arg Arg Val Ser Ala Arg Met Leu Gly
            820                 825                 830

Asp Val Met Ala Val Ser Thr Cys Val Pro Val Ala Ala Asp Asn Val
            835                 840                 845

Ile Val Gln Asn Ser Met Arg Ile Ser Ser Arg Pro Gly Ala Cys Tyr
850                 855                 860

Ser Arg Pro Leu Val Ser Phe Arg Tyr Glu Asp Gln Gly Pro Leu Val
865                 870                 875                 880

Glu Gly Gln Leu Gly Glu Asn Asn Glu Leu Arg Leu Thr Arg Asp Ala
                885                 890                 895

Ile Glu Pro Cys Thr Val Gly His Arg Arg Tyr Phe Thr Phe Gly Gly
            900                 905                 910

Gly Tyr Val Tyr Phe Glu Glu Tyr Ala Tyr Ser His Gln Leu Ser Arg
        915                 920                 925

Ala Asp Ile Thr Thr Val Ser Thr Phe Ile Asp Leu Asn Ile Thr Met
    930                 935                 940

Leu Glu Asp His Glu Phe Val Pro Leu Glu Val Tyr Thr Arg His Glu
945                 950                 955                 960

Ile Lys Asp Ser Gly Leu Leu Asp Tyr Thr Glu Val Gln Arg Arg Asn
                965                 970                 975

Gln Leu His Asp Leu Arg Phe Ala Asp Ile Asp Thr Val Ile His Ala
            980                 985                 990

Asp Ala Asn Ala Ala Met Phe Ala  Gly Leu Gly Ala Phe  Phe Glu Gly
        995                 1000                1005

Met Gly  Asp Leu Gly Arg Ala  Val Gly Lys Val Val  Met Gly Ile
    1010                1015                1020

Val Gly  Gly Val Val Ser Ala  Val Ser Gly Val Ser  Ser Phe Met
    1025                1030                1035

Ser Asn  Pro Phe Gly Ala Leu  Ala Val Gly Leu Leu  Val Leu Ala
    1040                1045                1050

Gly Leu  Ala Ala Ala Phe Phe  Ala Phe Arg Tyr Val  Met Arg Leu
    1055                1060                1065

Gln Ser  Asn Pro Met Lys Ala  Leu Tyr Pro Leu Thr  Thr Lys Glu
    1070                1075                1080

Leu Lys  Asn Pro Thr Asn Pro  Asp Ala Ser Gly Glu  Gly Glu Glu
    1085                1090                1095

Gly Gly  Asp Phe Asp Glu Ala  Lys Leu Ala Glu Ala  Arg Glu Met
    1100                1105                1110

Ile Arg  Tyr Met Ala Leu Val  Ser Ala Met Glu Arg  Thr Glu His
    1115                1120                1125

Lys Ala  Lys Lys Lys Gly Thr  Ser Ala Leu Leu Ser  Ala Lys Val
    1130                1135                1140

Thr Asp  Met Val Met Arg Lys  Arg Arg Asn Thr Asn  Tyr Thr Gln
    1145                1150                1155

Val Pro  Asn Lys Asp Gly Asp  Ala Asp Glu Asp Asp  Leu
    1160                1165                1170

<210> SEQ ID NO 4
<211> LENGTH: 394
<212> TYPE: PRT
<213> ORGANISM: Herpes simplex virus 1

<400> SEQUENCE: 4

Met Gly Gly Ala Ala Ala Arg Leu Gly Ala Val Ile Leu Phe Val Val
```

```
            1               5              10              15
          Ile Val Gly Leu His Gly Val Arg Gly Lys Tyr Ala Leu Ala Asp Ala
                          20              25              30

Ser Leu Lys Met Ala Asp Pro Asn Arg Phe Arg Gly Lys Asp Leu Pro
                          35              40              45

Val Leu Asp Gln Leu Thr Asp Pro Pro Gly Val Arg Val Tyr His
                          50              55              60

Ile Gln Ala Gly Leu Pro Asp Pro Phe Gln Pro Pro Ser Leu Pro Ile
          65              70              75              80

Thr Val Tyr Tyr Ala Val Leu Glu Arg Ala Cys Arg Ser Val Leu Leu
                          85              90              95

Asn Ala Pro Ser Glu Ala Pro Gln Ile Val Arg Gly Ala Ser Glu Asp
                          100             105             110

Val Arg Lys Gln Pro Tyr Asn Leu Thr Ile Ala Trp Phe Arg Met Gly
                          115             120             125

Gly Asn Cys Ala Ile Pro Ile Thr Val Met Glu Tyr Thr Glu Cys Ser
                          130             135             140

Tyr Asn Lys Ser Leu Gly Ala Cys Pro Ile Arg Thr Gln Pro Arg Trp
          145             150             155             160

Asn Tyr Tyr Asp Ser Phe Ser Ala Val Ser Glu Asp Asn Leu Gly Phe
                          165             170             175

Leu Met His Ala Pro Ala Phe Glu Thr Ala Gly Thr Tyr Leu Arg Leu
                          180             185             190

Val Lys Ile Asn Asp Trp Thr Glu Ile Thr Gln Phe Ile Leu Glu His
                          195             200             205

Arg Ala Lys Gly Ser Cys Lys Tyr Ala Leu Pro Leu Arg Ile Pro Pro
          210             215             220

Ser Ala Cys Leu Ser Pro Gln Ala Tyr Gln Gln Gly Val Thr Val Asp
          225             230             235             240

Ser Ile Gly Met Leu Pro Arg Phe Ile Pro Glu Asn Gln Arg Thr Val
                          245             250             255

Ala Val Tyr Ser Leu Lys Ile Ala Gly Trp His Gly Pro Lys Ala Pro
                          260             265             270

Tyr Thr Ser Thr Leu Leu Pro Pro Glu Leu Ser Glu Thr Pro Asn Ala
                          275             280             285

Thr Gln Pro Glu Leu Ala Pro Glu Asp Pro Glu Asp Ser Ala Leu Leu
                          290             295             300

Glu Asp Pro Val Gly Thr Val Ala Pro Gln Ile Pro Asn Trp His
          305             310             315             320

Ile Pro Ser Ile Gln Asp Ala Ala Thr Pro Tyr His Pro Pro Ala Thr
                          325             330             335

Pro Asn Asn Met Gly Leu Ile Ala Gly Ala Val Gly Gly Ser Leu Leu
                          340             345             350

Ala Ala Leu Val Ile Cys Gly Ile Val Tyr Trp Met Arg Arg Arg Thr
                          355             360             365

Gln Lys Ala Pro Lys Arg Ile Arg Leu Pro His Ile Arg Glu Asp Asp
                          370             375             380

Gln Pro Ser Ser His Gln Pro Leu Phe Tyr
          385             390

<210> SEQ ID NO 5
<211> LENGTH: 361
<212> TYPE: PRT
<213> ORGANISM: Artificial sequence
```

<220> FEATURE:
<223> OTHER INFORMATION: Amino acid sequence of HSV-1 gD wild type, precursor (SEQ ID NO: 4), with deletion of amino acids 31-63, corresponding to amino acids 6 to 38 in mature gD

<400> SEQUENCE: 5

```
Met Gly Gly Ala Ala Arg Leu Gly Ala Val Ile Leu Phe Val Val
1               5                   10                  15

Ile Val Gly Leu His Gly Val Arg Gly Lys Tyr Ala Leu Ala His Ile
            20                  25                  30

Gln Ala Gly Leu Pro Asp Pro Phe Gln Pro Pro Ser Leu Pro Ile Thr
                35                  40                  45

Val Tyr Tyr Ala Val Leu Glu Arg Ala Cys Arg Ser Val Leu Leu Asn
50                  55                  60

Ala Pro Ser Glu Ala Pro Gln Ile Val Arg Gly Ala Ser Glu Asp Val
65                  70                  75                  80

Arg Lys Gln Pro Tyr Asn Leu Thr Ile Ala Trp Phe Arg Met Gly Gly
                85                  90                  95

Asn Cys Ala Ile Pro Ile Thr Val Met Glu Tyr Thr Glu Cys Ser Tyr
                100                 105                 110

Asn Lys Ser Leu Gly Ala Cys Pro Ile Arg Thr Gln Pro Arg Trp Asn
            115                 120                 125

Tyr Tyr Asp Ser Phe Ser Ala Val Ser Glu Asp Asn Leu Gly Phe Leu
130                 135                 140

Met His Ala Pro Ala Phe Glu Thr Ala Gly Thr Tyr Leu Arg Leu Val
145                 150                 155                 160

Lys Ile Asn Asp Trp Thr Glu Ile Thr Gln Phe Ile Leu Glu His Arg
                165                 170                 175

Ala Lys Gly Ser Cys Lys Tyr Ala Leu Pro Leu Arg Ile Pro Pro Ser
            180                 185                 190

Ala Cys Leu Ser Pro Gln Ala Tyr Gln Gln Gly Val Thr Val Asp Ser
            195                 200                 205

Ile Gly Met Leu Pro Arg Phe Ile Pro Glu Asn Gln Arg Thr Val Ala
210                 215                 220

Val Tyr Ser Leu Lys Ile Ala Gly Trp His Gly Pro Lys Ala Pro Tyr
225                 230                 235                 240

Thr Ser Thr Leu Leu Pro Pro Glu Leu Ser Glu Thr Pro Asn Ala Thr
                245                 250                 255

Gln Pro Glu Leu Ala Pro Glu Asp Pro Glu Asp Ser Ala Leu Leu Glu
                260                 265                 270

Asp Pro Val Gly Thr Val Ala Pro Gln Ile Pro Pro Asn Trp His Ile
            275                 280                 285

Pro Ser Ile Gln Asp Ala Ala Thr Pro Tyr His Pro Pro Ala Thr Pro
            290                 295                 300

Asn Asn Met Gly Leu Ile Ala Gly Ala Val Gly Gly Ser Leu Leu Ala
305                 310                 315                 320

Ala Leu Val Ile Cys Gly Ile Val Tyr Trp Met Arg Arg Arg Thr Gln
                325                 330                 335

Lys Ala Pro Lys Arg Ile Arg Leu Pro His Ile Arg Glu Asp Asp Gln
                340                 345                 350

Pro Ser Ser His Gln Pro Leu Phe Tyr
                355                 360
```

<210> SEQ ID NO 6
<211> LENGTH: 621

<212> TYPE: PRT
<213> ORGANISM: Artificial sequence
<220> FEATURE:
<223> OTHER INFORMATION: Amino acid sequence of HSV-1 gD wild type,
      precursor (SEQ ID NO: 4), having inserted the trastuzumab scFv
      between amino acids 30-64, corresponding to amino acids 5-39 of
      mature gD

<400> SEQUENCE: 6

```
Met Gly Gly Ala Ala Arg Leu Gly Ala Val Ile Leu Phe Val Val
1               5                   10                  15

Ile Val Gly Leu His Gly Val Arg Gly Lys Tyr Ala Leu Ala Glu Asn
            20                  25                  30

Ser Asp Ile Gln Met Thr Gln Ser Pro Ser Ser Leu Ser Ala Ser Val
        35                  40                  45

Gly Asp Arg Val Thr Ile Thr Cys Arg Ala Ser Gln Asp Val Asn Thr
50                  55                  60

Ala Val Ala Trp Tyr Gln Gln Lys Pro Gly Lys Ala Pro Lys Leu Leu
65                  70                  75                  80

Ile Tyr Ser Ala Ser Phe Leu Tyr Ser Gly Val Pro Ser Arg Phe Ser
                85                  90                  95

Gly Ser Arg Ser Gly Thr Asp Phe Thr Leu Thr Ile Ser Ser Leu Gln
            100                 105                 110

Pro Glu Asp Phe Ala Thr Tyr Tyr Cys Gln Gln His Tyr Thr Thr Pro
        115                 120                 125

Pro Thr Phe Gly Gln Gly Thr Lys Val Glu Ile Lys Ser Asp Met Pro
130                 135                 140

Met Ala Asp Pro Asn Arg Phe Arg Gly Lys Asn Leu Val Phe His Ser
145                 150                 155                 160

Glu Val Gln Leu Val Glu Ser Gly Gly Gly Leu Val Gln Pro Gly Gly
                165                 170                 175

Ser Leu Arg Leu Ser Cys Ala Ala Ser Gly Phe Asn Ile Lys Asp Thr
            180                 185                 190

Tyr Ile His Trp Val Arg Gln Ala Pro Gly Lys Gly Leu Glu Trp Val
        195                 200                 205

Ala Arg Ile Tyr Pro Thr Asn Gly Tyr Thr Arg Tyr Ala Asp Ser Val
210                 215                 220

Lys Gly Arg Phe Thr Ile Ser Ala Asp Thr Ser Lys Asn Thr Ala Tyr
225                 230                 235                 240

Leu Gln Met Asn Ser Leu Arg Ala Glu Asp Thr Ala Val Tyr Tyr Cys
                245                 250                 255

Ser Arg Trp Gly Gly Asp Gly Phe Tyr Ala Met Asp Tyr Trp Gly Gln
            260                 265                 270

Gly Thr Leu Val Thr Val Ser Ser Gly Gly Gly Ser Gly Ser Gly
        275                 280                 285

Gly Ser His Ile Gln Ala Gly Leu Pro Asp Pro Phe Gln Pro Pro Ser
290                 295                 300

Leu Pro Ile Thr Val Tyr Tyr Ala Val Leu Glu Arg Ala Cys Arg Ser
305                 310                 315                 320

Val Leu Leu Asn Ala Pro Ser Glu Ala Pro Gln Ile Val Arg Gly Ala
                325                 330                 335

Ser Glu Asp Val Arg Lys Gln Pro Tyr Asn Leu Thr Ile Ala Trp Phe
            340                 345                 350

Arg Met Gly Gly Asn Cys Ala Ile Pro Ile Thr Val Met Glu Tyr Thr
        355                 360                 365
```

| Glu Cys Ser Tyr Asn Lys Ser Leu Gly Ala Cys Pro Ile Arg Thr Gln |
|---|
| 370 375 380 |

Pro Arg Trp Asn Tyr Tyr Asp Ser Phe Ser Ala Val Ser Glu Asp Asn
385          390                395                400

Leu Gly Phe Leu Met His Ala Pro Ala Phe Glu Thr Ala Gly Thr Tyr
            405                410                415

Leu Arg Leu Val Lys Ile Asn Asp Trp Thr Glu Ile Thr Gln Phe Ile
                420                425                430

Leu Glu His Arg Ala Lys Gly Ser Cys Lys Tyr Ala Leu Pro Leu Arg
        435                440                445

Ile Pro Pro Ser Ala Cys Leu Ser Pro Gln Ala Tyr Gln Gln Gly Val
450                455                460

Thr Val Asp Ser Ile Gly Met Leu Pro Arg Phe Ile Pro Glu Asn Gln
465                470                475                480

Arg Thr Val Ala Val Tyr Ser Leu Lys Ile Ala Gly Trp His Gly Pro
                485                490                495

Lys Ala Pro Tyr Thr Ser Thr Leu Leu Pro Pro Glu Leu Ser Glu Thr
            500                505                510

Pro Asn Ala Thr Gln Pro Glu Leu Ala Pro Glu Asp Pro Glu Asp Ser
        515                520                525

Ala Leu Leu Glu Asp Pro Val Gly Thr Val Ala Pro Gln Ile Pro Pro
530                535                540

Asn Trp His Ile Pro Ser Ile Gln Asp Ala Ala Thr Pro Tyr His Pro
545                550                555                560

Pro Ala Thr Pro Asn Asn Met Gly Leu Ile Ala Gly Ala Val Gly Gly
                565                570                575

Ser Leu Leu Ala Ala Leu Val Ile Cys Gly Ile Val Tyr Trp Met Arg
            580                585                590

Arg Arg Thr Gln Lys Ala Pro Lys Arg Ile Arg Leu Pro His Ile Arg
        595                600                605

Glu Asp Asp Gln Pro Ser Ser His Gln Pro Leu Phe Tyr
610                615                620

<210> SEQ ID NO 7
<211> LENGTH: 801
<212> TYPE: DNA
<213> ORGANISM: Artificial sequence
<220> FEATURE:
<223> OTHER INFORMATION: pSG-ScFvHER2-SG trastuzumab scFv cassette
      bracketed by Ser-Gly linkers as in R-BP901

<400> SEQUENCE: 7

```
catagtagtg gcggtggctc tggatccgat atccagatga cccagtcccc gagctccctg      60
tccgcctctg tgggcgatag ggtcaccatc acctgccgtg ccagtcagga tgtgaatact     120
gctgtagcct ggtatcaaca gaaaccagga aaagctccga agcttctgat ttactcggca     180
tccttcctct actctggagt cccttctcgc ttctctggta gccgttccgg gacggatttc     240
actctgacca tcagcagtct gcagccggaa gacttcgcaa cttattactg tcagcaacat     300
tatactactc ctcccacgtt cggacagggt accaaggtgg agatcaaatc ggatatgccg     360
atggctgatc cgaaccgttt ccgcggtaag aacctggttt tcattctga ggttcagctg     420
gtggagtctg gcggtggcct ggtgcagcca gggggctcac tccgtttgtc ctgtgcagct     480
tctggcttca acattaaaga cacctatata cactgggtgc gtcaggcccc gggtaagggc     540
ctggaatggg ttgcaaggat ttatcctacg aatggttata ctagatatgc cgatagcgtc     600
```
aagggccgtt tcactataag cgcagacaca tccaaaaaca cagcctacct acaaatgaac    660
agcttaagag ctgaggacac tgccgtctat tattgtagcc gctggggagg ggacggcttc    720
tatgctatgg actactgggg tcaaggaaca ctagtcaccg tctcctcgag tggcggtggc    780
tctggttccg gtggatccgg t                                              801

<210> SEQ ID NO 8
<211> LENGTH: 267
<212> TYPE: PRT
<213> ORGANISM: Artificial sequence
<220> FEATURE:
<223> OTHER INFORMATION: pSG-ScFvHER2-SG trastuzumab scFV bracketed by
      Ser-Gly linkers as in R-BP901

<400> SEQUENCE: 8

His Ser Ser Gly Gly Gly Ser Gly Ser Asp Ile Gln Met Thr Gln Ser
1               5                   10                  15

Pro Ser Ser Leu Ser Ala Ser Val Gly Asp Arg Val Thr Ile Thr Cys
            20                  25                  30

Arg Ala Ser Gln Asp Val Asn Thr Ala Val Ala Trp Tyr Gln Gln Lys
        35                  40                  45

Pro Gly Lys Ala Pro Lys Leu Leu Ile Tyr Ser Ala Ser Phe Leu Tyr
    50                  55                  60

Ser Gly Val Pro Ser Arg Phe Ser Gly Ser Arg Ser Gly Thr Asp Phe
65                  70                  75                  80

Thr Leu Thr Ile Ser Ser Leu Gln Pro Glu Asp Phe Ala Thr Tyr Tyr
                85                  90                  95

Cys Gln Gln His Tyr Thr Thr Pro Pro Thr Phe Gly Gln Gly Thr Lys
            100                 105                 110

Val Glu Ile Lys Ser Asp Met Pro Met Ala Asp Pro Asn Arg Phe Arg
        115                 120                 125

Gly Lys Asn Leu Val Phe His Ser Glu Val Gln Leu Val Glu Ser Gly
    130                 135                 140

Gly Gly Leu Val Gln Pro Gly Gly Ser Leu Arg Leu Ser Cys Ala Ala
145                 150                 155                 160

Ser Gly Phe Asn Ile Lys Asp Thr Tyr Ile His Trp Val Arg Gln Ala
                165                 170                 175

Pro Gly Lys Gly Leu Glu Trp Val Ala Arg Ile Tyr Pro Thr Asn Gly
            180                 185                 190

Tyr Thr Arg Tyr Ala Asp Ser Val Lys Gly Arg Phe Thr Ile Ser Ala
        195                 200                 205

Asp Thr Ser Lys Asn Thr Ala Tyr Leu Gln Met Asn Ser Leu Arg Ala
    210                 215                 220

Glu Asp Thr Ala Val Tyr Tyr Cys Ser Arg Trp Gly Gly Asp Gly Phe
225                 230                 235                 240

Tyr Ala Met Asp Tyr Trp Gly Gln Gly Thr Leu Val Thr Val Ser Ser
                245                 250                 255

Ser Gly Gly Gly Ser Gly Ser Gly Gly Ser Gly
            260                 265

<210> SEQ ID NO 9
<211> LENGTH: 777
<212> TYPE: DNA
<213> ORGANISM: Artificial sequence
<220> FEATURE:
<223> OTHER INFORMATION: Trastuzumab scFv cassette present in R-BP901,
      but lacking the 8 residues long Ser-Gly upstream linker

<400> SEQUENCE: 9

```
tccgatatcc agatgaccca gtccccgagc tccctgtccg cctctgtggg cgatagggtc    60
accatcacct gccgtgccag tcaggatgtg aatactgctg tagcctggta tcaacagaaa   120
ccaggaaaag ctccgaagct tctgatttac tcggcatcct tcctctactc tggagtccct   180
tctcgcttct ctggtagccg ttccgggacg gatttcactc tgaccatcag cagtctgcag   240
ccggaagact tcgcaactta ttactgtcag caacattata ctactcctcc acgttcgga   300
cagggtacca aggtggagat caaatcggat atgccgatgg ctgatccgaa ccgtttccgc   360
ggtaagaacc tggttttca ttctgaggtt cagctggtgg agtctggcgg tggcctggtg   420
cagccagggg gctcactccg tttgtcctgt gcagcttctg gcttcaacat aaagacacc   480
tatatacact gggtgcgtca ggccccgggt aagggcctgg aatgggttgc aaggatttat   540
cctacgaatg gttatactag atatgccgat agcgtcaagg gccgtttcac tataagcgca   600
gacacatcca aaacacagc ctacctacaa atgaacagct aagagctga ggacactgcc   660
gtctattatt gtagccgctg ggagggggac ggcttctatg ctatggacta ctggggtcaa   720
ggaacactag tcaccgtctc ctcgagtggc ggtggctctg gttccggtgg atccggt     777
```

<210> SEQ ID NO 10
<211> LENGTH: 259
<212> TYPE: PRT
<213> ORGANISM: Artificial sequence
<220> FEATURE:
<223> OTHER INFORMATION: pSG-ScFvHER2-SG trastuzumab scFV with downstream Ser-Gly linker as in R-BP903 and R-BP909

<400> SEQUENCE: 10

```
Ser Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Asp Val Asn Thr
            20                  25                  30

Ala Val Ala Trp Tyr Gln Gln Lys Pro Gly Lys Ala Pro Lys Leu Leu
        35                  40                  45

Ile Tyr Ser Ala Ser Phe Leu Tyr Ser Gly Val Pro Ser Arg Phe Ser
    50                  55                  60

Gly Ser Arg Ser Gly Thr Asp Phe Thr Leu Thr Ile Ser Ser Leu Gln
65                  70                  75                  80

Pro Glu Asp Phe Ala Thr Tyr Tyr Cys Gln Gln His Tyr Thr Thr Pro
                85                  90                  95

Pro Thr Phe Gly Gln Gly Thr Lys Val Glu Ile Lys Ser Asp Met Pro
            100                 105                 110

Met Ala Asp Pro Asn Arg Phe Arg Gly Lys Asn Leu Val Phe His Ser
        115                 120                 125

Glu Val Gln Leu Val Glu Ser Gly Gly Gly Leu Val Gln Pro Gly Gly
    130                 135                 140

Ser Leu Arg Leu Ser Cys Ala Ala Ser Gly Phe Asn Ile Lys Asp Thr
145                 150                 155                 160

Tyr Ile His Trp Val Arg Gln Ala Pro Gly Lys Gly Leu Glu Trp Val
                165                 170                 175

Ala Arg Ile Tyr Pro Thr Asn Gly Tyr Thr Arg Tyr Ala Asp Ser Val
            180                 185                 190

Lys Gly Arg Phe Thr Ile Ser Ala Asp Thr Ser Lys Asn Thr Ala Tyr
        195                 200                 205

Leu Gln Met Asn Ser Leu Arg Ala Glu Asp Thr Ala Val Tyr Tyr Cys
```

```
                210              215              220
    Ser Arg Trp Gly Gly Asp Gly Phe Tyr Ala Met Asp Tyr Trp Gly Gln
    225                 230                 235                 240

Gly Thr Leu Val Thr Val Ser Ser Gly Gly Gly Ser Gly Ser Gly
                        245                 250                 255

Gly Ser Gly

<210> SEQ ID NO 11
<211> LENGTH: 76
<212> TYPE: DNA
<213> ORGANISM: Artificial sequence
<220> FEATURE:
<223> OTHER INFORMATION: gB43GalKfor

<400> SEQUENCE: 11
ggtggcgtcg gcggctccga gttcccccgg cacgcctggg gtcgcggccg cgcctgttga      60
caattaatca tcggca                                                     76

<210> SEQ ID NO 12
<211> LENGTH: 72
<212> TYPE: DNA
<213> ORGANISM: Artificial sequence
<220> FEATURE:
<223> OTHER INFORMATION: gB43GalKrev

<400> SEQUENCE: 12
ggccaggggc gggcggcgcc ggagtggcag gtcccccgtt cgccgcctgg gttcagcact      60
gtcctgctcc tt                                                         72

<210> SEQ ID NO 13
<211> LENGTH: 79
<212> TYPE: DNA
<213> ORGANISM: Artificial sequence
<220> FEATURE:
<223> OTHER INFORMATION: gB43_sc4D5_for

<400> SEQUENCE: 13
ggtggcgtcg gcggctccga gttcccccgg cacgcctggg gtcgcggccg cgtccgatat      60
ccagatgacc cagtccccg                                                  79

<210> SEQ ID NO 14
<211> LENGTH: 76
<212> TYPE: DNA
<213> ORGANISM: Artificial sequence
<220> FEATURE:
<223> OTHER INFORMATION: gB43_sc4D5_rev

<400> SEQUENCE: 14
ggccaggggc gggcggcgcc ggagtggcag gtcccccgtt cgccgcctgg gtaccggatc      60
caccggaacc agagcc                                                     76

<210> SEQ ID NO 15
<211> LENGTH: 77
<212> TYPE: DNA
<213> ORGANISM: Artificial sequence
<220> FEATURE:
<223> OTHER INFORMATION: gB81fGALK

<400> SEQUENCE: 15
cgggggacac gaaaccgaag aagaacaaaa aaccgaaaaa cccaccgccg ccgcctgttg      60
acaattaatc atcggca                                                    77
```

<210> SEQ ID NO 16
<211> LENGTH: 70
<212> TYPE: DNA
<213> ORGANISM: Artificial sequence
<220> FEATURE:
<223> OTHER INFORMATION: gB81GALKrev

<400> SEQUENCE: 16
cgcagggtgg cgtggcccgc ggcgacggtc gcgttgtcgc cggcggggcg tcagcactgt    60
cctgctcctt                                                          70

<210> SEQ ID NO 17
<211> LENGTH: 81
<212> TYPE: DNA
<213> ORGANISM: Artificial sequence
<220> FEATURE:
<223> OTHER INFORMATION: gB81sc4D5f

<400> SEQUENCE: 17
cgggggacac gaaaccgaag aagaacaaaa aaccgaaaaa cccaccgccg ccgcatagta    60
gtggcggtgg ctctggatcc g                                             81

<210> SEQ ID NO 18
<211> LENGTH: 74
<212> TYPE: DNA
<213> ORGANISM: Artificial sequence
<220> FEATURE:
<223> OTHER INFORMATION: gB81SGr

<400> SEQUENCE: 18
cgcagggtgg cgtggcccgc ggcgacggtc gcgttgtcgc cggcggggcg accggatcca    60
ccggaaccag agcc                                                     74

<210> SEQ ID NO 19
<211> LENGTH: 25
<212> TYPE: DNA
<213> ORGANISM: Artificial sequence
<220> FEATURE:
<223> OTHER INFORMATION: scFv4D5_358_r

<400> SEQUENCE: 19
ggaaacggtt cggatcagcc atcgg                                         25

<210> SEQ ID NO 20
<211> LENGTH: 26
<212> TYPE: DNA
<213> ORGANISM: Artificial sequence
<220> FEATURE:
<223> OTHER INFORMATION: scFv4D5_315_f

<400> SEQUENCE: 20
ggagatcaaa tcggatatgc cgatgg                                        26

<210> SEQ ID NO 21
<211> LENGTH: 74
<212> TYPE: DNA
<213> ORGANISM: Artificial sequence
<220> FEATURE:
<223> OTHER INFORMATION: gD5_galK_f

<400> SEQUENCE: 21
ttgtcgtcat agtgggcctc catggggtcc gcggcaaata tgccttggcg cctgttgaca    60

-continued

```
attaatcatc ggca                                                    74

<210> SEQ ID NO 22
<211> LENGTH: 70
<212> TYPE: DNA
<213> ORGANISM: Artificial sequence
<220> FEATURE:
<223> OTHER INFORMATION: gD39_galK_r

<400> SEQUENCE: 22
atcgggaggc tgggggggctg aacgggtcc ggtaggcccg cctggatgtg tcagcactgt   60
cctgctcctt                                                         70

<210> SEQ ID NO 23
<211> LENGTH: 100
<212> TYPE: DNA
<213> ORGANISM: Artificial sequence
<220> FEATURE:
<223> OTHER INFORMATION: gD_aa5_39_f

<400> SEQUENCE: 23
ttgtcgtcat agtgggcctc catggggtcc gcggcaaata tgccttggcg cacatccagg   60
cgggcctacc ggacccgttc cagcccccca gcctcccgat                        100

<210> SEQ ID NO 24
<211> LENGTH: 100
<212> TYPE: DNA
<213> ORGANISM: Artificial sequence
<220> FEATURE:
<223> OTHER INFORMATION: gD_aa5_39_r

<400> SEQUENCE: 24
atcgggaggc tgggggggctg aacgggtcc ggtaggcccg cctggatgtg cgccaaggca   60
tatttgccgc ggaccccatg gaggcccact atgacgacaa                       100

<210> SEQ ID NO 25
<211> LENGTH: 27
<212> TYPE: DNA
<213> ORGANISM: Artificial sequence
<220> FEATURE:
<223> OTHER INFORMATION: galK_129_f

<400> SEQUENCE: 25
acaatctctg tttgccaacg catttgg                                      27

<210> SEQ ID NO 26
<211> LENGTH: 27
<212> TYPE: DNA
<213> ORGANISM: Artificial sequence
<220> FEATURE:
<223> OTHER INFORMATION: galK_417_r

<400> SEQUENCE: 26
cattgccgct gatcaccatg tccacgc                                      27

<210> SEQ ID NO 27
<211> LENGTH: 23
<212> TYPE: DNA
<213> ORGANISM: Artificial sequence
<220> FEATURE:
<223> OTHER INFORMATION: gB_ext_f

<400> SEQUENCE: 27
gagcgccccc gacggctgta tcg                                          23
```

<210> SEQ ID NO 28
<211> LENGTH: 22
<212> TYPE: DNA
<213> ORGANISM: Artificial sequence
<220> FEATURE:
<223> OTHER INFORMATION: gB_431_r

<400> SEQUENCE: 28
ttgaagacca ccgcgatgcc ct                                              22

<210> SEQ ID NO 29
<211> LENGTH: 8
<212> TYPE: PRT
<213> ORGANISM: Artificial sequence
<220> FEATURE:
<223> OTHER INFORMATION: Linker

<400> SEQUENCE: 29

His Ser Ser Gly Gly Gly Ser Gly
1               5

<210> SEQ ID NO 30
<211> LENGTH: 12
<212> TYPE: PRT
<213> ORGANISM: Artificial sequence
<220> FEATURE:
<223> OTHER INFORMATION: Linker

<400> SEQUENCE: 30

Ser Ser Gly Gly Gly Ser Gly Ser Gly Gly Ser Gly
1               5                   10

<210> SEQ ID NO 31
<211> LENGTH: 20
<212> TYPE: PRT
<213> ORGANISM: Artificial sequence
<220> FEATURE:
<223> OTHER INFORMATION: Linker

<400> SEQUENCE: 31

Ser Asp Met Pro Met Ala Asp Pro Asn Arg Phe Arg Gly Lys Asn Leu
1               5                   10                  15

Val Phe His Ser
            20

<210> SEQ ID NO 32
<211> LENGTH: 246
<212> TYPE: PRT
<213> ORGANISM: Artificial sequence
<220> FEATURE:
<223> OTHER INFORMATION: Trastuzumab scFv to HER2

<400> SEQUENCE: 32

Ser Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Asp Val Asn Thr
            20                  25                  30

Ala Val Ala Trp Tyr Gln Gln Lys Pro Gly Lys Ala Pro Lys Leu Leu
        35                  40                  45

Ile Tyr Ser Ala Ser Phe Leu Tyr Ser Gly Val Pro Ser Arg Phe Ser
    50                  55                  60

Gly Ser Arg Ser Gly Thr Asp Phe Thr Leu Thr Ile Ser Ser Leu Gln
65                  70                  75                  80

Pro Glu Asp Phe Ala Thr Tyr Tyr Cys Gln Gln His Tyr Thr Thr Pro
                85                  90                  95

Pro Thr Phe Gly Gln Gly Thr Lys Val Glu Ile Lys Ser Asp Met Pro
            100                 105                 110

Met Ala Asp Pro Asn Arg Phe Arg Gly Lys Asn Leu Val Phe His Ser
        115                 120                 125

Glu Val Gln Leu Val Glu Ser Gly Gly Leu Val Gln Pro Gly Gly
    130                 135                 140

Ser Leu Arg Leu Ser Cys Ala Ala Ser Gly Phe Asn Ile Lys Asp Thr
145                 150                 155                 160

Tyr Ile His Trp Val Arg Gln Ala Pro Gly Lys Gly Leu Glu Trp Val
                165                 170                 175

Ala Arg Ile Tyr Pro Thr Asn Gly Tyr Thr Arg Tyr Ala Asp Ser Val
            180                 185                 190

Lys Gly Arg Phe Thr Ile Ser Ala Asp Thr Ser Lys Asn Thr Ala Tyr
        195                 200                 205

Leu Gln Met Asn Ser Leu Arg Ala Glu Asp Thr Ala Val Tyr Tyr Cys
    210                 215                 220

Ser Arg Trp Gly Gly Asp Gly Phe Tyr Ala Met Asp Tyr Trp Gly Gln
225                 230                 235                 240

Gly Thr Leu Val Thr Val
                245

<210> SEQ ID NO 33
<211> LENGTH: 112
<212> TYPE: DNA
<213> ORGANISM: Artificial sequence
<220> FEATURE:
<223> OTHER INFORMATION: GCN4gB_43_44_fB

<400> SEQUENCE: 33
ggtggcgtcg gcggctccga gttccccgg cacgcctggg gtcgcggccg cgggatccaa      60
gaactaccac ctggagaacg aggtggccag actgaagaag ctggtgggca gc            112

<210> SEQ ID NO 34
<211> LENGTH: 112
<212> TYPE: DNA
<213> ORGANISM: Artificial sequence
<220> FEATURE:
<223> OTHER INFORMATION: GCN4gB_43_44_rB

<400> SEQUENCE: 34 ggccagggc gggcggcgcc ggagtggcag gtccccgtt cgccgcctgg gtgctgccca      60
ccagcttctt cagtctggcc acctcgttct ccaggtggta gttcttggat cc            112

<210> SEQ ID NO 35
<211> LENGTH: 924
<212> TYPE: PRT
<213> ORGANISM: Artificial sequence
<220> FEATURE:
<223> OTHER INFORMATION: Amino acid sequence of the precursor of gB (SEQ
      ID NO: 1) having inserted the GCN4 peptide between amino acids 43
      and 44, as encoded by construct R-313

<400> SEQUENCE: 35

Met Arg Gln Gly Ala Pro Ala Arg Gly Cys Arg Trp Phe Val Val Trp
1               5                   10                  15

Ala Leu Leu Gly Leu Thr Leu Gly Val Leu Val Ala Ser Ala Ala Pro
            20                  25                  30

-continued

```
Ser Ser Pro Gly Thr Pro Gly Val Ala Ala Gly Ser Lys Asn Tyr
        35                  40                  45

His Leu Glu Asn Glu Val Ala Arg Leu Lys Lys Leu Val Gly Ser Thr
 50                  55                  60

Gln Ala Ala Asn Gly Gly Pro Ala Thr Pro Ala Pro Pro Ala Pro Gly
 65                  70                  75                  80

Pro Ala Pro Thr Gly Asp Thr Lys Pro Lys Lys Asn Lys Lys Pro Lys
                 85                  90                  95

Asn Pro Pro Pro Arg Pro Ala Gly Asp Asn Ala Thr Val Ala Ala
                100                 105                 110

Gly His Ala Thr Leu Arg Glu His Leu Arg Asp Ile Lys Ala Glu Asn
            115                 120                 125

Thr Asp Ala Asn Phe Tyr Val Cys Pro Pro Thr Gly Ala Thr Val
130                 135                 140

Val Gln Phe Glu Gln Pro Arg Arg Cys Pro Thr Arg Pro Glu Gly Gln
145                 150                 155                 160

Asn Tyr Thr Glu Gly Ile Ala Val Val Phe Lys Glu Asn Ile Ala Pro
                165                 170                 175

Tyr Lys Phe Lys Ala Thr Met Tyr Tyr Lys Asp Val Thr Val Ser Gln
                180                 185                 190

Val Trp Phe Gly His Arg Tyr Ser Gln Phe Met Gly Ile Phe Glu Asp
            195                 200                 205

Arg Ala Pro Val Pro Phe Glu Glu Val Ile Asp Lys Ile Asn Ala Lys
210                 215                 220

Gly Val Cys Arg Ser Thr Ala Lys Tyr Val Arg Asn Asn Leu Glu Thr
225                 230                 235                 240

Thr Ala Phe His Arg Asp Asp His Glu Thr Asp Met Glu Leu Lys Pro
                245                 250                 255

Ala Asn Ala Ala Thr Arg Thr Ser Arg Gly Trp His Thr Thr Asp Leu
                260                 265                 270

Lys Tyr Asn Pro Ser Arg Val Glu Ala Phe His Arg Tyr Gly Thr Thr
            275                 280                 285

Val Asn Cys Ile Val Glu Glu Val Asp Ala Arg Ser Val Tyr Pro Tyr
290                 295                 300

Asp Glu Phe Val Leu Ala Thr Gly Asp Phe Val Tyr Met Ser Pro Phe
305                 310                 315                 320

Tyr Gly Tyr Arg Glu Gly Ser His Thr Glu His Thr Ser Tyr Ala Ala
                325                 330                 335

Asp Arg Phe Lys Gln Val Asp Gly Phe Tyr Ala Arg Asp Leu Thr Thr
            340                 345                 350

Lys Ala Arg Ala Thr Ala Pro Thr Thr Arg Asn Leu Leu Thr Thr Pro
            355                 360                 365

Lys Phe Thr Val Ala Trp Asp Trp Val Pro Lys Arg Pro Ser Val Cys
    370                 375                 380

Thr Met Thr Lys Trp Gln Glu Val Asp Glu Met Leu Arg Ser Glu Tyr
385                 390                 395                 400

Gly Gly Ser Phe Arg Phe Ser Ser Asp Ala Ile Ser Thr Thr Phe Thr
                405                 410                 415

Thr Asn Leu Thr Glu Tyr Pro Leu Ser Arg Val Asp Leu Gly Asp Cys
            420                 425                 430

Ile Gly Lys Asp Ala Arg Asp Ala Met Asp Arg Ile Phe Ala Arg Arg
            435                 440                 445
```

```
Tyr Asn Ala Thr His Ile Lys Val Gly Gln Pro Gln Tyr Tyr Leu Ala
450                 455                 460

Asn Gly Gly Phe Leu Ile Ala Tyr Gln Pro Leu Leu Ser Asn Thr Leu
465                 470                 475                 480

Ala Glu Leu Tyr Val Arg Glu His Leu Arg Glu Gln Ser Arg Lys Pro
                485                 490                 495

Pro Asn Pro Thr Pro Pro Pro Gly Ala Ser Ala Asn Ala Ser Val
                500                 505                 510

Glu Arg Ile Lys Thr Thr Ser Ser Ile Glu Phe Ala Arg Leu Gln Phe
                515                 520                 525

Thr Tyr Asn His Ile Gln Arg His Val Asn Asp Met Leu Gly Arg Val
530                 535                 540

Ala Ile Ala Trp Cys Glu Leu Gln Asn His Glu Leu Thr Leu Trp Asn
545                 550                 555                 560

Glu Ala Arg Lys Leu Asn Pro Asn Ala Ile Ala Ser Ala Thr Val Gly
                565                 570                 575

Arg Arg Val Ser Ala Arg Met Leu Gly Asp Val Met Ala Val Ser Thr
                580                 585                 590

Cys Val Pro Val Ala Ala Asp Asn Val Ile Val Gln Asn Ser Met Arg
                595                 600                 605

Ile Ser Ser Arg Pro Gly Ala Cys Tyr Ser Arg Pro Leu Val Ser Phe
610                 615                 620

Arg Tyr Glu Asp Gln Gly Pro Leu Val Glu Gly Gln Leu Gly Glu Asn
625                 630                 635                 640

Asn Glu Leu Arg Leu Thr Arg Asp Ala Ile Glu Pro Cys Thr Val Gly
                645                 650                 655

His Arg Arg Tyr Phe Thr Phe Gly Gly Gly Tyr Val Tyr Phe Glu Glu
                660                 665                 670

Tyr Ala Tyr Ser His Gln Leu Ser Arg Ala Asp Ile Thr Thr Val Ser
                675                 680                 685

Thr Phe Ile Asp Leu Asn Ile Thr Met Leu Glu Asp His Glu Phe Val
690                 695                 700

Pro Leu Glu Val Tyr Thr Arg His Glu Ile Lys Asp Ser Gly Leu Leu
705                 710                 715                 720

Asp Tyr Thr Glu Val Gln Arg Arg Asn Gln Leu His Asp Leu Arg Phe
                725                 730                 735

Ala Asp Ile Asp Thr Val Ile His Ala Asp Ala Asn Ala Ala Met Phe
                740                 745                 750

Ala Gly Leu Gly Ala Phe Phe Glu Gly Met Gly Asp Leu Gly Arg Ala
                755                 760                 765

Val Gly Lys Val Val Met Gly Ile Val Gly Gly Val Val Ser Ala Val
                770                 775                 780

Ser Gly Val Ser Ser Phe Met Ser Asn Pro Phe Gly Ala Leu Ala Val
785                 790                 795                 800

Gly Leu Leu Val Leu Ala Gly Leu Ala Ala Phe Phe Ala Phe Arg
                805                 810                 815

Tyr Val Met Arg Leu Gln Ser Asn Pro Met Lys Ala Leu Tyr Pro Leu
                820                 825                 830

Thr Thr Lys Glu Leu Lys Asn Pro Thr Asn Pro Asp Ala Ser Gly Glu
                835                 840                 845

Gly Glu Glu Gly Gly Asp Phe Asp Glu Ala Lys Leu Ala Glu Ala Arg
850                 855                 860

Glu Met Ile Arg Tyr Met Ala Leu Val Ser Ala Met Glu Arg Thr Glu
```

```
                    865                 870                 875                 880
His Lys Ala Lys Lys Lys Gly Thr Ser Ala Leu Leu Ser Ala Lys Val
                885                 890                 895
Thr Asp Met Val Met Arg Lys Arg Arg Asn Thr Asn Tyr Thr Gln Val
            900                 905                 910
Pro Asn Lys Asp Gly Asp Ala Asp Glu Asp Leu
        915                 920

<210> SEQ ID NO 36
<211> LENGTH: 60
<212> TYPE: DNA
<213> ORGANISM: Artificial sequence
<220> FEATURE:
<223> OTHER INFORMATION: GCN4 peptide cassette

<400> SEQUENCE: 36
ggatccaaga actaccacct ggagaacgag gtggccagac tgaagaagct ggtgggcagc       60

<210> SEQ ID NO 37
<211> LENGTH: 20
<212> TYPE: PRT
<213> ORGANISM: Artificial sequence
<220> FEATURE:
<223> OTHER INFORMATION: GCN4 peptide

<400> SEQUENCE: 37

Gly Ser Lys Asn Tyr His Leu Glu Asn Glu Val Ala Arg Leu Lys Lys
1               5                   10                  15

Leu Val Gly Ser
            20

<210> SEQ ID NO 38
<211> LENGTH: 12
<212> TYPE: PRT
<213> ORGANISM: Artificial sequence
<220> FEATURE:
<223> OTHER INFORMATION: GCN4 epitope

<400> SEQUENCE: 38

Tyr His Leu Glu Asn Glu Val Ala Arg Leu Lys Lys
1               5                   10

<210> SEQ ID NO 39
<211> LENGTH: 275
<212> TYPE: PRT
<213> ORGANISM: Artificial sequence
<220> FEATURE:
<223> OTHER INFORMATION: Amino acid sequence of scFv to the GCN4 peptide

<400> SEQUENCE: 39

Met Glu Thr Asp Thr Leu Leu Leu Trp Val Leu Leu Leu Trp Val Pro
1               5                   10                  15

Gly Ser Thr Gly Asp Tyr Pro Tyr Asp Val Pro Asp Tyr Ala Gly Ala
            20                  25                  30

Asp Ala Val Val Thr Gln Glu Ser Ala Leu Thr Thr Ser Pro Gly Glu
        35                  40                  45

Thr Val Thr Leu Thr Cys Arg Ser Ser Thr Gly Ala Val Thr Thr Ser
    50                  55                  60

Asn Tyr Ala Ser Trp Val Gln Glu Lys Pro Asp His Leu Phe Thr Gly
65                  70                  75                  80

Leu Ile Gly Gly Thr Asn Asn Arg Ala Pro Gly Val Pro Ala Arg Phe
                85                  90                  95
```

```
Ser Gly Ser Leu Ile Gly Asp Lys Ala Ala Leu Thr Ile Thr Gly Ala
            100                 105                 110

Gln Thr Glu Asp Glu Ala Ile Tyr Phe Cys Ala Leu Trp Tyr Ser Asn
            115                 120                 125

His Trp Val Phe Gly Gly Gly Thr Lys Leu Thr Val Leu Gly Gly Gly
        130                 135                 140

Gly Gly Ser Gly Gly Gly Gly Ser Gly Gly Gly Gly Ser Gly Gly Gly
145                 150                 155                 160

Gly Ser Asp Val Gln Leu Gln Gln Ser Gly Pro Gly Leu Val Ala Pro
                165                 170                 175

Ser Gln Ser Leu Ser Ile Thr Cys Thr Val Ser Gly Phe Ser Leu Thr
            180                 185                 190

Asp Tyr Gly Val Asn Trp Val Arg Gln Ser Pro Gly Lys Gly Leu Glu
        195                 200                 205

Trp Leu Gly Val Ile Trp Gly Asp Gly Ile Thr Asp Tyr Asn Ser Ala
210                 215                 220

Leu Lys Ser Arg Leu Ser Val Thr Lys Asp Asn Ser Lys Ser Gln Val
225                 230                 235                 240

Phe Leu Lys Met Asn Ser Leu Gln Ser Gly Asp Ser Ala Arg Tyr Tyr
                245                 250                 255

Cys Val Thr Gly Leu Phe Asp Tyr Trp Gly Gln Gly Thr Thr Leu Thr
            260                 265                 270

Val Ser Ser
        275

<210> SEQ ID NO 40
<211> LENGTH: 1964
<212> TYPE: DNA
<213> ORGANISM: Artificial sequence
<220> FEATURE:
<223> OTHER INFORMATION: Nucleic acid sequence of scFv_GCN4_Nectin1
      chimera

<400> SEQUENCE: 40
atggaaaccg acacccttct tttgtgggtg cttcttcttt gggtgcccgg gagcaccggg      60
gactacccct acgacgtgcc cgactacgcc ggggctgatg ccgtggtgac ccaggagagc     120
gccttgacca agcccccggg ggagaccgtg accttgacct gtagaagcag cacaggggcc     180
gttacaacct ctaactacgc cagctgggtt caggagaagc ccgaccacct tttcaccgga     240
cttatcggag ggaccaacaa cagagccccc ggggtgcctg ctagattcag cgggagcctt     300
attggggaca aggccgccct taccattacc ggggctcaga ccgaagacga ggctatctac     360
ttctgtgctc tttggtacag caaccattgg gtgttcggag gcgggacaaa gcttacagtg     420
cttggaggcg gtggaggcag cggcggaggt gggtctggtg gaggggctc tggggaggc     480 ggtagcgacg tgcagcttca gcagagcggg cccgggcttg tggccccctc tcagtctctt     540
agcataacgt gcaccgtgag cgggttcagc cttaccgact atggggttaa ctgggtgaga     600
cagtctcctg ggaaggggct tgagtggttg ggagttatct ggggagacgg aatcaccgac     660
tacaacagcg ccttgaagag cagactttct gtgacaaagg acaactctaa agccaggtg     720 ttccttaaga tgaacagcct tcagagcggg gactctgcca gatactactg cgtgacaggg     780
cttttcgact actggggaca agggaccacc ttgaccgtga gcagcggaag cggagccatg     840
gccaagccca ccaactggat cgaggggaca caggccgtgc ttagagccaa gaaggggcag     900
gacgacaagg ttcttgttgc tacttgcacc agcgccaacg gaaagccccc cagcgtggtg     960
```

```
agctgggaga caagattgaa aggggaggcc gagtatcagg agatcagaaa ccctaacggg   1020
accgtgaccg tgatcagcag atacagactt gtgcctagca gagaggccca ccagcagagc   1080
cttgcctgca tcgttaacta ccacatggac agattcaagg agagccttac acttaacgtg   1140
cagtacgaac ccgaggtgac catcgagggg ttcgacggga actggtacct tcagagaatg   1200
gacgtgaagc ttacctgcaa ggccgacgcc aaccctcccg ccaccgagta ccactggacc   1260
acccttaacg ggagccttcc caaaggggtg gaggcccaga acagaaccct tttcttcaag   1320
gggcccatca attacagcct gccgggacc tacatctgcg aggccaccaa ccccatcggg   1380
accagaagcg gtcaagtgga ggtgaacatc accgagttcc cctacacccc cagcccaccc   1440
gagcacggga agagctgg gcccgttccc accgccatca tcggaggggt ggccgggagc   1500
atcttgcttg tgcttatcgt ggtgggtggg attgtggtgg cccttagaag aagaagacat   1560
accttcaaag gggactacag caccaagaag cacgtgtacg ggaacgggta cagcaaggcc   1620
ggaatccctc agcaccatcc acctatggcc cagaaccttc agtacccga cgacagcgac   1680 gatgagaaga aggctgggcc ccttggtggg agcagctacg aagaggagga agaagaggaa   1740
gagggtggcg gcggtggaga gagaaaagtg ggagggcctc atcccaaata cgacgaggac   1800
gccaagagac cctacttcac cgtggacgag gccgaggcca gacaggacgg gtacggggac   1860
agaacccttg gtaccagta cgaccccgag cagttggact tggccgagaa catggtgagc   1920
cagaacgacg gaagcttcat tctaagaag gagtggtacg tgtg             1964

<210> SEQ ID NO 41
<211> LENGTH: 654
<212> TYPE: PRT
<213> ORGANISM: Artificial sequence
<220> FEATURE:
<223> OTHER INFORMATION: Amino acid sequence of scFv_GCN4_Nectin1
      chimera

<400> SEQUENCE: 41

Met Glu Thr Asp Thr Leu Leu Leu Trp Val Leu Leu Leu Trp Val Pro
1               5                   10                  15

Gly Ser Thr Gly Asp Tyr Pro Tyr Asp Val Pro Asp Tyr Ala Gly Ala
                20                  25                  30

Asp Ala Val Val Thr Gln Glu Ser Ala Leu Thr Thr Ser Pro Gly Glu
            35                  40                  45

Thr Val Thr Leu Thr Cys Arg Ser Ser Thr Gly Ala Val Thr Thr Ser
        50                  55                  60

Asn Tyr Ala Ser Trp Val Gln Glu Lys Pro Asp His Leu Phe Thr Gly
65                  70                  75                  80

Leu Ile Gly Gly Thr Asn Asn Arg Ala Pro Gly Val Pro Ala Arg Phe
                85                  90                  95

Ser Gly Ser Leu Ile Gly Asp Lys Ala Ala Leu Thr Ile Thr Gly Ala
                100                 105                 110

Gln Thr Glu Asp Glu Ala Ile Tyr Phe Cys Ala Leu Trp Tyr Ser Asn
            115                 120                 125

His Trp Val Phe Gly Gly Gly Thr Lys Leu Thr Val Leu Gly Gly Gly
        130                 135                 140

Gly Gly Ser Gly Gly Gly Gly Ser Gly Gly Gly Gly Ser Gly Gly Gly
145                 150                 155                 160

Gly Ser Asp Val Gln Leu Gln Gln Ser Gly Pro Gly Leu Val Ala Pro
                165                 170                 175
```

```
Ser Gln Ser Leu Ser Ile Thr Cys Thr Val Ser Gly Phe Ser Leu Thr
                180                 185                 190

Asp Tyr Gly Val Asn Trp Val Arg Gln Ser Pro Gly Lys Gly Leu Glu
            195                 200                 205

Trp Leu Gly Val Ile Trp Gly Asp Gly Ile Thr Asp Tyr Asn Ser Ala
        210                 215                 220

Leu Lys Ser Arg Leu Ser Val Thr Lys Asp Asn Ser Lys Ser Gln Val
225                 230                 235                 240

Phe Leu Lys Met Asn Ser Leu Gln Ser Gly Asp Ser Ala Arg Tyr Tyr
                245                 250                 255

Cys Val Thr Gly Leu Phe Asp Tyr Trp Gly Gln Gly Thr Thr Leu Thr
            260                 265                 270

Val Ser Ser Gly Ser Gly Ala Met Ala Lys Pro Thr Asn Trp Ile Glu
        275                 280                 285

Gly Thr Gln Ala Val Leu Arg Ala Lys Lys Gly Gln Asp Asp Lys Val
        290                 295                 300

Leu Val Ala Thr Cys Thr Ser Ala Asn Gly Lys Pro Pro Ser Val Val
305                 310                 315                 320

Ser Trp Glu Thr Arg Leu Lys Gly Glu Ala Glu Tyr Gln Glu Ile Arg
                325                 330                 335

Asn Pro Asn Gly Thr Val Thr Val Ile Ser Arg Tyr Arg Leu Val Pro
            340                 345                 350

Ser Arg Glu Ala His Gln Gln Ser Leu Ala Cys Ile Val Asn Tyr His
        355                 360                 365

Met Asp Arg Phe Lys Glu Ser Leu Thr Leu Asn Val Gln Tyr Glu Pro
370                 375                 380

Glu Val Thr Ile Glu Gly Phe Asp Gly Asn Trp Tyr Leu Gln Arg Met
385                 390                 395                 400

Asp Val Lys Leu Thr Cys Lys Ala Asp Ala Asn Pro Pro Ala Thr Glu
                405                 410                 415

Tyr His Trp Thr Thr Leu Asn Gly Ser Leu Pro Lys Gly Val Glu Ala
            420                 425                 430

Gln Asn Arg Thr Leu Phe Phe Lys Gly Pro Ile Asn Tyr Ser Leu Ala
        435                 440                 445

Gly Thr Tyr Ile Cys Glu Ala Thr Asn Pro Ile Gly Thr Arg Ser Gly
        450                 455                 460

Gln Val Glu Val Asn Ile Thr Glu Phe Pro Tyr Thr Pro Ser Pro Pro
465                 470                 475                 480

Glu His Gly Arg Arg Ala Gly Pro Val Pro Thr Ala Ile Ile Gly Gly
                485                 490                 495

Val Ala Gly Ser Ile Leu Leu Val Leu Ile Val Val Gly Gly Ile Val
            500                 505                 510

Val Ala Leu Arg Arg Arg Arg His Thr Phe Lys Gly Asp Tyr Ser Thr
        515                 520                 525

Lys Lys His Val Tyr Gly Asn Gly Tyr Ser Lys Ala Gly Ile Pro Gln
530                 535                 540

His His Pro Pro Met Ala Gln Asn Leu Gln Tyr Pro Asp Asp Ser Asp
545                 550                 555                 560

Asp Glu Lys Lys Ala Gly Pro Leu Gly Gly Ser Ser Tyr Glu Glu Glu
                565                 570                 575

Glu Glu Glu Glu Glu Gly Gly Gly Gly Glu Arg Lys Val Gly Gly
            580                 585                 590

Pro His Pro Lys Tyr Asp Glu Asp Ala Lys Arg Pro Tyr Phe Thr Val
```

```
                595                 600                 605
Asp Glu Ala Glu Ala Arg Gln Asp Gly Tyr Gly Asp Arg Thr Leu Gly
            610                 615                 620

Tyr Gln Tyr Asp Pro Glu Gln Leu Asp Leu Ala Glu Asn Met Val Ser
625                 630                 635                 640

Gln Asn Asp Gly Ser Phe Ile Ser Lys Lys Glu Trp Tyr Val
                645                 650

<210> SEQ ID NO 42
<211> LENGTH: 846
<212> TYPE: DNA
<213> ORGANISM: Saccharomyces cerevisiae

<400> SEQUENCE: 42
atgtccgaat atcagccaag tttatttgct ttaaatccaa tgggtttctc accattggat      60
ggttctaaat caaccaacga aaatgtatct gcttccactt ctactgccaa accaatggtt    120
ggccaattga tttttgataa attcatcaag actgaagagg atccaattat caaacaggat    180
accccttcga accttgattt tgattttgct cttccacaaa cggcaactgc acctgatgcc    240
aagaccgttt tgccaattcc ggagctagat gccgctgtag tggaatcttt cttttcgtca    300
agcactgatt caactccaat gtttgagtat gaaaacctag aagacaactc taaagaatgg    360
acatccttgt ttgacaatga cattccagtt accactgacg atgtttcatt ggctgataag    420
gcaattgaat ccactgaaga gtttctctg gtaccatcca atctggaagt ctcgacaact    480
tcattcttac ccactcctgt tctagaagat gctaaactga ctcaaacaag aaaggttaag    540
aaaccaaatt cagtcgttaa gaagtcacat catgttggaa aggatgacga atcgagactg    600
gatcatctag gtgttgttgc ttacaaccgc aaacagcgtt cgattccact ttctccaatt    660
gtgcccgaat ccagtgatcc tgctgctcta aaacgtgcta gaaacactga agccgccagg    720
cgttctcgtg cgagaaagtt gcaaagaatg aaacaacttg aagacaaggt tgaagaattg    780
ctttcgaaaa attatcactt ggaaaatgag gttgccagat aaagaaatt agttggcgaa    840 cgctga                                                                 846

<210> SEQ ID NO 43
<211> LENGTH: 281
<212> TYPE: PRT
<213> ORGANISM: Saccharomyces cerevisiae

<400> SEQUENCE: 43

Met Ser Glu Tyr Gln Pro Ser Leu Phe Ala Leu Asn Pro Met Gly Phe
1               5                   10                  15

Ser Pro Leu Asp Gly Ser Lys Ser Thr Asn Glu Asn Val Ser Ala Ser
            20                  25                  30

Thr Ser Thr Ala Lys Pro Met Val Gly Gln Leu Ile Phe Asp Lys Phe
        35                  40                  45

Ile Lys Thr Glu Glu Asp Pro Ile Ile Lys Gln Asp Thr Pro Ser Asn
    50                  55                  60

Leu Asp Phe Asp Phe Ala Leu Pro Gln Thr Ala Thr Ala Pro Asp Ala
65                  70                  75                  80

Lys Thr Val Leu Pro Ile Pro Glu Leu Asp Asp Ala Val Val Glu Ser
                85                  90                  95

Phe Phe Ser Ser Ser Thr Asp Ser Thr Pro Met Phe Glu Tyr Glu Asn
            100                 105                 110

Leu Glu Asp Asn Ser Lys Glu Trp Thr Ser Leu Phe Asp Asn Asp Ile
```

-continued

```
            115                 120                 125
Pro Val Thr Thr Asp Asp Val Ser Leu Ala Asp Lys Ala Ile Glu Ser
        130                 135                 140

Thr Glu Glu Val Ser Leu Val Pro Ser Asn Leu Glu Val Ser Thr Thr
145                 150                 155                 160

Ser Phe Leu Pro Thr Pro Val Leu Glu Asp Ala Lys Leu Thr Gln Thr
                165                 170                 175

Arg Lys Val Lys Lys Pro Asn Ser Val Val Lys Lys Ser His His Val
            180                 185                 190

Gly Lys Asp Asp Glu Ser Arg Leu Asp His Leu Gly Val Val Ala Tyr
        195                 200                 205

Asn Arg Lys Gln Arg Ser Ile Pro Leu Ser Pro Ile Val Pro Glu Ser
    210                 215                 220

Ser Asp Pro Ala Ala Leu Lys Arg Ala Arg Asn Thr Glu Ala Ala Arg
225                 230                 235                 240

Arg Ser Arg Ala Arg Lys Leu Gln Arg Met Lys Gln Leu Glu Asp Lys
                245                 250                 255

Val Glu Glu Leu Leu Ser Lys Asn Tyr His Leu Glu Asn Glu Val Ala
            260                 265                 270

Arg Leu Lys Lys Leu Val Gly Glu Arg
        275                 280

<210> SEQ ID NO 44
<211> LENGTH: 75
<212> TYPE: DNA
<213> ORGANISM: Artificial sequence
<220> FEATURE:
<223> OTHER INFORMATION: gB_76_galK_for

<400> SEQUENCE: 44
ggccccgccc caacggggga cacgaaaccg aagaagaaca aaaaaccgaa acctgttgac      60
aattaatcat cggca                                                      75

<210> SEQ ID NO 45
<211> LENGTH: 70
<212> TYPE: DNA
<213> ORGANISM: Artificial sequence
<220> FEATURE:
<223> OTHER INFORMATION: gB_76_galK_rev

<400> SEQUENCE: 45
cccgcggcga cggtcgcgtt gtcgccggcg gggcgcggcg gcggtgggtt tcagcactgt      60
cctgctcctt                                                            70

<210> SEQ ID NO 46
<211> LENGTH: 111
<212> TYPE: DNA
<213> ORGANISM: Artificial sequence
<220> FEATURE:
<223> OTHER INFORMATION: gB_76_GCN4_for

<400> SEQUENCE: 46
ggccccgccc caacggggga cacgaaaccg aagaagaaca aaaaaccgaa aggatccaag      60
aactaccacc tggagaacga ggtggccaga ctgaagaagc tggtgggcag c             111

<210> SEQ ID NO 47
<211> LENGTH: 110
<212> TYPE: DNA
<213> ORGANISM: Artificial sequence
```

```
<220> FEATURE:
<223> OTHER INFORMATION: gB_76_GCN4_rev

<400> SEQUENCE: 47
cccgcggcga cggtcgcgtt gtcgccggcg gggcgcggcg gcggtgggtt gctgcccacc    60
agcttcttca gtctgccac ctcgttctcc aggtggtagt tcttggatcc                110

<210> SEQ ID NO 48
<211> LENGTH: 924
<212> TYPE: PRT
<213> ORGANISM: Artificial sequence
<220> FEATURE:
<223> OTHER INFORMATION: Amino acid sequence of the precursor of gB (SEQ
      ID NO: 1) having inserted the GCN4 peptide between amino acids 76
      and 77, as encoded by construct R-317

<400> SEQUENCE: 48
```

Met Arg Gln Gly Ala Pro Ala Arg Gly Cys Arg Trp Phe Val Val Trp
1               5                   10                  15

Ala Leu Leu Gly Leu Thr Leu Gly Val Leu Val Ala Ser Ala Ala Pro
            20                  25                  30

Ser Ser Pro Gly Thr Pro Gly Val Ala Ala Thr Gln Ala Ala Asn
        35                  40                  45

Gly Gly Pro Ala Thr Pro Ala Pro Pro Ala Pro Gly Pro Ala Pro Thr
50                  55                  60

Gly Asp Thr Lys Pro Lys Asn Lys Lys Pro Lys Gly Ser Lys Asn
65                  70                  75                  80

Tyr His Leu Glu Asn Glu Val Ala Arg Leu Lys Lys Leu Val Gly Ser
                85                  90                  95

Asn Pro Pro Pro Arg Pro Ala Gly Asp Asn Ala Thr Val Ala Ala
            100                 105                 110

Gly His Ala Thr Leu Arg Glu His Leu Arg Asp Ile Lys Ala Glu Asn
        115                 120                 125

Thr Asp Ala Asn Phe Tyr Val Cys Pro Pro Thr Gly Ala Thr Val
    130                 135                 140

Val Gln Phe Glu Gln Pro Arg Arg Cys Pro Thr Arg Pro Glu Gly Gln
145                 150                 155                 160

Asn Tyr Thr Glu Gly Ile Ala Val Val Phe Lys Glu Asn Ile Ala Pro
                165                 170                 175

Tyr Lys Phe Lys Ala Thr Met Tyr Tyr Lys Asp Val Thr Val Ser Gln
            180                 185                 190

Val Trp Phe Gly His Arg Tyr Ser Gln Phe Met Gly Ile Phe Glu Asp
        195                 200                 205

Arg Ala Pro Val Pro Phe Glu Glu Val Ile Asp Lys Ile Asn Ala Lys
    210                 215                 220

Gly Val Cys Arg Ser Thr Ala Lys Tyr Val Arg Asn Asn Leu Glu Thr
225                 230                 235                 240

Thr Ala Phe His Arg Asp Asp His Glu Thr Asp Met Glu Leu Lys Pro
                245                 250                 255

Ala Asn Ala Ala Thr Arg Thr Ser Arg Gly Trp His Thr Thr Asp Leu
            260                 265                 270

Lys Tyr Asn Pro Ser Arg Val Glu Ala Phe His Arg Tyr Gly Thr Thr
        275                 280                 285

Val Asn Cys Ile Val Glu Glu Val Asp Ala Arg Ser Val Tyr Pro Tyr
    290                 295                 300

Asp Glu Phe Val Leu Ala Thr Gly Asp Phe Val Tyr Met Ser Pro Phe

```
              305                 310                 315                 320
Tyr Gly Tyr Arg Glu Gly Ser His Thr Glu His Thr Ser Tyr Ala Ala
                    325                 330                 335

Asp Arg Phe Lys Gln Val Asp Gly Phe Tyr Ala Arg Asp Leu Thr Thr
                    340                 345                 350

Lys Ala Arg Ala Thr Ala Pro Thr Thr Arg Asn Leu Leu Thr Thr Pro
                    355                 360                 365

Lys Phe Thr Val Ala Trp Asp Trp Val Pro Lys Arg Pro Ser Val Cys
                    370                 375                 380

Thr Met Thr Lys Trp Gln Glu Val Asp Glu Met Leu Arg Ser Glu Tyr
385                 390                 395                 400

Gly Gly Ser Phe Arg Phe Ser Ser Asp Ala Ile Ser Thr Thr Phe Thr
                    405                 410                 415

Thr Asn Leu Thr Glu Tyr Pro Leu Ser Arg Val Asp Leu Gly Asp Cys
                    420                 425                 430

Ile Gly Lys Asp Ala Arg Asp Ala Met Asp Arg Ile Phe Ala Arg Arg
                    435                 440                 445

Tyr Asn Ala Thr His Ile Lys Val Gly Gln Pro Gln Tyr Tyr Leu Ala
                    450                 455                 460

Asn Gly Gly Phe Leu Ile Ala Tyr Gln Pro Leu Leu Ser Asn Thr Leu
465                 470                 475                 480

Ala Glu Leu Tyr Val Arg Glu His Leu Arg Glu Gln Ser Arg Lys Pro
                    485                 490                 495

Pro Asn Pro Thr Pro Pro Pro Gly Ala Ser Ala Asn Ala Ser Val
                    500                 505                 510

Glu Arg Ile Lys Thr Thr Ser Ser Ile Glu Phe Ala Arg Leu Gln Phe
                    515                 520                 525

Thr Tyr Asn His Ile Gln Arg His Val Asn Asp Met Leu Gly Arg Val
                    530                 535                 540

Ala Ile Ala Trp Cys Glu Leu Gln Asn His Glu Leu Thr Leu Trp Asn
545                 550                 555                 560

Glu Ala Arg Lys Leu Asn Pro Asn Ala Ile Ala Ser Ala Thr Val Gly
                    565                 570                 575

Arg Arg Val Ser Ala Arg Met Leu Gly Asp Val Met Ala Val Ser Thr
                    580                 585                 590

Cys Val Pro Val Ala Ala Asp Asn Val Ile Val Gln Asn Ser Met Arg
                    595                 600                 605

Ile Ser Ser Arg Pro Gly Ala Cys Tyr Ser Arg Pro Leu Val Ser Phe
                    610                 615                 620

Arg Tyr Glu Asp Gln Gly Pro Leu Val Glu Gly Gln Leu Gly Glu Asn
625                 630                 635                 640

Asn Glu Leu Arg Leu Thr Arg Asp Ala Ile Glu Pro Cys Thr Val Gly
                    645                 650                 655

His Arg Arg Tyr Phe Thr Phe Gly Gly Gly Tyr Val Tyr Phe Glu Glu
                    660                 665                 670

Tyr Ala Tyr Ser His Gln Leu Ser Arg Ala Asp Ile Thr Thr Val Ser
                    675                 680                 685

Thr Phe Ile Asp Leu Asn Ile Thr Met Leu Glu Asp His Glu Phe Val
                    690                 695                 700

Pro Leu Glu Val Tyr Thr Arg His Glu Ile Lys Asp Ser Gly Leu Leu
705                 710                 715                 720

Asp Tyr Thr Glu Val Gln Arg Arg Asn Gln Leu His Asp Leu Arg Phe
                    725                 730                 735
```

Ala Asp Ile Asp Thr Val Ile His Ala Asp Ala Asn Ala Ala Met Phe
            740                 745                 750

Ala Gly Leu Gly Ala Phe Phe Glu Gly Met Gly Asp Leu Gly Arg Ala
        755                 760                 765

Val Gly Lys Val Val Met Gly Ile Val Gly Val Val Ser Ala Val
770                 775                 780

Ser Gly Val Ser Ser Phe Met Ser Asn Pro Phe Gly Ala Leu Ala Val
785                 790                 795                 800

Gly Leu Leu Val Leu Ala Gly Leu Ala Ala Ala Phe Phe Ala Phe Arg
                805                 810                 815

Tyr Val Met Arg Leu Gln Ser Asn Pro Met Lys Ala Leu Tyr Pro Leu
            820                 825                 830

Thr Thr Lys Glu Leu Lys Asn Pro Thr Asn Pro Asp Ala Ser Gly Glu
        835                 840                 845

Gly Glu Glu Gly Gly Asp Phe Asp Glu Ala Lys Leu Ala Glu Ala Arg
850                 855                 860

Glu Met Ile Arg Tyr Met Ala Leu Val Ser Ala Met Glu Arg Thr Glu
865                 870                 875                 880

His Lys Ala Lys Lys Gly Thr Ser Ala Leu Leu Ser Ala Lys Val
                885                 890                 895

Thr Asp Met Val Met Arg Lys Arg Arg Asn Thr Asn Tyr Thr Gln Val
            900                 905                 910

Pro Asn Lys Asp Gly Asp Ala Asp Glu Asp Asp Leu
            915                 920

<210> SEQ ID NO 49
<211> LENGTH: 113
<212> TYPE: DNA
<213> ORGANISM: Artificial sequence
<220> FEATURE:
<223> OTHER INFORMATION: gB_81_GCN4_for

<400> SEQUENCE: 49 cggggacac gaaaccgaag aagaacaaaa aaccgaaaaa cccaccgccg ccgggatcca      60
agaactacca cctggagaac gaggtggcca gactgaagaa gctggtgggc agc           113

<210> SEQ ID NO 50
<211> LENGTH: 110
<212> TYPE: DNA
<213> ORGANISM: Artificial sequence
<220> FEATURE:
<223> OTHER INFORMATION: gB_81_GCN4_rev

<400> SEQUENCE: 50
cgcagggtgg cgtggcccgc ggcgacggtc gcgttgtcgc cggcggggcg gctgcccacc      60
agcttcttca gtctggccac ctcgttctcc aggtggtagt tcttggatcc                110

<210> SEQ ID NO 51
<211> LENGTH: 924
<212> TYPE: PRT
<213> ORGANISM: Artificial sequence
<220> FEATURE:
<223> OTHER INFORMATION: Amino acid sequence of the precursor of gB (SEQ
      ID NO: 1) having inserted the GCN4 peptide between amino acids 81
      and 82, as encoded by construct R-315

<400> SEQUENCE: 51

Met Arg Gln Gly Ala Pro Ala Arg Gly Cys Arg Trp Phe Val Val Trp
1               5                   10                  15

```
Ala Leu Leu Gly Leu Thr Leu Gly Val Leu Ala Ser Ala Ala Pro
             20                  25                  30

Ser Ser Pro Gly Thr Pro Gly Val Ala Ala Thr Gln Ala Ala Asn
         35                  40                  45

Gly Gly Pro Ala Thr Pro Ala Pro Pro Ala Pro Gly Pro Ala Pro Thr
     50                  55                  60

Gly Asp Thr Lys Pro Lys Lys Asn Lys Lys Pro Lys Asn Pro Pro Pro
 65              70                  75                      80

Pro Gly Ser Lys Asn Tyr His Leu Glu Asn Glu Val Ala Arg Leu Lys
                 85                  90                  95

Lys Leu Val Gly Ser Arg Pro Ala Gly Asp Asn Ala Thr Val Ala Ala
             100                 105                 110

Gly His Ala Thr Leu Arg Glu His Leu Arg Asp Ile Lys Ala Glu Asn
             115                 120                 125

Thr Asp Ala Asn Phe Tyr Val Cys Pro Pro Thr Gly Ala Thr Val
    130                 135                 140

Val Gln Phe Glu Gln Pro Arg Arg Cys Pro Thr Arg Pro Glu Gly Gln
145                 150                 155                 160

Asn Tyr Thr Glu Gly Ile Ala Val Val Phe Lys Glu Asn Ile Ala Pro
                165                 170                 175

Tyr Lys Phe Lys Ala Thr Met Tyr Tyr Lys Asp Val Thr Val Ser Gln
             180                 185                 190

Val Trp Phe Gly His Arg Tyr Ser Gln Phe Met Gly Ile Phe Glu Asp
         195                 200                 205

Arg Ala Pro Val Pro Phe Glu Glu Val Ile Asp Lys Ile Asn Ala Lys
    210                 215                 220

Gly Val Cys Arg Ser Thr Ala Lys Tyr Val Arg Asn Asn Leu Glu Thr
225                 230                 235                 240

Thr Ala Phe His Arg Asp Asp His Glu Thr Asp Met Glu Leu Lys Pro
                245                 250                 255

Ala Asn Ala Ala Thr Arg Thr Ser Arg Gly Trp His Thr Thr Asp Leu
            260                 265                 270

Lys Tyr Asn Pro Ser Arg Val Glu Ala Phe His Arg Tyr Gly Thr Thr
        275                 280                 285

Val Asn Cys Ile Val Glu Glu Val Asp Ala Arg Ser Val Tyr Pro Tyr
    290                 295                 300

Asp Glu Phe Val Leu Ala Thr Gly Asp Phe Val Tyr Met Ser Pro Phe
305                 310                 315                 320

Tyr Gly Tyr Arg Glu Gly Ser His Thr Glu His Thr Ser Tyr Ala Ala
                325                 330                 335

Asp Arg Phe Lys Gln Val Asp Gly Phe Tyr Ala Arg Asp Leu Thr Thr
            340                 345                 350

Lys Ala Arg Ala Thr Ala Pro Thr Thr Arg Asn Leu Leu Thr Thr Pro
        355                 360                 365

Lys Phe Thr Val Ala Trp Asp Trp Val Pro Lys Arg Pro Ser Val Cys
    370                 375                 380

Thr Met Thr Lys Trp Gln Glu Val Asp Glu Met Leu Arg Ser Glu Tyr
385                 390                 395                 400

Gly Gly Ser Phe Arg Phe Ser Ser Asp Ala Ile Ser Thr Thr Phe Thr
                405                 410                 415

Thr Asn Leu Thr Glu Tyr Pro Leu Ser Arg Val Asp Leu Gly Asp Cys
            420                 425                 430
```

-continued

```
Ile Gly Lys Asp Ala Arg Asp Ala Met Asp Arg Ile Phe Ala Arg Arg
            435                 440                 445
Tyr Asn Ala Thr His Ile Lys Val Gly Gln Pro Gln Tyr Tyr Leu Ala
    450                 455                 460
Asn Gly Gly Phe Leu Ile Ala Tyr Gln Pro Leu Leu Ser Asn Thr Leu
465                 470                 475                 480
Ala Glu Leu Tyr Val Arg Glu His Leu Arg Glu Gln Ser Arg Lys Pro
                485                 490                 495
Pro Asn Pro Thr Pro Pro Pro Gly Ala Ser Ala Asn Ala Ser Val
            500                 505                 510
Glu Arg Ile Lys Thr Thr Ser Ser Ile Glu Phe Ala Arg Leu Gln Phe
            515                 520                 525
Thr Tyr Asn His Ile Gln Arg His Val Asn Asp Met Leu Gly Arg Val
    530                 535                 540
Ala Ile Ala Trp Cys Glu Leu Gln Asn His Glu Leu Thr Leu Trp Asn
545                 550                 555                 560
Glu Ala Arg Lys Leu Asn Pro Asn Ala Ile Ala Ser Ala Thr Val Gly
                565                 570                 575
Arg Arg Val Ser Ala Arg Met Leu Gly Asp Val Met Ala Val Ser Thr
            580                 585                 590
Cys Val Pro Val Ala Ala Asp Asn Val Ile Val Gln Asn Ser Met Arg
            595                 600                 605
Ile Ser Ser Arg Pro Gly Ala Cys Tyr Ser Arg Pro Leu Val Ser Phe
    610                 615                 620
Arg Tyr Glu Asp Gln Gly Pro Leu Val Glu Gly Gln Leu Gly Glu Asn
625                 630                 635                 640
Asn Glu Leu Arg Leu Thr Arg Asp Ala Ile Glu Pro Cys Thr Val Gly
                645                 650                 655
His Arg Arg Tyr Phe Thr Phe Gly Gly Gly Tyr Val Tyr Phe Glu Glu
            660                 665                 670
Tyr Ala Tyr Ser His Gln Leu Ser Arg Ala Asp Ile Thr Thr Val Ser
    675                 680                 685
Thr Phe Ile Asp Leu Asn Ile Thr Met Leu Glu Asp His Glu Phe Val
690                 695                 700
Pro Leu Glu Val Tyr Thr Arg His Glu Ile Lys Asp Ser Gly Leu Leu
705                 710                 715                 720
Asp Tyr Thr Glu Val Gln Arg Arg Asn Gln Leu His Asp Leu Arg Phe
                725                 730                 735
Ala Asp Ile Asp Thr Val Ile His Ala Asp Ala Asn Ala Ala Met Phe
            740                 745                 750
Ala Gly Leu Gly Ala Phe Phe Glu Gly Met Gly Asp Leu Gly Arg Ala
            755                 760                 765
Val Gly Lys Val Val Met Gly Ile Val Gly Gly Val Val Ser Ala Val
    770                 775                 780
Ser Gly Val Ser Ser Phe Met Ser Asn Pro Phe Gly Ala Leu Ala Val
785                 790                 795                 800
Gly Leu Leu Val Leu Ala Gly Leu Ala Ala Ala Phe Phe Ala Phe Arg
                805                 810                 815
Tyr Val Met Arg Leu Gln Ser Asn Pro Met Lys Ala Leu Tyr Pro Leu
            820                 825                 830
Thr Thr Lys Glu Leu Lys Asn Pro Thr Asn Pro Asp Ala Ser Gly Glu
            835                 840                 845
Gly Glu Glu Gly Gly Asp Phe Asp Glu Ala Lys Leu Ala Glu Ala Arg
```

Glu Met Ile Arg Tyr Met Ala Leu Val Ser Ala Met Glu Arg Thr Glu
850                 855                 860
865                 870                 875                 880

His Lys Ala Lys Lys Lys Gly Thr Ser Ala Leu Leu Ser Ala Lys Val
                885                 890                 895

Thr Asp Met Val Met Arg Lys Arg Arg Asn Thr Asn Tyr Thr Gln Val
            900                 905                 910

Pro Asn Lys Asp Gly Asp Ala Asp Glu Asp Asp Leu
        915                 920

<210> SEQ ID NO 52
<211> LENGTH: 74
<212> TYPE: DNA
<213> ORGANISM: Artificial sequence
<220> FEATURE:
<223> OTHER INFORMATION: gB_95_galK_for

<400> SEQUENCE: 52
cgccgccgcg ccccgccggc gacaacgcga ccgtcgccgc gggccacgcc cctgttgaca    60
attaatcatc ggca                                                      74

<210> SEQ ID NO 53
<211> LENGTH: 71
<212> TYPE: DNA
<213> ORGANISM: Artificial sequence
<220> FEATURE:
<223> OTHER INFORMATION: gB_95_galK_rev

<400> SEQUENCE: 53
gtttgcatcg gtgttctccg ccttgatgtc ccgcaggtgc tcgcgcaggg ttcagcactg    60
tcctgctcct t                                                         71

<210> SEQ ID NO 54
<211> LENGTH: 110
<212> TYPE: DNA
<213> ORGANISM: Artificial sequence
<220> FEATURE:
<223> OTHER INFORMATION: gB_95_GCN4_for

<400> SEQUENCE: 54
cgccgccgcg ccccgccggc gacaacgcga ccgtcgccgc gggccacgcc ggatccaaga    60
actaccacct ggagaacgag gtggccagac tgaagaagct ggtgggcagc               110

<210> SEQ ID NO 55
<211> LENGTH: 111
<212> TYPE: DNA
<213> ORGANISM: Artificial sequence
<220> FEATURE:
<223> OTHER INFORMATION: gB_95_GCN4_rev

<400> SEQUENCE: 55
gtttgcatcg gtgttctccg ccttgatgtc ccgcaggtgc tcgcgcaggg tgctgcccac    60
cagcttcttc agtctggcca cctcgttctc caggtggtag ttcttggatc c             111

<210> SEQ ID NO 56
<211> LENGTH: 924
<212> TYPE: PRT
<213> ORGANISM: Artificial sequence
<220> FEATURE:
<223> OTHER INFORMATION: Amino acid sequence of the precursor of gB (SEQ
      ID NO: 1) having inserted the GCN4 peptide between amino acids 95
      and 96, as encoded by construct R-319

<400> SEQUENCE: 56

Met Arg Gln Gly Ala Pro Ala Arg Gly Cys Arg Trp Phe Val Val Trp
1               5                   10                  15

Ala Leu Leu Gly Leu Thr Leu Gly Val Leu Val Ala Ser Ala Ala Pro
            20                  25                  30

Ser Ser Pro Gly Thr Pro Gly Val Ala Ala Thr Gln Ala Ala Asn
        35                  40                  45

Gly Gly Pro Ala Thr Pro Ala Pro Pro Ala Pro Gly Pro Ala Pro Thr
    50                  55                  60

Gly Asp Thr Lys Pro Lys Lys Asn Lys Pro Lys Asn Pro Pro Pro
65              70                  75                  80

Pro Arg Pro Ala Gly Asp Asn Ala Thr Val Ala Ala Gly His Ala Gly
                85                  90                  95

Ser Lys Asn Tyr His Leu Glu Asn Glu Val Ala Arg Leu Lys Lys Leu
            100                 105                 110

Val Gly Ser Thr Leu Arg Glu His Leu Arg Asp Ile Lys Ala Glu Asn
            115                 120                 125

Thr Asp Ala Asn Phe Tyr Val Cys Pro Pro Thr Gly Ala Thr Val
130                 135                 140

Val Gln Phe Glu Gln Pro Arg Arg Cys Pro Thr Arg Pro Glu Gly Gln
145                 150                 155                 160

Asn Tyr Thr Glu Gly Ile Ala Val Val Phe Lys Glu Asn Ile Ala Pro
                165                 170                 175

Tyr Lys Phe Lys Ala Thr Met Tyr Tyr Lys Asp Val Thr Val Ser Gln
            180                 185                 190

Val Trp Phe Gly His Arg Tyr Ser Gln Phe Met Gly Ile Phe Glu Asp
            195                 200                 205

Arg Ala Pro Val Pro Phe Glu Glu Val Ile Asp Lys Ile Asn Ala Lys
210                 215                 220

Gly Val Cys Arg Ser Thr Ala Lys Tyr Val Arg Asn Asn Leu Glu Thr
225                 230                 235                 240

Thr Ala Phe His Arg Asp Asp His Glu Thr Asp Met Glu Leu Lys Pro
                245                 250                 255

Ala Asn Ala Ala Thr Arg Thr Ser Arg Gly Trp His Thr Thr Asp Leu
            260                 265                 270

Lys Tyr Asn Pro Ser Arg Val Glu Ala Phe His Arg Tyr Gly Thr Thr
            275                 280                 285

Val Asn Cys Ile Val Glu Glu Val Asp Ala Arg Ser Val Tyr Pro Tyr
290                 295                 300

Asp Glu Phe Val Leu Ala Thr Gly Asp Phe Val Tyr Met Ser Pro Phe
305                 310                 315                 320

Tyr Gly Tyr Arg Glu Gly Ser His Thr Glu His Thr Ser Tyr Ala Ala
                325                 330                 335

Asp Arg Phe Lys Gln Val Asp Gly Phe Tyr Ala Arg Asp Leu Thr Thr
            340                 345                 350

Lys Ala Arg Ala Thr Ala Pro Thr Thr Arg Asn Leu Leu Thr Thr Pro
            355                 360                 365

Lys Phe Thr Val Ala Trp Asp Trp Val Pro Lys Arg Pro Ser Val Cys
            370                 375                 380

Thr Met Thr Lys Trp Gln Glu Val Asp Glu Met Leu Arg Ser Glu Tyr
385                 390                 395                 400

Gly Gly Ser Phe Arg Phe Ser Ser Asp Ala Ile Ser Thr Thr Phe Thr

-continued

```
            405                 410                 415
Thr Asn Leu Thr Glu Tyr Pro Leu Ser Arg Val Asp Leu Gly Asp Cys
            420                 425                 430

Ile Gly Lys Asp Ala Arg Asp Ala Met Asp Arg Ile Phe Ala Arg Arg
            435                 440                 445

Tyr Asn Ala Thr His Ile Lys Val Gly Gln Pro Gln Tyr Tyr Leu Ala
            450                 455                 460

Asn Gly Gly Phe Leu Ile Ala Tyr Gln Pro Leu Leu Ser Asn Thr Leu
465                 470                 475                 480

Ala Glu Leu Tyr Val Arg Glu His Leu Arg Glu Gln Ser Arg Lys Pro
            485                 490                 495

Pro Asn Pro Thr Pro Pro Pro Gly Ala Ser Ala Asn Ala Ser Val
            500                 505                 510

Glu Arg Ile Lys Thr Thr Ser Ser Ile Glu Phe Ala Arg Leu Gln Phe
            515                 520                 525

Thr Tyr Asn His Ile Gln Arg His Val Asn Asp Met Leu Gly Arg Val
            530                 535                 540

Ala Ile Ala Trp Cys Glu Leu Gln Asn His Glu Leu Thr Leu Trp Asn
545                 550                 555                 560

Glu Ala Arg Lys Leu Asn Pro Asn Ala Ile Ala Ser Ala Thr Val Gly
            565                 570                 575

Arg Arg Val Ser Ala Arg Met Leu Gly Asp Val Met Ala Val Ser Thr
            580                 585                 590

Cys Val Pro Val Ala Ala Asp Asn Val Ile Val Gln Asn Ser Met Arg
            595                 600                 605

Ile Ser Ser Arg Pro Gly Ala Cys Tyr Ser Arg Pro Leu Val Ser Phe
            610                 615                 620

Arg Tyr Glu Asp Gln Gly Pro Leu Val Glu Gly Gln Leu Gly Glu Asn
625                 630                 635                 640

Asn Glu Leu Arg Leu Thr Arg Asp Ala Ile Glu Pro Cys Thr Val Gly
            645                 650                 655

His Arg Arg Tyr Phe Thr Phe Gly Gly Gly Tyr Val Tyr Phe Glu Glu
            660                 665                 670

Tyr Ala Tyr Ser His Gln Leu Ser Arg Ala Asp Ile Thr Thr Val Ser
            675                 680                 685

Thr Phe Ile Asp Leu Asn Ile Thr Met Leu Glu Asp His Glu Phe Val
            690                 695                 700

Pro Leu Glu Val Tyr Thr Arg His Glu Ile Lys Asp Ser Gly Leu Leu
705                 710                 715                 720

Asp Tyr Thr Glu Val Gln Arg Arg Asn Gln Leu His Asp Leu Arg Phe
            725                 730                 735

Ala Asp Ile Asp Thr Val Ile His Ala Asp Ala Asn Ala Ala Met Phe
            740                 745                 750

Ala Gly Leu Gly Ala Phe Phe Glu Gly Met Gly Asp Leu Gly Arg Ala
            755                 760                 765

Val Gly Lys Val Val Met Gly Ile Val Gly Gly Val Val Ser Ala Val
            770                 775                 780

Ser Gly Val Ser Ser Phe Met Ser Asn Pro Phe Gly Ala Leu Ala Val
785                 790                 795                 800

Gly Leu Leu Val Leu Ala Gly Leu Ala Ala Ala Phe Phe Ala Phe Arg
            805                 810                 815

Tyr Val Met Arg Leu Gln Ser Asn Pro Met Lys Ala Leu Tyr Pro Leu
            820                 825                 830
```

```
Thr Thr Lys Glu Leu Lys Asn Pro Thr Asn Pro Asp Ala Ser Gly Glu
            835                 840                 845

Gly Glu Glu Gly Gly Asp Phe Asp Glu Ala Lys Leu Ala Glu Ala Arg
    850                 855                 860

Glu Met Ile Arg Tyr Met Ala Leu Val Ser Ala Met Glu Arg Thr Glu
865                 870                 875                 880

His Lys Ala Lys Lys Lys Gly Thr Ser Ala Leu Leu Ser Ala Lys Val
                885                 890                 895

Thr Asp Met Val Met Arg Lys Arg Arg Asn Thr Asn Tyr Thr Gln Val
            900                 905                 910

Pro Asn Lys Asp Gly Asp Ala Asp Glu Asp Asp Leu
            915                 920

<210> SEQ ID NO 57
<211> LENGTH: 74
<212> TYPE: DNA
<213> ORGANISM: Artificial sequence
<220> FEATURE:
<223> OTHER INFORMATION: gD5_galK_f

<400> SEQUENCE: 57
ttgtcgtcat agtgggcctc catggggtcc gcggcaaata tgccttggcg cctgttgaca    60
attaatcatc ggca                                                     74

<210> SEQ ID NO 58
<211> LENGTH: 70
<212> TYPE: DNA
<213> ORGANISM: Artificial sequence
<220> FEATURE:
<223> OTHER INFORMATION: scFv_galK_rev

<400> SEQUENCE: 58
gaggcggaca gggagctcgg ggactgggtc atctggatat cggaattctc tcagcactgt    60
cctgctcctt                                                          70

<210> SEQ ID NO 59
<211> LENGTH: 108
<212> TYPE: DNA
<213> ORGANISM: Artificial sequence
<220> FEATURE:
<223> OTHER INFORMATION: gDdel30_38for

<400> SEQUENCE: 59
ttgtcgtcat agtgggcctc catggggtcc gcggcaaata tgccttggcg gatgcctctc    60
tcaagatggc cgaccccaat cgctttcgcg gcaaagacct tccggtcc               108

<210> SEQ ID NO 60
<211> LENGTH: 108
<212> TYPE: DNA
<213> ORGANISM: Artificial sequence
<220> FEATURE:
<223> OTHER INFORMATION: gDdel30_38rev

<400> SEQUENCE: 60
gaggcggaca gggagctcgg ggactgggtc atctggatat cggaattctc cacgcgccgg    60
acccccggag gggtcagctg gtccaggacc ggaaggtctt tgccgcga               108

<210> SEQ ID NO 61
<211> LENGTH: 652
<212> TYPE: PRT
```

<213> ORGANISM: Artificial sequence
<220> FEATURE:
<223> OTHER INFORMATION: Amino acid sequence of the precursor of gD (SEQ ID NO: 4) having deleted amino acids 30 and 38 and inserted the trastuzumab scFv after amino acid 37 with regard to mature gD, as encoded by construct R-321

<400> SEQUENCE: 61

```
Met Gly Gly Ala Ala Ala Arg Leu Gly Ala Val Ile Leu Phe Val Val
1               5                   10                  15

Ile Val Gly Leu His Gly Val Arg Gly Lys Tyr Ala Leu Ala Asp Ala
            20                  25                  30

Ser Leu Lys Met Ala Asp Pro Asn Arg Phe Arg Gly Lys Asp Leu Pro
        35                  40                  45

Val Leu Asp Gln Leu Thr Pro Pro Gly Val Arg Arg Val Glu Asn Ser
    50                  55                  60

Asp Ile Gln Met Thr Gln Ser Pro Ser Ser Leu Ser Ala Ser Val Gly
65                  70                  75                  80

Asp Arg Val Thr Ile Thr Cys Arg Ala Ser Gln Asp Val Asn Thr Ala
                85                  90                  95

Val Ala Trp Tyr Gln Gln Lys Pro Gly Lys Ala Pro Lys Leu Leu Ile
            100                 105                 110

Tyr Ser Ala Ser Phe Leu Tyr Ser Gly Val Pro Ser Arg Phe Ser Gly
        115                 120                 125

Ser Arg Ser Gly Thr Asp Phe Thr Leu Thr Ile Ser Ser Leu Gln Pro
    130                 135                 140

Glu Asp Phe Ala Thr Tyr Tyr Cys Gln Gln His Tyr Thr Thr Pro Pro
145                 150                 155                 160

Thr Phe Gly Gln Gly Thr Lys Val Glu Ile Lys Ser Asp Met Pro Met
                165                 170                 175

Ala Asp Pro Asn Arg Phe Arg Gly Lys Asn Leu Val Phe His Ser Glu
            180                 185                 190

Val Gln Leu Val Glu Ser Gly Gly Gly Leu Val Gln Pro Gly Gly Ser
        195                 200                 205

Leu Arg Leu Ser Cys Ala Ala Ser Gly Phe Asn Ile Lys Asp Thr Tyr
    210                 215                 220

Ile His Trp Val Arg Gln Ala Pro Gly Lys Gly Leu Glu Trp Val Ala
225                 230                 235                 240

Arg Ile Tyr Pro Thr Asn Gly Tyr Thr Arg Tyr Ala Asp Ser Val Lys
                245                 250                 255

Gly Arg Phe Thr Ile Ser Ala Asp Thr Ser Lys Asn Thr Ala Tyr Leu
            260                 265                 270

Gln Met Asn Ser Leu Arg Ala Glu Asp Thr Ala Val Tyr Tyr Cys Ser
        275                 280                 285

Arg Trp Gly Gly Asp Gly Phe Tyr Ala Met Asp Tyr Trp Gly Gln Gly
    290                 295                 300

Thr Leu Val Thr Val Ser Ser Ser Gly Gly Gly Ser Gly Ser Gly Gly
305                 310                 315                 320

Ser His Ile Gln Ala Gly Leu Pro Asp Pro Phe Gln Pro Pro Ser Leu
                325                 330                 335

Pro Ile Thr Val Tyr Tyr Ala Val Leu Glu Arg Ala Cys Arg Ser Val
            340                 345                 350

Leu Leu Asn Ala Pro Ser Glu Ala Pro Gln Ile Val Arg Gly Ala Ser
        355                 360                 365

Glu Asp Val Arg Lys Gln Pro Tyr Asn Leu Thr Ile Ala Trp Phe Arg
```

```
                     370                 375                 380
Met Gly Gly Asn Cys Ala Ile Pro Ile Thr Val Met Glu Tyr Thr Glu
385                 390                 395                 400

Cys Ser Tyr Asn Lys Ser Leu Gly Ala Cys Pro Ile Arg Thr Gln Pro
                405                 410                 415

Arg Trp Asn Tyr Tyr Asp Ser Phe Ser Ala Val Ser Glu Asp Asn Leu
            420                 425                 430

Gly Phe Leu Met His Ala Pro Ala Phe Glu Thr Ala Gly Thr Tyr Leu
        435                 440                 445

Arg Leu Val Lys Ile Asn Asp Trp Thr Glu Ile Thr Gln Phe Ile Leu
    450                 455                 460

Glu His Arg Ala Lys Gly Ser Cys Lys Tyr Ala Leu Pro Leu Arg Ile
465                 470                 475                 480

Pro Pro Ser Ala Cys Leu Ser Pro Gln Ala Tyr Gln Gln Gly Val Thr
                485                 490                 495

Val Asp Ser Ile Gly Met Leu Pro Arg Phe Ile Pro Glu Asn Gln Arg
            500                 505                 510

Thr Val Ala Val Tyr Ser Leu Lys Ile Ala Gly Trp His Gly Pro Lys
        515                 520                 525

Ala Pro Tyr Thr Ser Thr Leu Leu Pro Pro Glu Leu Ser Glu Thr Pro
    530                 535                 540

Asn Ala Thr Gln Pro Glu Leu Ala Pro Glu Asp Pro Glu Asp Ser Ala
545                 550                 555                 560

Leu Leu Glu Asp Pro Val Gly Thr Val Ala Pro Gln Ile Pro Pro Asn
                565                 570                 575

Trp His Ile Pro Ser Ile Gln Asp Ala Ala Thr Pro Tyr His Pro Pro
            580                 585                 590

Ala Thr Pro Asn Asn Met Gly Leu Ile Ala Gly Ala Val Gly Gly Ser
        595                 600                 605

Leu Leu Ala Ala Leu Val Ile Cys Gly Ile Val Tyr Trp Met Arg Arg
    610                 615                 620

Arg Thr Gln Lys Ala Pro Lys Arg Ile Arg Leu Pro His Ile Arg Glu
625                 630                 635                 640

Asp Asp Gln Pro Ser Ser His Gln Pro Leu Phe Tyr
                645                 650

<210> SEQ ID NO 62
<211> LENGTH: 369
<212> TYPE: PRT
<213> ORGANISM: Herpes simplex virus 1

<400> SEQUENCE: 62

Lys Tyr Ala Leu Ala Asp Ala Ser Leu Lys Met Ala Asp Pro Asn Arg
1               5                   10                  15

Phe Arg Gly Lys Asp Leu Pro Val Leu Asp Gln Leu Thr Asp Pro Pro
            20                  25                  30

Gly Val Arg Arg Val Tyr His Ile Gln Ala Gly Leu Pro Asp Pro Phe
        35                  40                  45

Gln Pro Pro Ser Leu Pro Ile Thr Val Tyr Tyr Ala Val Leu Glu Arg
    50                  55                  60

Ala Cys Arg Ser Val Leu Leu Asn Ala Pro Ser Glu Ala Pro Gln Ile
65                  70                  75                  80

Val Arg Gly Ala Ser Glu Asp Val Arg Lys Gln Pro Tyr Asn Leu Thr
                85                  90                  95
```

-continued

```
Ile Ala Trp Phe Arg Met Gly Gly Asn Cys Ala Ile Pro Ile Thr Val
            100                 105             110
Met Glu Tyr Thr Glu Cys Ser Tyr Asn Lys Ser Leu Gly Ala Cys Pro
        115                 120             125
Ile Arg Thr Gln Pro Arg Trp Asn Tyr Tyr Asp Ser Phe Ser Ala Val
    130                 135             140
Ser Glu Asp Asn Leu Gly Phe Leu Met His Ala Pro Ala Phe Glu Thr
145                 150             155                 160
Ala Gly Thr Tyr Leu Arg Leu Val Lys Ile Asn Asp Trp Thr Glu Ile
                165             170                 175
Thr Gln Phe Ile Leu Glu His Arg Ala Lys Gly Ser Cys Lys Tyr Ala
            180             185                 190
Leu Pro Leu Arg Ile Pro Pro Ser Ala Cys Leu Ser Pro Gln Ala Tyr
        195                 200             205
Gln Gln Gly Val Thr Val Asp Ser Ile Gly Met Leu Pro Arg Phe Ile
    210                 215             220
Pro Glu Asn Gln Arg Thr Val Ala Val Tyr Ser Leu Lys Ile Ala Gly
225                 230             235                 240
Trp His Gly Pro Lys Ala Pro Tyr Thr Ser Thr Leu Leu Pro Pro Glu
                245             250                 255
Leu Ser Glu Thr Pro Asn Ala Thr Gln Pro Glu Leu Ala Pro Glu Asp
            260                 265             270
Pro Glu Asp Ser Ala Leu Leu Glu Asp Pro Val Gly Thr Val Ala Pro
        275                 280             285
Gln Ile Pro Pro Asn Trp His Ile Pro Ser Ile Gln Asp Ala Ala Thr
    290                 295             300
Pro Tyr His Pro Pro Ala Thr Pro Asn Asn Met Gly Leu Ile Ala Gly
305                 310             315                 320
Ala Val Gly Gly Ser Leu Leu Ala Ala Leu Val Ile Cys Gly Ile Val
                325             330                 335
Tyr Trp Met Arg Arg Arg Thr Gln Lys Ala Pro Lys Arg Ile Arg Leu
            340             345                 350
Pro His Ile Arg Glu Asp Asp Gln Pro Ser Ser His Gln Pro Leu Phe
        355                 360             365
Tyr
```

The invention claimed is:

1. A recombinant herpesvirus comprising a heterologous polypeptide ligand capable of binding to a target molecule and inserted into glycoprotein B (gB) present in the envelope of the herpesvirus, wherein the ligand has a length of 5 to 30 amino acids and is inserted at any amino acid within the N-terminal region spanning from amino acids 31 to 108 of gB according to SEQ ID NO: 1, or within a corresponding region of a homologous gB.

2. The herpesvirus of claim 1, wherein the herpesvirus has the capability of binding to a cell expressing or binding the target molecule, fusing with the cell membrane, entering the cell, or killing the cell.

3. The herpesvirus according to claim 1, wherein the target molecule is present on a diseased cell or on a cell present in cell culture.

4. The herpesvirus according to claim 3, wherein the target molecule present on a diseased cell is a tumor-associated receptor selected from the group consisting of: a member of the EGF receptor family, HER2, EGFR, EGFRIII, or EGFR3 (ERBB3), EGFRvIII, or MET, FAP, PSMA, CXCR4, CEA, CADC, Mucins, Folate-binding protein, GD2, VEGF receptors 1 and 2, CD20, CD30, CD33, CD52, CD55, the integrin family, IGF1R, the Ephrin receptor family, the protein-tyrosine kinase (TK) family, RANKL, TRAILR1, TRAILR2, IL13Ralpha, UPAR, Tenascin, a member of the immune checkpoint family regulators, PD-1, PD-L1, CTL-A4, TIM-3, LAG3, or IDO, tumor-associated glycoprotein 72, ganglioside GM2, A33, Lewis Y antigen, and MUC1; or wherein the target molecule present on a cell present in cell culture is an artificial molecule, an antibody, an antibody derivative or an antibody mimetic, or a single-chain antibody (scFv).

5. The herpesvirus according to claim 1, wherein the ligand is a natural polypeptide or an artificial polypeptide.

6. The herpesvirus according to claim 1, wherein a) the target molecule is HER2, b) the target molecule comprises the amino acid sequence of SEQ ID NO: 41, or c) the ligand comprises the amino acid sequence of SEQ ID NO: 37.

7. The herpesvirus according to claim 1, further comprising one or more ligands, wherein the one or more ligands are fused to or inserted into gB; or wherein the gB comprises a ligand capable of binding to a target molecule present on a cell present in cell culture and a ligand capable of binding to a target molecule present on a diseased cell.

8. The herpesvirus according to claim 1, wherein the herpesvirus comprises a modified gD and/or a modified gH.

9. The herpesvirus according to claim 8, wherein the gD is modified to have a deletion of
  a) amino acids 30 to 38 of gD or a subset thereof,
  b) a deletion of amino acid 30 or amino acid 38, or
  c) a deletion of amino acid 30 and amino acid 38,
  with regard to mature gD according to SEQ ID NO: 62 or a corresponding region of a homologous gD.

10. The herpesvirus according to claim 8, wherein a heterologous polypeptide ligand is inserted into gD instead of
  a) amino acids 30 to 38 or a subset thereof,
  b) amino acid 30 or amino acid 38, or
  c) amino acid 38 and amino acid 30 is deleted,
  with regard to mature gD according to SEQ ID NO: 62 or a corresponding region of a homologous gD.

11. The herpesvirus according to claim 1, wherein the herpesvirus encodes one or more molecules that stimulate(s) the host immune response against a cell.

12. A pharmaceutical composition comprising the herpesvirus according to claim 1 and a pharmaceutically acceptable carrier.

13. A nucleic acid molecule comprising a nucleic acid coding for the gB of the herpesvirus according to claim 1, having inserted the ligand, or
  a vector comprising said nucleic acid molecule, or
  a polypeptide comprising said gB, having inserted the ligand, or
  a cell comprising said herpesvirus, said nucleic acid molecule, said vector, or said polypeptide.

14. The herpesvirus according to claim 3, wherein the diseased cell is a tumor cell, an infected cell, a degenerative disorder-associated cell, or a senescent cell.

15. The herpesvirus according to claim 3, wherein the cultured cell is a Vero cell, a 293 cell, a 293T cell, a HEp-2 cell, a HeLa cell, a BHK cell, or a RS cell.

16. The herpesvirus according to claim 14, wherein the tumor cell is a breast cancer cell, ovary cancer cell, stomach cancer cell, lung cancer cell, head and neck cancer cell, osteosarcoma cell, glioblastoma multiforme cell, or salivary gland tumor cell.

17. The herpesvirus according to claim 4, wherein the scFv is capable of binding to a part of the GCN4 yeast transcription factor.

18. The herpesvirus according to claim 1, wherein the ligand is capable of binding to a part of the GCN4 yeast transcription factor.

19. The herpesvirus according to claim 8, wherein the gB comprises a ligand capable of binding to a target molecule present on a cell present in cell culture and the modified gD and/or the modified gH comprises a ligand capable of binding to a target molecule present on a diseased cell.

20. The pharmaceutical composition of claim 12, further comprising one or more molecules that stimulate the host immune response against a cell.

* * * * *